(12) United States Patent
Wolfe et al.

(10) Patent No.: US 11,400,135 B2
(45) Date of Patent: *Aug. 2, 2022

(54) COMPOSITIONS AND METHODS FOR TREATING OBESITY AND HYPERPHAGIA

(71) Applicant: MHS CARE-INNOVATION LLC, Cleveland, OH (US)

(72) Inventors: M. Michael Wolfe, Bal Harbour, FL (US); Michael O. Boylan, Milton, MA (US)

(73) Assignee: MHS CARE-INNOVATION LLC, Cleveland, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 16/781,304

(22) Filed: Feb. 4, 2020

(65) Prior Publication Data
US 2020/0155649 A1    May 21, 2020

Related U.S. Application Data

(60) Division of application No. 15/714,552, filed on Sep. 25, 2017, now Pat. No. 10,548,951, which is a continuation-in-part of application No. 14/573,600, filed on Dec. 17, 2014, now Pat. No. 9,771,422.

(60) Provisional application No. 62/527,968, filed on Jun. 30, 2017, provisional application No. 62/428,982, filed on Dec. 1, 2016, provisional application No. 62/074,227, filed on Nov. 3, 2014, provisional application No. 62/074,225, filed on Nov. 3, 2014, provisional application No. 62/074,234, filed on Nov. 3, 2014, provisional application No. 62/045,189, filed on Sep. 3, 2014, provisional application No. 62/007,255, filed on Jun. 3, 2014, provisional application No. 61/974,660, filed on Apr. 3, 2014, provisional application No. 61/917,136, filed on Dec. 17, 2013.

(51) Int. Cl.
| | |
|---|---|
| *A61K 38/22* | (2006.01) |
| *A61K 39/00* | (2006.01) |
| *C07K 14/47* | (2006.01) |
| *A61K 9/00* | (2006.01) |
| *A61P 5/00* | (2006.01) |
| *C07K 16/26* | (2006.01) |

(52) U.S. Cl.
CPC .......... *A61K 38/2235* (2013.01); *A61K 9/0019* (2013.01); *A61K 39/0005* (2013.01); *A61P 5/00* (2018.01); *C07K 14/4703* (2013.01); *C07K 16/26* (2013.01); *A61K 2039/505* (2013.01); *C07K 2317/24* (2013.01); *C07K 2317/76* (2013.01)

(58) Field of Classification Search
CPC .......... A61K 38/2235; A61K 2039/505; C07K 2317/76
See application file for complete search history.

(56) References Cited

U.S. PATENT DOCUMENTS

2006/0088550 A1    4/2006    Bachmann et al.

FOREIGN PATENT DOCUMENTS

| RU | 2339398 C2 | 11/2008 |
| WO | WO 2015/095354 A2 | 6/2015 |

OTHER PUBLICATIONS

Chamow and Ashkenazi, TIBTECH 14: 52-60, (1996).*
Rudikoff S et al, Single Amino Acid Substitution Altering Antigen-Binding Specificity, Mar. 1, 1982, pp. 1979-1983, vol. 79, Proceedings National Academy of Sciences, National Academy of Sciences, US.
Miyawaki K et al, Inhibition of Gastric Inhibitory Polypeptide Signaling Prevents Obesity, online, Jun. 17, 2002, pp. 738-742, vol. 8, No. 7, Nature Publishing Group.
Schildbach, Joel F., Modulation of Antibody Affinity by a Non-Contact Residue, Protein Science, 1993, pp. 206-214, Cambridge University Press, USA.
Roitt, Ivan, Essential Immunology, 1984, pp. 110-111, 5$^{th}$ Edition, Blackwell Scientific Publications, Oxford UK—Corresponds with pp. 80-81 of English edition of text (submitted herewith along with Russian edition as originally cited).

(Continued)

*Primary Examiner* — Gyan Chandra
(74) *Attorney, Agent, or Firm* — Morgan, Lewis & Bockius LLP

(57) ABSTRACT

The present disclosure is directed to the treatment of diseases or conditions characterized by the buildup of fatty tissue, or hyperphagia, such as Prader-Willi syndrome, obesity, metabolic syndrome, type II diabetes, etc. A composition containing a monoclonal antibody directed against gastric inhibitory polypeptide is administered. This results in a reduced rate of weight gain, weight loss, and/or reduction in fatty tissue, and a marked decrease in lipid synthesis and accumulation.

11 Claims, 24 Drawing Sheets
(4 of 24 Drawing Sheet(s) Filed in Color)
Specification includes a Sequence Listing.

(56) References Cited

OTHER PUBLICATIONS

Fulurija A. et al., Vaccination against GIP for the treatment of obesity. PLoS ONE, 2008, pp. 1-11, vol. 3, Issue 9, e3163, doi:10.1371/journal.pone.0003163.
Ebert et al., "Influence of Gastric Inhibitory Polypeptide Antiserum on Glucose-Induced Insulin Secretion in Rats," Endocrinology, 1982, pp. 1601-1606, vol. 111, No. 5, The Endocrine Society, U.S.A.
Gault et al., "Glucose-dependent insulinotropc polypeptide (GIP): anti-diabetic and anti-obesity potential?" Neuropeptides, Sep. 8, 2003, pp. 253-263, vol. 37, School of Biomedical Sciences, Coleraine, Northern Ireland.
Kang et al., "Antibody redesign by chain shuffling from random combinatorial immunoglobulin libraries," Immunology, Dec. 1991, pp. 11120-11123, vol. 88, Proc. Natl. Acad. Sci., U.S.A.

* cited by examiner

SEQUENCE LISTING

<160> NUMBER OF SEQ ID NOS: 55

<210> SEQ ID NO 1
<211> LENGTH: 42
<212> TYPE: PRT
<213> ORGANISM: Homo sapiens

<400> SEQUENCE: 1

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 2
<211> LENGTH: 42
<212> TYPE: PRT
<213> ORGANISM: Mus musculus

<400> SEQUENCE: 2

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Arg Gly Lys
            20                  25                  30

Lys Ser Asp Trp Lys His Asn Ile Thr Gln
            35                  40

<210> SEQ ID NO 3
<211> LENGTH: 42
<212> TYPE: PRT
<213> ORGANISM: Rattus norvegicus

<400> SEQUENCE: 3

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Gly Lys
            20                  25                  30

Lys Asn Asp Trp Lys His Asn Leu Thr Gln
            35                  40

<210> SEQ ID NO 4
<211> LENGTH: 42
<212> TYPE: PRT
<213> ORGANISM: Sus scrofa

<400> SEQUENCE: 4

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Gly Lys
            20                  25                  30

Lys Ser Asp Trp Lys His Asn Ile Thr Gln
            35                  40

<210> SEQ ID NO 5
<211> LENGTH: 18
<212> TYPE: PRT
<213> ORGANISM: Artificial Sequence
<220> FEATURE:
<223> OTHER INFORMATION: artificial screening peptide

<400> SEQUENCE: 5

Tyr Ala Glu Gly Thr Phe Ile Ser Asp Tyr Ser Ile Ala Met Asp Lys
1               5                   10                  15

Ile Cys

<210> SEQ ID NO 6
<211> LENGTH: 18
<212> TYPE: PRT
<213> ORGANISM: Artificial Sequence
<220> FEATURE:
<223> OTHER INFORMATION: artificial screening peptide

<400> SEQUENCE: 6

Cys Leu Leu Ala Gln Arg Gly Lys Lys Ser Asp Trp Lys His Asn Ile
1               5                   10                  15

Thr Gln

<210> SEQ ID NO 7
<211> LENGTH: 109
<212> TYPE: PRT
<213> ORGANISM: Mus musculus

<400> SEQUENCE: 7

Asp Ile Gln Leu Thr Gln Ser Pro Ala Ile Met Ala Ala Ser Leu Gly
1               5                   10                  15

Gln Lys Val Thr Met Thr Cys Ser Ala Ser Ser Ser Val Ser Ser Ser

```
                    20                  25                  30
Tyr Leu His Trp Tyr Gln Gln Lys Ser Gly Ala Ser Pro Lys Ser Leu
                35                  40                  45

Ile His Arg Thr Ser Asn Leu Ala Ser Gly Val Pro Ala Arg Phe Ser
        50                  55                  60

Gly Ser Gly Ser Gly Thr Ser Tyr Ser Leu Thr Ile Ser Ser Val Glu
65                  70                  75                  80

Ala Glu Asp Asp Ala Thr Tyr Tyr Cys Leu Gln Trp Ser Gly Phe Pro
                85                  90                  95

Phe Thr Phe Gly Ser Gly Thr Lys Leu Glu Ile Lys Arg
                100                 105
```

<210> SEQ ID NO 8
<211> LENGTH: 327
<212> TYPE: DNA
<213> ORGANISM: Artificial Sequence
<220> FEATURE:
<223> OTHER INFORMATION: derived from Mus musculus

<400> SEQUENCE: 8

```
gacattcagc tgacccagtc tccagcaata atggctgcct ctctggggca gaaggtcacc      60
atgacctgca gtgccagctc aagtgtaagt tccagttact tgcactggta ccagcagaag     120
tcaggcgctt cccccaaatc cttgattcat aggacatcca acctggcttc tggagtccca     180
gctcgcttca gtggcagtgg gtctgggacc tcttactctc tcacaatcag cagcgtggag     240
gctgaagatg atgcaactta ttactgcctg cagtggagtg gtttcccatt cacgttcggc     300
tcggggacca agctggagat caaacgt                                         327
```

<210> SEQ ID NO 9
<211> LENGTH: 12
<212> TYPE: PRT
<213> ORGANISM: Mus musculus

<400> SEQUENCE: 9

```
Ser Ala Ser Ser Ser Val Ser Ser Ser Tyr Leu His
1               5                   10
```

<210> SEQ ID NO 10
<211> LENGTH: 9
<212> TYPE: PRT
<213> ORGANISM: Mus musculus

<400> SEQUENCE: 10

```
Leu Gln Trp Ser Gly Phe Pro Phe Thr
1               5
```

<210> SEQ ID NO 11
<211> LENGTH: 117
<212> TYPE: PRT
<213> ORGANISM: Mus musculus

<400> SEQUENCE: 11

```
Gln Val Gln Leu Gln Glu Ser Gly Ala Ala Leu Val Arg Ser Gly Ala
1               5                   10                  15

Ser Val Lys Leu Ser Cys Thr Ala Ser Gly Phe Asn Ile Lys Asp Tyr
                20                  25                  30

Tyr Phe His Trp Val Lys Gln Arg Pro Asp Gln Gly Leu Glu Trp Ile
                35                  40                  45

Gly Trp Ile Asp Pro Glu Asn Gly Asp Thr Glu Tyr Ala Pro Asn Phe
```

| | | 50 | | | 55 | | | | 60 | | |
|---|---|---|---|---|---|---|---|---|---|---|---|
| Gln | Val | Lys | Ala | Thr | Met | Thr | Ala | Asp | Thr | Tyr | Ser | Asn | Thr | Ala | Tyr |
| 65 | | | | 70 | | | | 75 | | | | 80 |

Leu His Leu Ser Ser Leu Thr Ser Glu Asp Thr Ala Val Tyr Cys
                  85                    90                    95

Asn Ser Tyr Gly Asn Asn Tyr Phe Asp Tyr Trp Gly Gln Gly Thr Thr
            100                  105                  110

Val Thr Val Ser Ser
        115

<210> SEQ ID NO 12
<211> LENGTH: 351
<212> TYPE: DNA
<213> ORGANISM: Artificial Sequence
<220> FEATURE:
<223> OTHER INFORMATION: derived from Mus musculus

<400> SEQUENCE: 12

```
caggtccagc tgcaggagtc tggggcagcg cttgtgaggt caggggcctc agtcaaattg      60
tcctgcacag cttctggctt caacattaaa gactactatt ttcactgggt gaagcagagg     120
cctgaccagg gcctggagtg gattggatgg attgatcctg agaatggtga tactgaatat     180
gccccgaact tccaggtcaa ggccactatg actgcagaca catattccaa cacagcctac     240
ctgcatctca gcagcctgac atctgaggac actgccgtct attactgtaa ttcctacggt     300
aataactact ttgactactg gggccaaggg accacggtca ccgtctcctc a             351
```

<210> SEQ ID NO 13
<211> LENGTH: 10
<212> TYPE: PRT
<213> ORGANISM: Mus musculus

<400> SEQUENCE: 13

Gly Phe Asn Ile Lys Asp Tyr Tyr Phe His
1             5                  10

<210> SEQ ID NO 14
<211> LENGTH: 7
<212> TYPE: PRT
<213> ORGANISM: Mus musculus

<400> SEQUENCE: 14

Ala Pro Asn Phe Gln Val Lys
1             5

<210> SEQ ID NO 15
<211> LENGTH: 10
<212> TYPE: PRT
<213> ORGANISM: Mus musculus

<400> SEQUENCE: 15

Asn Ser Tyr Gly Asn Asn Tyr Phe Asp Tyr
1             5                  10

<210> SEQ ID NO 16
<211> LENGTH: 111
<212> TYPE: PRT
<213> ORGANISM: Mus musculus

<400> SEQUENCE: 16

Asp Ile Gln Leu Thr Gln Ser Pro Ser Thr Met Ala Ala Ser Pro Gly
1             5                  10                  15

Glu Lys Ile Thr Ile Thr Cys Ser Ala Ser Ser Ser Ile Ser Ser Asn
            20                  25                  30

Ser Leu His Trp Tyr Gln Gln Lys Pro Gly Phe Ser Pro Lys Leu Leu
        35                  40                  45

Ile Tyr Arg Thr Ser Asn Leu Ala Ser Gly Val Pro Gly Arg Phe Ser
    50                  55                  60

Gly Ser Gly Ser Gly Thr Ser Tyr Ser Leu Thr Ile Gly Thr Met Glu
65                  70                  75                  80

Thr Glu Asp Val Ala Thr Tyr Tyr Cys Gln Gln Gly Ser Ser Phe Pro
                85                  90                  95

Arg Met Leu Thr Phe Gly Thr Gly Thr Lys Leu Glu Ile Lys Arg
            100                 105                 110

<210> SEQ ID NO 17
<211> LENGTH: 111
<212> TYPE: PRT
<213> ORGANISM: Artificial Sequence
<220> FEATURE:
<223> OTHER INFORMATION: humanized

<400> SEQUENCE: 17

Asp Ile Gln Met Thr Gln Ser Pro Ser Ser Val Ser Ala Ser Val Gly
1               5                   10                  15

Asp Arg Val Thr Ile Thr Cys Arg Ala Ser Ser Ser Ile Ser Ser Asn
            20                  25                  30

Ser Leu His Trp Tyr Gln Gln Lys Pro Gly Lys Ala Pro Lys Leu Leu
        35                  40                  45

Ile Tyr Arg Thr Ser Ser Leu Gln Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys Gln Gln Gly Ser Ser Phe Pro
                85                  90                  95

Arg Met Leu Thr Phe Gly Gln Gly Thr Lys Leu Glu Ile Lys Arg
            100                 105                 110

<210> SEQ ID NO 18
<211> LENGTH: 111
<212> TYPE: PRT
<213> ORGANISM: Artificial Sequence
<220> FEATURE:
<223> OTHER INFORMATION: humanized

<400> SEQUENCE: 18

Asp Ile Gln Leu Thr Gln Ser Pro Ser Ser Val Ser Ala Ser Val Gly
1               5                   10                  15

Asp Arg Val Thr Ile Thr Cys Arg Ala Ser Ser Ser Ile Ser Ser Asn
            20                  25                  30

Ser Leu His Trp Tyr Gln Gln Lys Pro Gly Lys Ala Pro Lys Leu Leu
        35                  40                  45

Ile Tyr Arg Thr Ser Asn Leu Gln Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys Gln Gln Gly Ser Ser Phe Pro
                85                  90                  95

Arg Met Leu Thr Phe Gly Gln Gly Thr Lys Leu Glu Ile Lys Arg 100                 105                 110

<210> SEQ ID NO 19
<211> LENGTH: 111
<212> TYPE: PRT
<213> ORGANISM: Artificial Sequence
<220> FEATURE:
<223> OTHER INFORMATION: humanized

<400> SEQUENCE: 19

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Ser Ser Ile Ser Ser Asn
            20                  25                  30

Ser Leu His Trp Tyr Gln Gln Lys Pro Gly Gln Ala Pro Arg Leu Leu
        35                  40                  45

Ile Tyr Arg Thr Ser Asn Arg Ala Thr Gly Ile Pro Ala Arg Phe Ser
    50                  55                  60

Gly Ser Gly Ser Gly Thr Asp Tyr Thr Leu Thr Ile Ser Ser Leu Glu
65                  70                  75                  80

Pro Glu Asp Phe Ala Val Tyr Tyr Cys Gln Gln Gly Ser Ser Phe Pro
                85                  90                  95

Arg Met Leu Thr Phe Gly Gly Gly Thr Lys Val Glu Ile Lys Arg
            100                 105                 110

<210> SEQ ID NO 20
<211> LENGTH: 12
<212> TYPE: PRT
<213> ORGANISM: Artificial Sequence
<220> FEATURE:
<223> OTHER INFORMATION: humanized

<400> SEQUENCE: 20

Arg Ala Ser Ser Ser Ile Ser Ser Asn Ser Leu His
1               5                   10

<210> SEQ ID NO 21
<211> LENGTH: 7
<212> TYPE: PRT
<213> ORGANISM: Artificial Sequence
<220> FEATURE:
<223> OTHER INFORMATION: humanized

<400> SEQUENCE: 21

Arg Thr Ser Asn Leu Gln Ser
1               5

<210> SEQ ID NO 22
<211> LENGTH: 11
<212> TYPE: PRT
<213> ORGANISM: Artificial Sequence
<220> FEATURE:
<223> OTHER INFORMATION: HUMANIZED

<400> SEQUENCE: 22

Gln Gln Gly Ser Ser Phe Pro Arg Met Leu Thr
1               5                   10

<210> SEQ ID NO 23
<211> LENGTH: 7
<212> TYPE: PRT
<213> ORGANISM: Artificial Sequence
<220> FEATURE:
<223> OTHER INFORMATION: HUMANIZED

```
<400> SEQUENCE: 23

Arg Thr Ser Ser Leu Gln Ser
1               5

<210> SEQ ID NO 24
<211> LENGTH: 7
<212> TYPE: PRT
<213> ORGANISM: Artificial Sequence
<220> FEATURE:
<223> OTHER INFORMATION: HUMANIZED

<400> SEQUENCE: 24

Arg Thr Ser Asn Arg Ala Thr
1               5

<210> SEQ ID NO 25
<211> LENGTH: 12
<212> TYPE: PRT
<213> ORGANISM: Artificial Sequence
<220> FEATURE:
<223> OTHER INFORMATION: HUMANIZED

<400> SEQUENCE: 25

Ser Ala Ser Ser Ser Ile Ser Ser Asn Ser Leu His
1               5                   10

<210> SEQ ID NO 26
<211> LENGTH: 7
<212> TYPE: PRT
<213> ORGANISM: Mus musculus

<400> SEQUENCE: 26

Arg Thr Ser Asn Leu Ala Ser
1               5

<210> SEQ ID NO 27
<211> LENGTH: 117
<212> TYPE: PRT
<213> ORGANISM: Mus musculus

<400> SEQUENCE: 27

Gln Val Gln Leu Gln Glu Ser Gly Ala Glu Leu Val Arg Ser Gly Ala
1               5                   10                  15

Ser Val Lys Leu Ser Cys Thr Ala Ser Gly Phe Asn Ile Arg Asp Tyr
                20                  25                  30

Tyr Leu His Trp Ile Lys Gln Arg Pro Glu Gln Gly Leu Glu Trp Ile
            35                  40                  45

Gly Trp Ile Asp Pro Glu Asn Gly Asp Thr Glu Tyr Ala Pro Lys Phe
        50                  55                  60

Gln Asp Lys Ala Thr Val Thr Ala Asp Thr Ser Ser Asn Thr Ala Tyr
65                  70                  75                  80

Leu Gln Leu Asn Ser Leu Thr Ser Glu Asp Thr Ala Val Tyr Tyr Cys
                85                  90                  95

Asn Val Tyr Gly Ile Tyr Phe Met Asp Tyr Trp Gly Gln Gly Thr Thr
                100                 105                 110

Val Thr Val Ser Ser
            115

<210> SEQ ID NO 28
<211> LENGTH: 117
<212> TYPE: PRT
```

<213> ORGANISM: Artificial Sequence
<220> FEATURE:
<223> OTHER INFORMATION: HUMANIZED

<400> SEQUENCE: 28

```
Gln Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Arg Asp Tyr
            20                  25                  30

Tyr Leu His Trp Val Gln Gln Ala Pro Gly Lys Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Asn Val Tyr Gly Ile Tyr Phe Met Asp Tyr Trp Gly Gln Gly Thr Met
            100                 105                 110

Val Thr Val Ser Ser
        115
```

<210> SEQ ID NO 29
<211> LENGTH: 117
<212> TYPE: PRT
<213> ORGANISM: Artificial Sequence
<220> FEATURE:
<223> OTHER INFORMATION: HUMANIZED

<400> SEQUENCE: 29

```
Gln Val Gln Leu Val Gln Ser Gly Ala Glu Val Lys Lys Pro Gly Ala
1               5                   10                  15

Thr Val Lys Ile Ser Cys Lys Ala Ser Gly Phe Asn Ile Arg Asp Tyr
            20                  25                  30

Tyr Leu His Trp Val Gln Gln Ala Pro Gly Lys Gly Leu Glu Trp Met
        35                  40                  45

Gly Trp Ile Asp Pro Glu Asn Gly Asp Thr Glu Tyr Ala Pro Lys Phe
    50                  55                  60

Gln Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Asn Val Tyr Gly Ile Tyr Phe Met Asp Tyr Trp Gly Gln Gly Thr Met
            100                 105                 110

Val Thr Val Ser Ser
        115
```

<210> SEQ ID NO 30
<211> LENGTH: 117
<212> TYPE: PRT
<213> ORGANISM: Artificial Sequence
<220> FEATURE:
<223> OTHER INFORMATION: HUMANIZED

<400> SEQUENCE: 30

```
Gln Val Gln Leu Gln Glu Ser Gly Ala Glu Val Lys Lys Pro Gly Ala
1               5                   10                  15

Ser Val Lys Val Ser Cys Lys Ala Ser Gly Phe Asn Ile Arg Asp Tyr
            20                  25                  30
```

Tyr Leu His Trp Val Arg Gln Ala Pro Gly Gln Gly Leu Glu Trp Met
            35                  40                  45

Gly Trp Ile Asp Pro Glu Asn Gly Asp Thr Glu Tyr Ala Pro Lys Phe
        50                  55                  60

Gln Gly Arg Val Thr Thr Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Asn Val Tyr Gly Ile Tyr Phe Met Asp Tyr Trp Gly Gln Gly Thr Leu
            100                 105                 110

Val Thr Val Ser Ser
        115

<210> SEQ ID NO 31
<211> LENGTH: 10
<212> TYPE: PRT
<213> ORGANISM: Mus musculus

<400> SEQUENCE: 31

Gly Phe Asn Ile Arg Asp Tyr Tyr Leu His
1               5                   10

<210> SEQ ID NO 32
<211> LENGTH: 7
<212> TYPE: PRT
<213> ORGANISM: Artificial Sequence
<220> FEATURE:
<223> OTHER INFORMATION: HUMANIZED

<400> SEQUENCE: 32

Ala Pro Lys Phe Gln Gly Arg
1               5

<210> SEQ ID NO 33
<211> LENGTH: 10
<212> TYPE: PRT
<213> ORGANISM: Mus musculus

<400> SEQUENCE: 33

Asn Val Tyr Gly Ile Tyr Phe Met Asp Tyr
1               5                   10

<210> SEQ ID NO 34
<211> LENGTH: 7
<212> TYPE: PRT
<213> ORGANISM: Mus musculus

<400> SEQUENCE: 34

Ala Pro Lys Phe Gln Asp Lys
1               5

<210> SEQ ID NO 35
<211> LENGTH: 333
<212> TYPE: DNA
<213> ORGANISM: Artificial Sequence
<220> FEATURE:
<223> OTHER INFORMATION: derived from Mus musculus

<400> SEQUENCE: 35
gacattcagc tgacccagtc tccatccacc atggctgcat ctcccgggga gaagatcact      60
atcacctgca gtgccagctc aagtataagt tccaattcct tgcattggta tcagcagaag     120

| | |
|---|---|
| ccaggattct cccctaaact cttgatttat aggacatcca atctggcttc tggagtccca | 180 |
| ggtcgcttca gtggcagtgg gtctgggacc tcttactctc tcacaattgg caccatggag | 240 |
| actgaagatg ttgccactta ctactgccag cagggtagta gttttccacg catgctcacg | 300 |
| ttcggtactg ggaccaagct ggagatcaaa cgt | 333 |

<210> SEQ ID NO 36
<211> LENGTH: 333
<212> TYPE: DNA
<213> ORGANISM: Artificial Sequence
<220> FEATURE:
<223> OTHER INFORMATION: synthesized

<400> SEQUENCE: 36

| | |
|---|---|
| gacatccaga tgacccagtc cccctcctcc gtgtctgctt ctgtgggcga cagagtgaca | 60 |
| attacctgcc gggcctcctc ctccatctcc tccaattccc tgcactggta tcagcagaag | 120 |
| cccggcaagg cccccaagct gctgatctac cggacctcca gcctgcagtc cggcgtgccc | 180 |
| tctagattct ccggctctgg ctctggcacc gactataccc tgaccatctc cagcctgcag | 240 |
| cccgaggact cgccaccta ctactgtcag cagggctcct ccttccccg atgctgaca | 300 |
| tttggccagg gcaccaagct ggaaatcaag cgg | 333 |

<210> SEQ ID NO 37
<211> LENGTH: 333
<212> TYPE: DNA
<213> ORGANISM: Artificial Sequence
<220> FEATURE:
<223> OTHER INFORMATION: synthesized

<400> SEQUENCE: 37

| | |
|---|---|
| gacatccagc tgacccagtc cccctcctcc gtgtctgctt ctgtgggcga cagagtgaca | 60 |
| attacctgcc gggcctcctc ctccatctcc tccaattccc tgcactggta tcagcagaag | 120 |
| cccggcaagg cccccaagct gctgatctac cggacctcca acctgcagtc cggcgtgccc | 180 |
| tctagattct ccggctctgg ctctggcacc gactataccc tgaccatctc cagcctgcag | 240 |
| cccgaggact cgccaccta ctactgtcag cagggctcct ccttccccg atgctgaca | 300 |
| tttggccagg gcaccaagct ggaaatcaag cgg | 333 |

<210> SEQ ID NO 38
<211> LENGTH: 333
<212> TYPE: DNA
<213> ORGANISM: Artificial Sequence
<220> FEATURE:
<223> OTHER INFORMATION: synthesized

<400> SEQUENCE: 38

| | |
|---|---|
| gacatccaga tgacccagag ccctggcacc ctgtctctgt ctcccggcga gagagctacc | 60 |
| ctgtcctgca gagcctcctc ctccatctcc tccaattccc tgcactggta tcagcagaag | 120 |
| cccggccagg cccccagact gctgatctac cggacctcca tcgggccac ggcatccct | 180 |
| gccagattct ccggctctgg ctctggcacc gactataccc tgaccatctc cagcctggaa | 240 |
| cccgaggact tcgccgtgta ctactgtcag cagggctcct ccttccccg atgctgaca | 300 |
| tttggcggag gcaccaaggt ggaaatcaag cgg | 333 |

<210> SEQ ID NO 39
<211> LENGTH: 351
<212> TYPE: DNA
<213> ORGANISM: Artificial Sequence

```
<220> FEATURE:
<223> OTHER INFORMATION: derived from Mus musculus

<400> SEQUENCE: 39
caggtccagc tgcaggagtc tggggcagag cttgtgaggt caggggcctc agtcaagttg      60
tcctgcacag cttctggctt caacattaga gactactatt tgcactggat aaaacagagg     120
cctgaacagg gcctggagtg gattggatgg attgatcctg agaatggtga tactgaatat     180
gccccgaagt tccaggacaa ggccactgtg actgcagaca catcctccaa cacagcctac     240
ctgcagctca acagcctgac atctgaggac actgccgtct attactgtaa tgtatatggc     300
atctatttta tggactattg gggccaaggg accacggtca ccgtctcctc a              351

<210> SEQ ID NO 40
<211> LENGTH: 351
<212> TYPE: DNA
<213> ORGANISM: Artificial Sequence
<220> FEATURE:
<223> OTHER INFORMATION: synthesized

<400> SEQUENCE: 40
caggtgcagc tggtgcagtc tggcgccgaa gtgaagaaac tggcgctac cgtgaagatc       60 tcctgcaagg tgtccggctt caacatccgg gactactacc tgcactgggt gcagcaggcc    120
cctggcaagg gactggaatg gatgggctgg atcgaccccg agaacggcga taccgagtac    180
gcccctaagt tccagggcag agtgaccatc accgccgaca cctctaccga caccgcctac    240
atggaactgt cctccctgcg gagcgaggac accgccgtgt actactgcaa cgtgtacggc    300
atctacttca tggactactg gggccagggc acaatggtca ccgtgtcctc t              351

<210> SEQ ID NO 41
<211> LENGTH: 351
<212> TYPE: DNA
<213> ORGANISM: Artificial Sequence
<220> FEATURE:
<223> OTHER INFORMATION: synthesized

<400> SEQUENCE: 41
caggtgcagc tggtgcagtc tggcgccgaa gtgaagaaac tggcgctac cgtgaagatc       60 tcctgcaagg cctccggctt caacatccgg gactactacc tgcactgggt gcagcaggcc    120
cctggcaagg gactggaatg gatgggctgg atcgaccccg agaacggcga taccgagtac    180
gcccctaagt tccagggcag agtgaccatc accgccgaca cctctaccaa caccgcctac    240
atggaactgt cctccctgcg gagcgaggac accgccgtgt actactgcaa cgtgtacggc    300
atctacttca tggactactg gggccagggc acaatggtca ccgtgtcctc t              351

<210> SEQ ID NO 42
<211> LENGTH: 351
<212> TYPE: DNA
<213> ORGANISM: Artificial Sequence
<220> FEATURE:
<223> OTHER INFORMATION: synthesized

<400> SEQUENCE: 42
caggtgcagc tgcaggaatc tggcgccgaa gtgaagaaac tggcgcctc cgtgaaggtg       60 tcctgcaagg cctccggctt caacatccgg gactactacc tgcactgggt gcgacaggct    120
ccaggccagg gactggaatg gatgggctgg atcgaccccg agaacggcga taccgagtac    180
gcccctaagt tccagggcag agtgaccacc accgccgaca cctctatctc caccgcctac    240
```

```
atggaactgt cccggctgag atccgacgac accgccgtgt actactgcaa cgtgtacggc    300
atctacttca tggactactg gggccagggc acactcgtca ccgtgtcctc t             351
```

<210> SEQ ID NO 43
<211> LENGTH: 46
<212> TYPE: DNA
<213> ORGANISM: Artificial Sequence
<220> FEATURE:
<223> OTHER INFORMATION: primer

<400> SEQUENCE: 43

```
cagtcgaagc tttgaggaga cggtgaccgt ggtcccttgg ccccag                    46
```

<210> SEQ ID NO 44
<211> LENGTH: 34
<212> TYPE: DNA
<213> ORGANISM: Artificial Sequence
<220> FEATURE:
<223> OTHER INFORMATION: primer

<400> SEQUENCE: 44

```
caactaggat ccaggtsmar ctgcagsagt cwgg                                 34
```

<210> SEQ ID NO 45
<211> LENGTH: 6
<212> TYPE: DNA
<213> ORGANISM: Artificial Sequence
<220> FEATURE:
<223> OTHER INFORMATION: primer

<400> SEQUENCE: 45

```
aagctt                                                                6
```

<210> SEQ ID NO 46
<211> LENGTH: 6
<212> TYPE: DNA
<213> ORGANISM: Artificial Sequence
<220> FEATURE:
<223> OTHER INFORMATION: primer

<400> SEQUENCE: 46

```
ggatcc                                                                6
```

<210> SEQ ID NO 47
<211> LENGTH: 34
<212> TYPE: DNA
<213> ORGANISM: Artificial Sequence
<220> FEATURE:
<223> OTHER INFORMATION: primer

<400> SEQUENCE: 47

```
cagtcgaagc ttgttagatc tccagcttgg tccc                                 34
```

<210> SEQ ID NO 48
<211> LENGTH: 36
<212> TYPE: DNA
<213> ORGANISM: Artificial Sequence
<220> FEATURE:
<223> OTHER INFORMATION: primer

<400> SEQUENCE: 48

```
caactaggat ccgacattca gctgacccag tctcca                               36
```

<210> SEQ ID NO 49
<211> LENGTH: 30

<212> TYPE: DNA
<213> ORGANISM: Artificial Sequence
<220> FEATURE:
<223> OTHER INFORMATION: primer

<400> SEQUENCE: 49
tcacgaattc tcaggtccag ctgcaggagt					30

<210> SEQ ID NO 50
<211> LENGTH: 29
<212> TYPE: DNA
<213> ORGANISM: Artificial Sequence
<220> FEATURE:
<223> OTHER INFORMATION: primer

<400> SEQUENCE: 50
ttggtgctag ctgaggagac ggtgaccgt					29

<210> SEQ ID NO 51
<211> LENGTH: 6
<212> TYPE: DNA
<213> ORGANISM: Artificial Sequence
<220> FEATURE:
<223> OTHER INFORMATION: primer

<400> SEQUENCE: 51 gaattc					6

<210> SEQ ID NO 52
<211> LENGTH: 6
<212> TYPE: DNA
<213> ORGANISM: Artificial Sequence
<220> FEATURE:
<223> OTHER INFORMATION: primer

<400> SEQUENCE: 52 gctagc					6

<210> SEQ ID NO 53
<211> LENGTH: 34
<212> TYPE: DNA
<213> ORGANISM: Artificial Sequence
<220> FEATURE:
<223> OTHER INFORMATION: primer

<400> SEQUENCE: 53
agccaccgta cgtttgatct ccagcttggt ccca					34

<210> SEQ ID NO 54
<211> LENGTH: 6
<212> TYPE: DNA
<213> ORGANISM: Artificial Sequence
<220> FEATURE:
<223> OTHER INFORMATION: primer

<400> SEQUENCE: 54 cgtacg					6

<210> SEQ ID NO 55
<211> LENGTH: 30
<212> TYPE: DNA

```
<213> ORGANISM: Artificial Sequence
<220> FEATURE:
<223> OTHER INFORMATION: primer

<400> SEQUENCE: 55
gtcacgaatt cagacattca gctgacccag                                              30
```

COMPOSITIONS AND METHODS FOR TREATING OBESITY AND HYPERPHAGIA

CROSS-REFERENCE TO RELATED APPLICATIONS

This application is a divisional of U.S. patent application Ser. No. 15/714,552, filed Sep. 25, 2017, now U.S. Pat. No. 10,548,951, which claimed priority to U.S. Provisional Patent Application Ser. No. 62/527,968, filed on Jun. 30, 2017, and to U.S. Provisional Patent Application Ser. No. 62/428,982, filed on Dec. 1, 2016, and was also a continuation-in-part of U.S. patent application Ser. No. 14/573,600, filed Dec. 17, 2014, now U.S. Pat. No. 9,771,422, which claimed priority to U.S. Provisional Patent Application Ser. No. 61/917,136, filed on Dec. 17, 2013; to U.S. Provisional Patent Application Ser. No. 61/974,660, filed on Apr. 3, 2014; to U.S. Provisional Patent Application Ser. No. 62/007,255, filed on Jun. 3, 2014; to U.S. Provisional Patent Application Ser. No. 62/045,189, filed on Sep. 3, 2014; to U.S. Provisional Patent Application Ser. No. 62/074,225, filed on Nov. 3, 2014; to U.S. Provisional Patent Application Ser. No. 62/074,227, filed on Nov. 3, 2014; and to U.S. Provisional Patent Application Ser. No. 62/074,234, filed on Nov. 3, 2014. The disclosures of these applications are fully incorporated by reference herein.

BACKGROUND

A sequence listing is being submitted herein as an ASCII text file with the name "MHMS200014US01_ST25.txt", created on Dec. 17, 2014, with a file size of 24,995 bytes. The material in this text file is hereby fully incorporated by reference herein.

The present disclosure relates, in various exemplary embodiments, generally to compositions and methods inducing weight loss or for treating weight gain in persons that have genetic disorders characterized by hyperphagia using molecular antagonists, such as monoclonal antibodies (mAbs), that bind to glucose-dependent insulinotropic polypeptide (GIP). Fatty tissue buildup occurs in several different diseases or conditions, which can be treated using such antagonists/monoclonal antibodies. This disclosure also relates to treatment of such diseases or conditions by improving glucose tolerance without needing increased serum insulin by administration of such antagonists/monoclonal antibodies. Hyperphagia, or an abnormally increased appetite, is a central feature of certain genetic disorders, and can be treated using such antagonists/monoclonal antibodies.

Obesity is a medical condition in which excess body fat has accumulated to the extent that it has a negative effect on health. In the United States, obesity is considered to occur when a person's body mass index (BMI), calculated by dividing the person's weight by the square of the person's height, is 30 kg/m$^2$ or greater. Obesity can arise from a combination of factors including excessive caloric intake, unhealthy diet, lack of physical activity, genetics, age, and lack of sleep. Obesity increases the likelihood of various diseases, including heart disease, type 2 diabetes, obstructive sleep apnea, some cancers, and osteoarthritis.

Metabolic syndrome is diagnosed when three of the five following medical conditions are diagnosed together: increased blood pressure, excess body fat around the waist, high fasting blood glucose, high serum triglycerides, and low high-density cholesterol (HDL) levels. Metabolic syndrome also increases the risk of diseases including type 2 diabetes, coronary heart disease, lipodystrophy, and potentially some psychiatric illnesses. Treatment includes changes in lifestyle and medication.

Hyperlipidemia is a condition in which the levels of lipids and/or lipoproteins in the blood are abnormally elevated. Primary hyperlipidemia is usually due to genetic causes, while secondary hyperlipidemia arises from other underlying factors such as diabetes mellitus, the use of certain drugs, and alcohol consumption. Hyperlipidemia can be divided into hypercholesterolemia and hypertriglyceridemia. Hypercholesterolemia is generally diagnosed in the United States when the total cholesterol level is greater than 240 mg/dl. Hypertriglyceridemia is usually diagnosed in the United States when triglyceride levels are higher than 500 mg/dl.

Non-insulin dependent (Type II) diabetes mellitus occurs when the cells of the body do not respond properly to insulin, a condition known as insulin resistance. As a result, high blood sugar levels persist over a prolonged period. The primary cause is excessive body weight and insufficient exercise. Long-term complications can include cardiovascular disease, stroke, kidney failure, and eye damage.

Cushing's syndrome is associated with prolonged exposure to abnormally high levels of the hormone cortisol. Cortisol is produced in the adrenal glands, and is usually induced by corticotropin. However, food-induced Cushing's syndrome occurs when the adrenal glands are abnormally responsive to gastric inhibitory polypeptide (GIP).

Fatty liver disease (FLD) is a global chronic health problem that occurs in both adults and children. Clinically categorized FLD falls into two broad groups: nonalcoholic FLD (NAFLD) and alcoholic FLD (AFLD). NAFLD and AFLD are characterized by a liver fat content exceeding 5-10%, the only distinguishing factor being the underlying cause of the disease. However, it is generally difficult to distinguish between the two classes of FLD based on morphological characteristics alone. Generally, FLD occurs in those who consume excessive amounts of alcohol, those who may have metabolic disorders or genetic predispositions that influence fatty acid metabolism, and/or those who are obese. Common co-morbidities include obesity, type 2 (non-insulin dependent) diabetes mellitus, and hyperlipidemia.

The core pathologies of FLD include hepatic steatosis and steatohepatitis with progression to cirrhosis. Steatosis occurs when lipid content in the liver exceeds 5-10% in weight, indicating an abnormal retention of lipid vesicles and inhibition of fatty acid oxidation. Steatosis is considered reversible, provided the underlying cause of the disease is identified and resolved.

Should steatosis persist, it may evolve into nonalcoholic steatohepatitis (NASH) or alcoholic steatohepatitis (ASH), depending on the severity and the inciting cause. Unlike steatosis, NASH and ASH are not reversible, only treatable. These are characterized by more fat accumulation, mixed lobular inflammation, ballooning degeneration of hepatocytes, glycogenated hepatocyte nuclei, and pericellular fibrosis. They may progress to cirrhosis and eventually liver cancer.

Current therapies for FLD include (1) following a reasonable diet and exercise plan, (2) avoiding worsening liver damage that may occur through sudden weight loss or drug abuse, (3) reducing weight, (4) taking insulin-sensitizing agents to decrease insulin resistance and to control blood glucose, (5) using blood lipid lowering drugs or drugs for ameliorating liver disease, and (6) seeking liver transplantation.

Obesity is also a primary phenotypic component of hyperphagia, which can arise from certain disorders. These include Prader-Willi syndrome, Kleine-Levin syndrome, Bardet-Biedl syndrome, and Graves' disease. Hyperphagia is also a symptom of other conditions, such as tumors in the hypothalamus or the frontal lobe or the temporal lobe; Kluver-Bucy syndrome; Pick's disease; Huntington's chorea; Parkinson's disease; diabetes; and hyperthyroidism.

In a clinical setting, appetite suppressants work in part by producing nausea. Thus, one may lose weight if s/he is willing to feel ill during the process. Such a side effect is not desirable, particularly with regard to asking a patient to maintain compliance with a weight loss regimen. Currently available appetite suppressants, such as GLP-1 analogs (like exenatide or liraglutide), have been unable to successfully overcome hyperphagia, and thus have been ineffective in treating the disorders and conditions described above (such as Prader-Willi syndrome).

Additional therapies against FLD and other diseases involving fat buildup are desirable, and particularly therapies that can result in weight loss. Additional therapies for treating disorders characterized by hyperphagia would also be desirable.

BRIEF SUMMARY OF THE DISCLOSURE

The present disclosure is directed to monoclonal antibodies (mAbs) that bind to gastric inhibitory polypeptide (GIP), also known as glucose-dependent insulinotropic polypeptide, and to methods of using such mAbs to treat diseases involving the buildup of fat in tissue or hyperphagia. Such hyperphagic diseases, disorders, and conditions may include Prader-Willi syndrome; Kleine-Levin syndrome; Bardet-Biedl syndrome; Graves' disease; tumors in the hypothalamus or the frontal lobe or the temporal lobe; Kluver-Bucy syndrome; Pick's disease; Huntington's chorea; Parkinson's disease; diabetes; and hyperthyroidism.

Disclosed herein in various embodiments are methods of inducing weight loss or of treating hyperphagia. These methods may be applicable to several different diseases or conditions. These methods all comprise administering to a person a composition comprising a pharmaceutically effective amount of a molecular antagonist of gastric inhibitory polypeptide (GIP).

The molecular antagonist comprises at least one complementarity determining region (CDR) with at least 80% identity to an amino acid sequence selected from the group consisting of SEQ ID NO: 20, SEQ ID NO: 21, SEQ ID NO: 22, SEQ ID NO: 23, SEQ ID NO: 24, SEQ ID NO: 31, SEQ ID NO: 32, and SEQ ID NO: 33.

In specific embodiments, the molecular antagonist comprises a light chain variable domain having a first CDR and a second CDR, each CDR having at least 95% identity to an amino acid sequence selected from the group consisting of SEQ ID NO: 20, SEQ ID NO: 21, SEQ ID NO: 22, SEQ ID NO: 23, and SEQ ID NO: 24. The first CDR and the second CDR of the molecular antagonist are joined to each other by a linking group. The linking group can be a chain of amino acids.

In other embodiments, the molecular antagonist comprises a light chain variable domain having a first CDR with at least 80% identity to the amino acid sequence of SEQ ID NO: 20, a second CDR with at least 80% identity to the amino acid sequence of SEQ ID NO: 21, and a third CDR with at least 85% identity to the amino acid sequence of SEQ ID NO: 22. The first CDR, the second CDR, and the third CDR of the molecular antagonist are joined to each other by linking groups. The linking groups can be independently a chain of amino acids.

In still other embodiments, the molecular antagonist comprises a light chain variable domain having at least 80% identity to an amino acid sequence selected from the group consisting of SEQ ID NO: 16, SEQ ID NO: 17, SEQ ID NO: 18, and SEQ ID NO: 19.

In yet still more embodiments, the molecular antagonist comprises a heavy chain variable domain having a first CDR with at least 80% identity to the amino acid sequence of SEQ ID NO: 31, a second CDR with at least 80% identity to the amino acid sequence of SEQ ID NO: 32, and a third CDR with at least 80% identity to the amino acid sequence of SEQ ID NO: 33.

In some embodiments, the molecular antagonist comprises a heavy chain variable domain having at least 80% identity to an amino acid sequence selected from the group consisting of SEQ ID NO: 27, SEQ ID NO: 28, SEQ ID NO: 29, and SEQ ID NO: 30.

In particular embodiments, the molecular antagonist comprises a light chain variable domain and a heavy chain variable domain; wherein the light chain variable domain comprises a first CDR and a second CDR, each CDR having at least 95% identity to an amino acid sequence selected from the group consisting of SEQ ID NO: 20, SEQ ID NO: 21, SEQ ID NO: 22, SEQ ID NO: 23, and SEQ ID NO: 24; and wherein the heavy chain variable domain comprises a first CDR with at least 80% identity to the amino acid sequence of SEQ ID NO: 31, a second CDR with at least 80% identity to the amino acid sequence of SEQ ID NO: 32, and a third CDR with at least 80% identity to the amino acid sequence of SEQ ID NO: 33. The molecular antagonist can be a single-chain variable fragment (scFv), an F(ab')$_2$ fragment, a Fab or Fab' fragment, a diabody, a triabody, a tetrabody, or a monoclonal antibody.

In other embodiments, the molecular antagonist comprises a light chain variable domain and a heavy chain variable domain; wherein the light chain variable domain has at least 80% identity to an amino acid sequence selected from the group consisting of SEQ ID NO: 16, SEQ ID NO: 17, SEQ ID NO: 18, and SEQ ID NO: 19; and wherein the heavy chain variable domain has at least 80% identity to an amino acid sequence selected from the group consisting of SEQ ID NO: 27, SEQ ID NO: 28, SEQ ID NO: 29, and SEQ ID NO: 30. The molecular antagonist can be a single-chain variable fragment (scFv), an F(ab')$_2$ fragment, a Fab or Fab' fragment, a diabody, a triabody, a tetrabody, or a monoclonal antibody.

In specific embodiments, the molecular antagonist is a monoclonal antibody with a light chain variable domain having at least 80% identity to SEQ ID NO: 18, and a heavy chain variable domain having at least 80% identity to an amino acid sequence selected from the group consisting of SEQ ID NO: 28, SEQ ID NO: 29, and SEQ ID NO: 30.

In more specific embodiments, the molecular antagonist is a whole monoclonal antibody with a light chain variable domain having at least 90% identity to SEQ ID NO: 18, and a heavy chain variable domain having at least 90% identity to SEQ ID NO: 29.

The molecular antagonist may bind to an amino acid sequence of GIP, the amino acid sequence being selected from the group consisting of SEQ ID NO: 1, SEQ ID NO: 2, SEQ ID NO: 3, and SEQ ID NO: 4.

In particular embodiments, the molecular antagonist is a whole monoclonal antibody comprising human constant regions.

The molecular antagonist may have a MW of about 30 kDa to about 500 kDa. The molecular antagonist may have a binding affinity for GIP characterized by an $IC_{50}$ of about 0.1 nM to about 7 nM.

The composition can be administered intravenously, intraperitoneally, or subcutaneously. The composition can further comprise an inert pharmaceutical excipient selected from the group consisting of buffering agents, surfactants, preservative agents, bulking agents, polymers, and stabilizers. The composition may be in the form of a powder, injection, solution, suspension, or emulsion.

The composition may contain the monoclonal antibody antagonist in an amount of from about 0.1 to about 1000 milligram per milliliter of the composition. Sometimes, the composition is lyophilized.

Also disclosed herein are molecular antagonists of gastric inhibitory polypeptide (GIP), which can take several forms such as whole monoclonal antibodies and variants thereof. The molecular antagonists are as described above.

Also disclosed herein are complementary DNA sequences having at least 85% identity to a DNA sequence selected from the group consisting of SEQ ID NO: 35, SEQ ID NO: 36, SEQ ID NO: 37, SEQ ID NO: 38, SEQ ID NO: 39, SEQ ID NO: 40, SEQ ID NO: 41, and SEQ ID NO: 42.

These and other non-limiting features of the present disclosure are discussed in more detail below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following is a brief description of the drawings, which are presented for the purposes of illustrating the exemplary embodiments disclosed herein and not for the purposes of limiting the same.

DETAILED DESCRIPTION

Figure 1A:
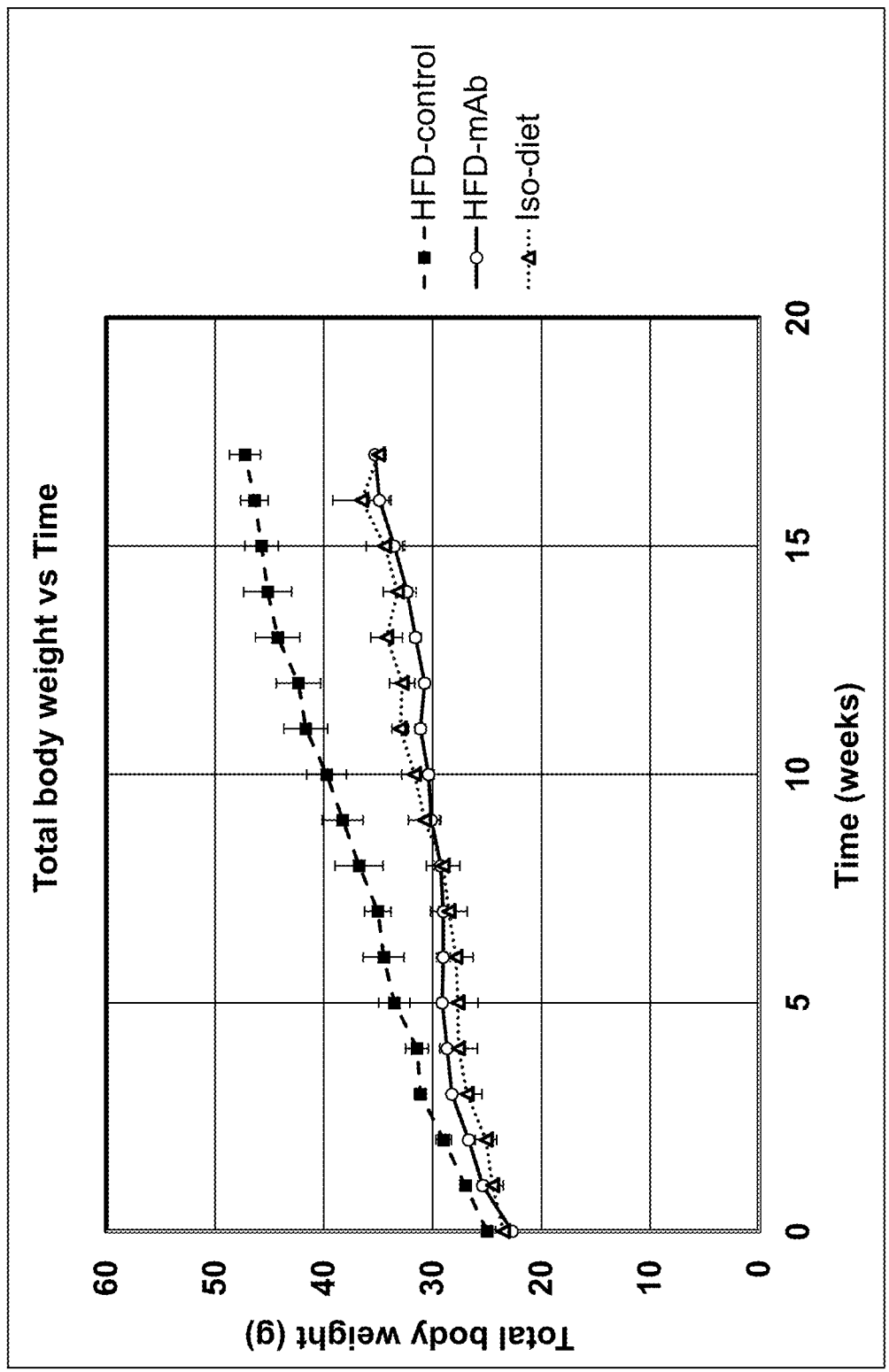
FIG. 1A is a graph showing the body weight of mice versus time for three different sets of mice over a 17-week study period. C57BL/6 mice fed a high-fat diet are an established model of diet-induced obesity and associated metabolic syndrome. The "HFD-control" mice were fed a high-fat diet (HFD) and administered phosphate buffered saline (PBS) by intraperitoneal injection. The "HFD-mAb" mice were fed a HFD diet and administered, by intraperitoneal injection, the monoclonal antibody antagonist of gastric inhibitory polypeptide (GIP mAb) in PBS at 60 mg/kg body weight (BW) per week. The "Iso-diet" mice were fed a low-fat isocaloric diet and not treated. In the HFD diet, about 60% of total calories come from fat, while in the isocaloric diet, about 10% of total calories come from fat. Mice administered the GIP mAb gained weight much less quickly. The HFD-control mice had an average weight gain of 21.5±1.0 grams over the 17 week study period. The HFD-mAb mice had an average weight gain of 11.5±0.5 grams over the 17 week study period. The difference in weight gain between these two groups was significant with a p-value of 0.00000007.

The singular forms "a," "an," and "the" include plural referents unless the context clearly dictates otherwise.

As used in the specification and in the claims, the open-ended transitional phrases "comprise(s)," "include(s)," "having," "contain(s)," and variants thereof require the presence of the named ingredients/steps and permit the presence of other ingredients/steps. These phrases should also be construed as disclosing the closed-ended phrases "consist of" or "consist essentially of" that permit only the named ingredients/steps and unavoidable impurities, and exclude other ingredients/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

The term "about" can be used to include any numerical value that can vary without changing the basic function of that value. When used with a range, "about" also discloses the range defined by the absolute values of the two endpoints, e.g. "about 2 to about 4" also discloses the range "from 2 to 4." The term "about" may refer to plus or minus 10% of the indicated number.

The term "identity" refers to the similarity between a pair of sequences (nucleotide or amino acid). Identity is measured by dividing the number of identical residues by the total number of residues and multiplying the product by 100 to achieve a percentage. Thus, two copies of exactly the same sequence have 100% identity, while sequences that have deletions, additions, or substitutions may have a lower degree of identity. Those skilled in the art will recognize that several computer programs, such as those that employ algorithms such as BLAST, are available for determining sequence identity. BLAST nucleotide searches are performed with the NBLAST program, and BLAST protein searches are performed with the BLASTP program, using the default parameters of the respective programs.

Two different sequences may vary from each other without affecting the overall function of the protein encoded by the sequence. In this regard, it is well known in the art that chemically similar amino acids can replace each other, often without change in function. Relevant properties can include acidic/basic, polar/nonpolar, electrical charge, hydrophobicity, and chemical structure. For example, the basic residues Lys and Arg are considered chemically similar and often replace each other, as do the acidic residues Asp and Glu, the hydroxyl residues Ser and Thr, the aromatic residues Tyr, Phe and Trp, and the non-polar residues Ala, Val, Ile, Leu and Met. These substitutions are considered to be "conserved."

For purposes of the present disclosure, when comparing amino acid sequences for % identity, any deletions will only occur at the ends of the amino acid sequences, and not in the middle of the sequence. Also, for purposes of the present disclosure, the following seven groups of amino acids are considered to be conservative substitutions with each other (cysteine and proline have no conservative substitutions) when determining % identity:

Cysteine (C)
Proline (P)
Valine, isoleucine, leucine, methionine, alanine, glycine (V, I, L, M, A, G)
Histidine, lysine, arginine (H, K, R)
Phenylalanine, tryptophan, tyrosine (F, W, Y)
Serine, threonine, asparagine, glutamine (S, T, N, Q)
Aspartic acid, glutamic acid (D, E)

Similarly, nucleotide codons and acceptable variations are known in the art. For example, the codons ACT, ACC, ACA, and ACG all code for the amino acid threonine, i.e. the third nucleotide can be modified without changing the resulting amino acid. Similarity is measured by dividing the number of similar residues by the total number of residues and multiplying the product by 100 to achieve a percentage. Note that similarity and identity measure different properties.

An "antibody" is a protein used by the immune system to identify a target antigen. The basic functional unit of an antibody is an immunoglobulin monomer. The monomer is made up of two identical heavy chains and two identical light chains which form a Y-shaped protein. Each light chain is composed of one constant domain and one variable domain. For light chains, the constant domain may also be referred to as the "constant region", and the variable domain can also be referred to as the "variable region". Each heavy chain is composed of one variable domain and three or four constant domains. For heavy chains, the constant domains together are referred to as the "constant region", and the variable domain can also be referred to as the "variable region". The arms of the Y are called the fragment, antigen-binding (Fab) region, with each arm being called a Fab fragment. Each Fab fragment is composed of one constant domain and one variable domain from a heavy chain, and one constant domain and one variable domain from a light chain. The base of the Y is called the Fc region, and is composed of two or three constant domains from each heavy chain. The variable domains of the heavy and light chains in the Fab region are the part of the antibody that binds to GIP. More specifically, the complementarity determining regions (CDRs) of the variable domains bind to their antigen (i.e. the GIP). In the amino acid sequence of each variable domain, there are three CDRs arranged non-consecutively. The term "whole" is used herein to refer to an antibody that contains the Fab region and the Fc region.

An "antagonist of GIP" according to the present disclosure is a molecule that binds to GIP and interferes with the biological action of GIP.

The present disclosure relates to methods of treating patients with molecules that antagonize GIP, i.e. bind to GIP. In this regard, glucose-dependent insulinotropic polypeptide, also referred to as gastric inhibitory polypeptide or GIP, is an insulinotropic peptide released from intestinal K-cells during the postprandial period. As an incretin, GIP stimulates insulin secretion by stimulating pancreatic beta cells in response to food intake. GIP, also notated herein as GIP(1-42), primarily circulates as a 42-amino acid polypeptide, but is also present in a form lacking the first 2 N-terminal amino acids (GIP(3-42)). GIP(1-30)-$NH_2$ or GIP(1-30)-alpha amide is a synthetic derivative of GIP(1-42) that lacks the last 12 C-terminal amino acids. GIP(1-30)-$NH_2$ has the same biological functions as GIP(1-42). Naturally occurring GIP (1-30)-$NH_2$ has been hypothesized, but has not been identified in any biological species.

GIP functions via binding to its cognate receptor (GIPR) found on the surface of target cells. GIPR is a member of the glucagon-secretin family of G-protein coupled receptors (GPCRs), possessing seven transmembrane domains. Native GIP(1-42) and the synthetic derivative GIP(1-30)-$NH_2$ bind to GIPR with high affinity and possess agonist properties. GIP receptors are also expressed in adipocytes, which respond to increased GIP levels with increased glucose uptake, fatty acid synthesis, and fatty acid incorporation into lipids within adipocytes. Native GIP(1-42) and the synthetic derivative GIP(1-30)-$NH_2$ also inhibit lipolysis in adipocytes induced by glucagon and β-adrenergic receptor agonists, including isoproterenol.

GIP is well-conserved between humans (*Homo sapiens*) (SEQ ID NO: 1), mice (*Mus musculus*) (SEQ ID NO: 2), rats (*Rattus norvegicus*) (SEQ ID NO: 3), and pigs (*Sus scrofa*) (SEQ ID NO: 4). There are only four substitutions between the four sequences, all of which are conserved. The 42-amino acid sequences from these four species are listed below:

```
SEQ ID NO: 1:
YAEGT FISDY SIAMD KIHQQ DFVNW LLAQK GKKND WKHNI TQ

SEQ ID NO: 2:
YAEGT FISDY SIAMD KIRQQ DFVNW LLAQR GKKSD WKHNI TQ

SEQ ID NO: 3:
YAEGT FISDY SIAMD KIRQQ DFVNW LLAQK GKKND WKHNL TQ

SEQ ID NO: 4:
YAEGT FISDY SIAMD KIRQQ DFVNW LLAQK GKKSD WKHNI TQ
```

The present application relates to methods of treating fatty tissue buildup, inducing weight loss, or hyperphagia, as well as diseases, disorders and conditions characterized by these three conditions, using compositions containing molecular antagonists that bind to GIP. In particular embodiments, the molecular antagonists are whole monoclonal antibodies (i.e. GIP mAbs). It is known that following oral glucose administration, serum GIP levels increase 5- to 6-fold, which stimulates insulin release, which promotes glucose uptake. GIP also activates Akt/PKB, which promotes the membrane translocation of glucose transporter-4, leading to enhanced adipocyte uptake of glucose, leading to the creation and storage of fat. As a result, it was hypothesized that antagonizing GIP and reducing its biological activity would inhibit glucose absorption and thus lead to reduced creation and storage of fat.

The present disclosure shows that fat retention in the liver, the omentum, or the subcutaneous tissue can be reduced, and that the degree of obesity can be reduced, or weight loss can be induced, by administering a composition comprising a GIP monoclonal antibody antagonist to a patient, for the same amount of caloric intake. Other molecular antagonists which are variations on the CDRs of the monoclonal antibody can also be effective in reducing weight gain in disorders characterized by hyperphagia. Desirably, the weight loss described herein can reverse obesity.

The GIP molecular antagonists described herein can also be helpful in ameliorating other diseases or conditions that can be treated by reducing GIP expression or by reducing caloric uptake or losing weight, such as obesity, metabolic syndrome, hyperlipidemia, type II diabetes, and food-induced Cushing's syndrome. The weight loss described herein can be used to reverse obesity.

GIP monoclonal antibody antagonists of the present disclosure can be generated and screened in the following manner. Two peptides with the following amino acid sequences were chemically synthesized:

```
GIP(1-17) + C:
YAEGT FISDY SIAMD KIC      (SEQ ID NO: 5)

C + mGIP(26-42):
CLLAQ RGKKS DWKHN ITQ      (SEQ ID NO: 6)
```

The amino acid sequence of GIP(1-17)+C corresponds to the first 17 amino acids commonly shared by mature human, mouse, rat, and pig GIP. The sequence also contains an extra cysteine residue at the N-terminus to facilitate conjugation to keyhole limpet hemocyanin (KLH). The amino acid sequence of C+mGIP(26-42) corresponds to the last 17 amino acids of mature mouse GIP, which has only two substitutions when compared separately to human GIP or porcine GIP, and only three substitutions when compared to rat GIP. The sequence also contains an extra cysteine residue at the C-terminus to facilitate conjugation to KLH. The two peptides were conjugated to KLH. Each conjugate was then used separately to inject a group of four mice at four different occasions. Mice were injected at weeks 1, 4, 7, 10 and 24 before spleens were harvested.

The spleens were removed from the immunized mice, and splenocytes were isolated before B cells were fused with immortalized myeloma cells in vitro. Polyethylene glycol (PEG) was included in the fusion process to increase efficiency. Fused cells or hybridomas were incubated in hypoxanthine-aminopterin-thymidine (HAT) medium for 14 days to kill myeloma cells that did not fuse with B cells. The hybridoma cells were then diluted with incubation media and transferred to a series of 96-well plates. The dilutions were to the extent that each well contained approximately one cell. The hybridoma cells were expanded several days before conditioned media or supernate was collected for screening purposes.

96-well plates were coated with synthetic mouse GIP(1-42) (Phoenix Pharmaceuticals) using 50 µl of a 4 µg/ml solution in PBS. The hybridoma supernates were then collected and added to the wells containing mouse GIP(1-42) for 4 hours at 37° C. The supernates were then removed and washed to remove any antibody not bound to mouse GIP. Next, a solution of goat anti-mouse IgG conjugated with horseradish peroxidase (HRP) was added to the wells. The goat anti-mouse IgG-HRP was obtained from Jackson Laboratories and used at a dilution of 1 part per 5000. After incubation for 1 hour at 37° C., the antibody solution was removed, and the wells were washed 2 times with 0.4 mg/ml BSA in PBS.

A solution containing HRP substrate 4 mg/ml o-Phenylenediamine dihydrochloride (OPO) in 0.4 mg/ml urea hydrogen peroxide and 0.05 M phosphate-citrate, pH 5.0, was then added to each well. To quantify HRP activity, the absorbance of light at a wavelength of 490 nm for each well was measured using an ELISA plate reader. This allowed hybridomas to be identified that generated monoclonal antibodies which would bind to the mouse GIP in the wells.

Next, supernates from those identified hybridomas were subsequently mixed with a 4 µg/ml solution of mouse GIP for 30 minutes at 37° C., then added to wells coated with mouse GIP as described above. After incubation for 1 hour at 37° C., the wells were washed, and goat anti-mouse IgG-HRP was added to the wells. After incubation for 1 hour, the samples were washed and a solution containing the HRP substrate 4 mg/ml OPO in 0.4 mg/ml urea hydrogen peroxide, and 0.05 M phosphate-citrate, pH 5.0, was added to each well. HRP activity in each well was quantified. In this screen, monoclonal antibodies that bound to GIP in suspension would be "neutralized" and would not be able to bind to the GIP fixed in the wells. Therefore, wells with low HRP activity corresponded to monoclonal antibodies that bound more effectively to GIP in suspension. Using these criteria, five hybridomas were identified that best generated monoclonal antibodies (mAbs) which would bind to the mouse GIP in suspension. Due to the high correspondence in identity between mouse GIP and human GIP, it was expected that these mAbs which bound to mouse GIP would also bind to human GIP.

Next, the ability of hybridoma supernates to neutralize GIP and prevent ligand-receptor interaction, receptor activation and receptor-dependent signaling was tested using a cell culture system. This system used reporter cells (LGIPR2 cells), which possess the lacZ gene under the control of a cyclic adenosine monophosphate (cAMP-)-responsive promoter and express the rat GIPR on the cell surface. The addition of GIP to these cells leads to activation of the GIPR, induction of a signaling cascade that leads to accumulation of cAMP, induction of the lacZ gene and synthesis of β-galactosidase. After the addition of a test sample and incubation for 4 hours, a colorimetric assay was used to measure β-galactosidase content in cell lysates. The degree of color change is proportional to the level of β-galactosidase activity. The level of β-galactosidase activity is dependent on the amount of free biologically active GIP in the test sample.

Supernates from the five hybridoma clones grown in culture that scored positive in the suspension assay were diluted 1:1 and 1:20 with solutions of mouse or human GIP. The mixtures were then added to LGIPR2 cells and incubated before washing and assaying for β-galactosidase. Three of the five supernates showed significant inhibition of mouse GIP when diluted 1:1, and two of those three supernates showed significant inhibition of mouse GIP when diluted 1:20.

To demonstrate that the monoclonal antibodies were specific to GIP, the supernates from the five hybridomas that scored positive in the suspension assay were diluted 1:1 with a 0.1 nM solution of human glucagon-like peptide-1 (GLP-1). The mixtures were then added to LGLP-1R cells. LGLP-1R cells are identical to LGIPR2 cells except they express the GLP-1 receptor and not the GIPR. The cells were incubated for 4 hours at 37° C. before the mixtures were removed, the cells washed and β-galactosidase content was assayed. None of the supernates inhibited native GLP-1, indicating specificity to GIP.

Next, the two hybridomas that produced supernates that showed significant inhibition of mouse GIP when diluted 1:20 were expanded and ~5×10⁵ cells were harvested and total RNA was prepared using a kit purchased from Ambion (RNaqueous-4PCR, Life Technologies). Two micrograms of the total RNA was used to make first-strand cDNA using the Suprscript III first-strand system for cDNA synthesis purchased from Life Technologies. The resultant cDNA was used to amplify the cDNA encoding the heavy and light chain variable sequences in two separate polymerase chain reactions (PCRs).

To amplify the heavy chain variable sequences, an oligonucleotide with the sequence CAGTCGAAGC TTTGAGGAGA CGGTGACCGTG GTCCCTTGGC CCCAG (SEQ ID NO: 43) was used as the reverse primer, and an oligonucleotide with the sequence: CAACTAGGAT CCAGGTSMAR CTGCAGSAGT CWGG (SEQ ID NO: 44) was used as the forward primer. The reverse primer contains the sequence AAGCTT (SEQ ID NO: 45) at its 5'-end, which is the recognition sequence for the restriction enzyme HindIII. The forward primer contains the sequence GGATCC (SEQ ID NO: 46) at its 5'-end, which is the recognition sequence for the restriction enzyme BamHI. The resultant products of the PCRs were digested with the enzymes HindIII and BamHI, then ligated to the plasmid pUC18 which was also digested with the restriction enzymes HindIII and BamHI. The ligation reaction was performed using the Fast-Link kit purchased from Epicentre. The ligation reaction was used to transform E. coli DH5α bacterial cells (Life Technologies). Bacteria that took up plasmid were selected on agar plates containing 50 microgram/milliliter (μg/ml) carbenicillin. Colonies that grew on the carbenicillin agar plates were picked and grown in 2 ml cultures for 16 hours. The bacteria was harvested and plasmid DNA was isolated using the alkaline lysis mini-prep method. Purified plasmid DNA was digested with the restriction enzymes BamHI and HindIII before the DNA was resolved by electrophoresis through a 1.2% agarose gel in a Tris-borate buffer. DNA fragments in the gel were stained with ethidium bromide and visualized using an ultraviolet lamp. Plasmids that generated restriction fragments with approximate molecular sizes of 374 base pairs were sequenced using a service purchased from Eurofins MWG Operon (Huntsville, Ala.).

To amplify the light chain variable sequences, the same procedure was generally followed as described above. The main differences were that an oligonucleotide with the sequence: CAGTCGAAGC TTGTTAGATC TCCAGCTTG GTCCC (SEQ ID NO: 47) was used as the forward primer, and an oligonucleotide with the sequence CAACTAGGAT CCGACATTCA GCTGACCCAG TCTCCA (SEQ ID NO: 48) was used as the reverse primer. Again, the forward primer contains the recognition sequence for HindIII (SEQ ID NO: 45), and the reverse primer contains the recognition sequence for BamHI (SEQ ID NO: 46). Plasmids that generated restriction fragments with approximate molecular sizes of 355 base pairs were sequenced using a service purchased from Eurofins MWG Operon (Huntsville, Ala.).

The resulting mAbs identified using the procedure described above are mouse antibodies. These mouse antibodies were partially humanized by forming a chimeric antibody possessing the variable domains of the mouse heavy and light chains fused to human heavy and light chain constant regions, respectively. This was done by amplifying the heavy chain and light chain variable sequences using the polymerase chain reaction (PCR). The templates used in the PCRs were the pUC18 derivatives containing the corresponding variable heavy or variable light chain cDNA sequences. The heavy chain variable regions were amplified using an oligonucleotide with the sequence TCACGAATTC TCAGGTCCAG CTGCAGGAGT (SEQ ID NO: 49) as the forward primer, and an oligonucleotide with the sequence TTGGTGCTAG CTGAGGAGAC GGTGACCGT (SEQ ID NO: 50), as the reverse primer. The forward primer contains the sequence GAATTC (SEQ ID NO: 51) at its 5'-end, which is the recognition sequence for the restriction enzyme EcoRI. The reverse primer contains the sequence GCTAGC (SEQ ID NO: 52) at its 5'-end, which is the recognition sequence for the restriction enzyme NheI. After PCR amplification, the DNA fragments were digested with EcoRI and NheI and ligated to the plasmid pFUSEss-CHIg-hG1 which was also digested with the restriction enzymes EcoRI and NheI. The plasmid pFUSEss-CHIg-hG1 is a mammalian expression vector purchase from InvivoGen (San Diego, Calif.). Cloning the variable heavy chain cDNA sequences into this plasmid produces a gene that encodes a chimeric heavy chain consisting of the mouse variable region and a human constant region. The ligation reaction was performed using the Fast-Link kit purchased from Epicentre. The ligation reaction was used to transform E. coli DH5α bacterial cells (Life Technologies). Bacteria that took up plasmid were selected on agar plates containing 50 μg/ml zeomycin. Colonies that grew on the zeomycin agar plates were picked and grown in 2 ml cultures for 16 hours. The bacteria were harvested and plasmid DNA was isolated using the alkaline lysis mini-prep method. Purified plasmid DNA was digested with the restriction enzymes EcoRII and NheI before the DNA was resolved by electrophoresis through a 1.2% agarose gel in a Tris-borate buffer. DNA fragments in the gel were stained with ethidium bromide and visualized using an ultraviolet lamp. Successful cloning was confirmed by identification of a DNA fragment with a molecular size of 373 base pairs.

The light chain variable regions were amplified using an oligonucleotide with the sequence GTCACGAATTCAGACATTCAGCTGACCCAG (SEQ ID NO: 55) containing the recognition sequence (SEQ ID NO: 51) for the restriction enzyme EcoRI as the forward primer, and an oligonucleotide with the sequence AGCCACCGTA CGTTTGATCT CCAGCTTGGT CCCA (SEQ ID NO: 53) as the reverse primer. The reverse primer contains the sequence CGTACG (SEQ ID NO: 54) at its 5'-end, which is the recognition sequence for the restriction enzyme BsiWI. After PCR amplification, the DNA fragments were digested with EcoRI and BswiI and ligated to the plasmid pFUSE2ss-CLIg-hK which was also digested with the restriction enzymes EcoRI and BswiI. The plasmid pFUSE2ss-CLIg-hK is a mammalian expression vector purchase from InvivoGen (San Diego, Calif.). Cloning the variable light chain cDNA sequences into this plasmid produces a gene that encodes a chimeric light chain consisting of the mouse variable region and the human constant region. The ligation reaction was performed using the Fast-Link kit purchased from Epicentre. The ligation reaction was used to transform E. coli DH5α bacterial cells (Life Technologies). Bacteria that took up plasmid were selected on agar plates containing 50 μg/ml blastocidin. Colonies that grew on the blastocidin agar plates were picked and grown in 2 ml cultures for 16 hours. The bacteria were harvested and plasmid DNA was isolated using the alkaline lysis mini-prep method. Purified plasmid DNA was digested with the restriction enzymes EcoRII and BsiWI before the DNA was resolved by electrophoresis through a 1.2% agarose gel in a Tris-borate buffer. DNA fragments in the gel were stained with ethidium bromide and visualized using an ultraviolet lamp. Successful cloning was confirmed by identification of a DNA fragment with a molecular size of 353 base pairs.

To express chimeric antibodies containing the variable regions cloned from the hybridomas and human constant regions, pFUSEss-CHIg-hG1 and the pFUSE2ss-CLIg-hK derivatives containing the variable heavy chain and variable light chain sequences, respectively, were introduced into Chinese hamster ovary (CHO-1) cells in culture. Plasmid DNA was introduced by transfection employing the cationic lipid reagent Turbofect (Thermo Scientific, Pittsburgh, Pa.) to facilitate the entry of DNA into cultured cells. Two days after transfection, cell supernate was collected and analyzed for GIP-neutralizing activity. To demonstrate the ability of the chimeric mAbs to neutralize GIP, the cell supernate was mixed with an equal volume of $2\times10^{-9}$ M hGIP, before adding to LGIPR2 cells in culture. After incubation at 37° C. for 4 hours, the cells were lysed and β-galactosidase activity assayed. In this assay, the combination of the plasmids containing the variable light chain sequences and the variable heavy chain sequences from the hybridoma designated 10g10, was able to neutralize GIP activity in the cell-based reporter assay.

The variable regions of the mAbs made and identified using the procedures disclosed above were maintained, and the constant regions were substituted with human constant regions. Alternatively, the GIP mAb antagonists could be made using transgenic mice to make "fully" human mAbs, or other technologies could be used as well. For example, the amino acids in the variable domains that are conserved in mouse antibodies could be replaced with amino acids that are conserved in human antibodies.

The resulting monoclonal antibody antagonist thus binds to GIP. In particular embodiments, the molecular antagonist used in the compositions of the present disclosure can bind to an amino sequence selected from the group consisting of SEQ ID NO: 1, SEQ ID NO: 2, SEQ ID NO: 3, and SEQ ID NO: 4. Put another way, the antagonist (e.g. monoclonal antibody) binds to epitopes contained in these four sequences.

In various embodiments, the molecular antagonist has a molecular weight (MW) of about 30 kDa to about 500 kDa, including from about about 120 kDa to about 500 kDa. In other embodiments, the molecular antagonist has a binding affinity for GIP characterized by an $IC_{50}$ of about 0.1 nM to about 7 nM.

As previously discussed, the monoclonal antibody antagonist that binds to GIP has variable domains in the light chains and heavy chains that bind to GIP, or more specifically the CDRs of the variable domains of the light chains and heavy chains bind to GIP. It is generally contemplated that the molecular antagonists of the present disclosure contain at least one complementarity determining region (CDR) that binds to GIP. More specifically, the molecular antagonist contains at least one CDR having at least 80% identity to an amino acid sequence selected from the group consisting of SEQ ID NO: 20, SEQ ID NO: 21, SEQ ID NO: 22, SEQ ID NO: 23, SEQ ID NO: 24, SEQ ID NO: 31, SEQ ID NO: 32, and SEQ ID NO: 33. These CDRs were identified through various modifications of the variable domains in the light chain and heavy chain identified in the 10g10 hybridoma referred to above. Those modifications are discussed in more detail in the Examples section below.

More desirably, the CDR(s) has/have at least 85%, or at least 90%, or at least 95% identity, or have 100% identity with these amino acid sequences. In more specific embodiments, the molecular antagonist contains two, three, four, five, or six CDRs having the requisite identity with two, three, four, five, or six different amino acid sequences in the above-mentioned group.

In some more specific embodiments, the molecular antagonist comprises a light chain variable domain having a first CDR and a second CDR, each CDR having at least 95% identity to an amino acid sequence selected from the group consisting of SEQ ID NO: 20, SEQ ID NO: 21, SEQ ID NO: 22, SEQ ID NO: 23, and SEQ ID NO: 24. These CDRs were identified in the variable domain of the light chain. More desirably, the CDRs have 100% identity with these amino acid sequences.

In other particular embodiments, the molecular antagonist comprises a light chain variable domain having a first CDR with at least 80% identity to the amino acid sequence of SEQ ID NO: 20, a second CDR with at least 80% identity to the amino acid sequence of SEQ ID NO: 21, and a third CDR with at least 85% identity to the amino acid sequence of SEQ ID NO: 22. A variable domain containing the combination of these three CDRs was identified as having a very high binding affinity for GIP. More desirably, the three CDRs have at least 85%, or at least 90%, or at least 95% identity, or have 100% identity with these amino acid sequences.

In additional embodiments, the molecular antagonist comprises a heavy chain variable domain having a first CDR with at least 80% identity to the amino acid sequence of SEQ ID NO: 31, a second CDR with at least 80% identity to the amino acid sequence of SEQ ID NO: 32, and a third CDR with at least 80% identity to the amino acid sequence of SEQ ID NO: 33. A variable domain containing the combination of these three CDRs was identified as having a very high binding affinity for GIP. More desirably, the three CDRs have at least 85%, or at least 90%, or at least 95% identity, or have 100% identity with these amino acid sequences.

It is generally contemplated that these variable domains contain two or three CDRs as specified above, with the CDRs being joined to each other by linking groups. The linking groups can generally be any groups that will permit the CDRs to bind to GIP. For example, the linking groups can be chains of amino acids, as are present in the natural variable domains of antibodies. The amino acids can be of any desired length.

In particular embodiments, the molecular antagonist comprises a light chain variable domain with at least 80% identity to an amino acid sequence selected from the group consisting of SEQ ID NO: 16, SEQ ID NO: 17, SEQ ID NO: 18, and SEQ ID NO: 19. More desirably, the light chain variable domain has at least 85%, or at least 90%, or at least 95%, or has 100% identity with one of these amino acid sequences. These variable domains contain various combinations of the light chain CDRs of SEQ ID NO: 20, SEQ ID NO: 21, SEQ ID NO: 22, SEQ ID NO: 23, and SEQ ID NO: 24, linked together with amino acids.

In other embodiments, the molecular antagonist comprises a heavy chain variable domain with at least 80% identity to an amino acid sequence selected from the group consisting of SEQ ID NO: 27, SEQ ID NO: 28, SEQ ID NO: 29, and SEQ ID NO: 30. More desirably, the heavy chain variable domain has at least 85%, or at least 90%, or at least 95%, or has 100% identity with one of these amino acid sequences. These variable domains contain various combinations of the heavy chain CDRs of SEQ ID NO: 31, SEQ ID NO: 32, SEQ ID NO: 33, and SEQ ID NO: 34, linked together with amino acids.

Also contemplated are molecular antagonists having any combination of the light chain variable domains and the heavy chain variable domains disclosed above. More specifically, some molecular antagonists contain only one light chain variable domain and only one heavy chain variable domain. Others contain multiple light chain variable domains and heavy chain variable domains; in these embodiments usually the multiple light chain variable domains are the same, and the multiple heavy chain variable domains are the same.

In some specific embodiments, the molecular antagonist comprises a light chain variable domain and a heavy chain variable domain. The light chain variable domain comprises a first CDR and a second CDR, each CDR having at least 95% identity to an amino acid sequence selected from the group consisting of SEQ ID NO: 20, SEQ ID NO: 21, SEQ ID NO: 22, SEQ ID NO: 23, and SEQ ID NO: 24; and the heavy chain variable domain comprises a first CDR with at least 80% identity to the amino acid sequence of SEQ ID NO: 31, a second CDR with at least 80% identity to the amino acid sequence of SEQ ID NO: 32, and a third CDR with at least 80% identity to the amino acid sequence of SEQ ID NO: 33. The light chain variable domain may have 100% identity with one of the listed amino acid sequences. More particularly, the heavy chain variable domain has at least 85%, or at least 90%, or at least 95%, or has 100% identity with one of the listed amino acid sequences.

In other specific embodiments, the molecular antagonist comprises a light chain variable domain and a heavy chain variable domain. The light chain variable domain has at least 80% identity to an amino acid sequence selected from the group consisting of SEQ ID NO: 16, SEQ ID NO: 17, SEQ ID NO: 18, and SEQ ID NO: 19; and the heavy chain variable domain has at least 80% identity to an amino acid sequence selected from the group consisting of SEQ ID NO: 27, SEQ ID NO: 28, SEQ ID NO: 29, and SEQ ID NO: 30. More particularly, the light chain variable domain and/or the heavy chain variable domain has at least 85%, or at least 90%, or at least 95%, or has 100% identity with one of their listed amino acid sequences.

In even more specific embodiments, the molecular antagonist has a light chain variable domain having at least 80% identity to SEQ ID NO: 18, and a heavy chain variable domain having at least 80% identity to an amino acid sequence selected from the group consisting of SEQ ID NO: 28, SEQ ID NO: 29, and SEQ ID NO: 30. Again, these domains can have at least 85%, or at least 90%, or at least 95%, or 100% identity with one of their listed amino acid sequences.

In particularly desirable embodiments, the molecular antagonist has a light chain variable domain having at least 90% identity to SEQ ID NO: 18, and a heavy chain variable domain having at least 90% identity to SEQ ID NO: 29. In more specific embodiments, these domains can have at least 95%, or can have 100% identity with their listed amino acid sequence.

The molecular antagonists of the present disclosure have, in several different embodiments, a light chain variable domain and a heavy chain variable domain as described above. It is particularly contemplated that the molecular antagonist could be a single-chain variable fragment (scFv), an F(ab')$_2$ fragment, a Fab or Fab' fragment, a diabody, a triabody, a tetrabody, or a monoclonal antibody of which these variable domains would be a part.

A single-chain variable fragment (scFv) includes a light chain variable domain and a heavy chain variable domain, joined together with a linking group which usually has a length of about 10 to about 25 amino acids (though it does not need to be within this range). The N-terminus of one variable domain is connected to the C-terminus of the other variable domain. If desired, the scFV can be PEGylated (with polyethylene glycol) to increase its size, as with certolizumab pegol. Two scFvs can be joined together with another linking group to produce a tandem scFv.

If a light chain variable domain and a heavy chain variable domain are joined together with a shorter linking group to form an scFv, the two variable domains cannot fold together, and the scFv will dimerize to form a diabody. Even shorter linking groups can result in the formation of trimers (i.e. a triabody) and tetramers (i.e. a tetrabody).

A whole monoclonal antibody is formed from two heavy chains and two light chains. Again, each light chain and each heavy chain contains a variable domain. Each light chain is bonded to a heavy chain. The two heavy chains are joined together at a hinge region. If the constant region of the heavy chains are removed below the hinge region, an F(ab')$_2$ fragment is produced which contains a total of four variable domains. The F(ab')$_2$ fragment can then be split into two Fab' fragments. An Fab' fragment contains sulfhydryl groups from the hinge region. A Fab fragment is formed when the constant region of the heavy chains is removed above the hinge region, and does not sulfhydryl groups from the hinge region. However, all of these fragments contain a light chain variable domain and a heavy chain variable domain.

In desirable embodiments explored in experiments described below, the molecular antagonist is a whole monoclonal antibody formed from light chains and heavy chains having the variable regions/domains disclosed above, combined with human constant regions. The constant region of the heavy chain can be any human isotype, including IgA1, IgA2, IgD, IgE, IgG1, IgG2, IgG3, IgG4, or IgM. The human constant region of the light chain can be the kappa or lambda isotype. In specific embodiments, the heavy chain constant region is the IgG1 isotype, and the light chain constant region is the kappa isotype.

In particular embodiments, the molecular antagonist is a monoclonal antibody with a light chain variable domain having at least 80% identity to SEQ ID NO: 18, and a heavy chain variable domain having at least 80% identity to an amino acid sequence selected from the group consisting of SEQ ID NO: 28, SEQ ID NO: 29, and SEQ ID NO: 30. These domains can have at least 85%, or at least 90%, or at least 95%, or 100% identity with one of their listed amino acid sequences.

In other particular embodiments, the molecular antagonist is a whole monoclonal antibody with a light chain variable domain having at least 90% identity to SEQ ID NO: 18, and a heavy chain variable domain having at least 90% identity to SEQ ID NO: 29. These domains can have at least 95%, or can have 100% identity with their listed amino acid sequence.

The molecular antagonist of GIP, which in particular forms is a monoclonal antibody, can then be used in a composition that can be administered to a person. The composition contains a pharmaceutically effective amount of the molecular antagonist of GIP. In particular embodiments, the composition contains the molecular antagonist in an amount of from about 0.1 to about 1000 milligrams per milliter of the composition (w/v).

The pharmaceutical compositions containing the molecular antagonist of GIP is generally administered by a parenteral (i.e. subcutaneously, intramuscularly, intravenously, intraperitoneally, intrapleurally, intravesicularly or intrathecally) route, as necessitated by choice of drug and disease. The dose used in a particular formulation or application will be determined by the requirements of the particular state of disease and the constraints imposed by the characteristics of capacities of the carrier materials. It contemplated in that in the most desirable form, the composition will be administered intravenously, intraperitoneally, or subcutaneously.

The pharmaceutical composition may include a pharmaceutically acceptable carrier. The carrier acts as a vehicle for delivering the molecular antagonist. Examples of pharmaceutically acceptable carriers include liquid carriers like water, oil, and alcohols, in which the molecular antagonists can be dissolved or suspended.

The pharmaceutical composition may also include excipients. Particular excipients include buffering agents, surfactants, preservative agents, bulking agents, polymers, and stabilizers, which are useful with these molecular antagonists. Buffering agents are used to control the pH of the composition. Surfactants are used to stabilize proteins, inhibit protein aggregation, inhibit protein adsorption to surfaces, and assist in protein refolding. Exemplary surfactants include Tween 80, Tween 20, Brij 35, Triton X-10, Pluronic F127, and sodium dodecyl sulfate. Preservatives are used to prevent microbial growth. Examples of preservatives include benzyl alcohol, m-cresol, and phenol. Bulking agents are used during lyophilization to add bulk. Hydrophilic polymers such as dextran, hydroxyl ethyl starch, polyethylene glycols, and gelatin can be used to stabilize proteins. Polymers with nonpolar moieties such as polyethylene glycol can also be used as surfactants. Protein stabilizers can include polyols, sugars, amino acids, amines, and salts. Suitable sugars include sucrose and trehalose. Amino acids include histidine, arginine, glycine, methionine, proline, lysine, glutamic acid, and mixtures thereof. Proteins like human serum albumin can also competitively adsorb to surfaces and reduce aggregation of the protein-like molecular antagonist. It should be noted that particular molecules can serve multiple purposes. For example, histidine can act as a buffering agent and an antioxidant. Glycine can be used as a buffering agent and as a bulking agent.

The pharmaceutical composition may be in the form of a powder, injection, solution, suspension, or emulsion. It is contemplated that the composition will be delivered by injection. Sometimes, the molecular antagonist of GIP can be lyophilized using standard techniques known to those in this art. The lyophilized antagonist may then be reconstituted with, for example, suitable diluents such as normal saline, sterile water, glacial acetic acid, sodium acetate, combinations thereof and the like.

Dose will depend on a variety of factors, including the therapeutic index of the drugs, disease type, patient age, patient weight, and tolerance. The dose will generally be chosen to achieve serum concentrations from about 0.1 µg/ml to about 100 µg/ml in the patient. The dose of a particular patient can be determined by the skilled clinician using standard pharmacological approaches in view of the above factors. The response to treatment may be monitored by analysis of blood or body fluid levels of glucose or insulin levels, or by monitoring fat levels in the patient. The skilled clinician will adjust the dose based on the response to treatment revealed by these measurements. A single administration may usually be sufficient to produce a therapeutic effect, but it is contemplated that multiple administrations will be used to assure continued response over a substantial period of time. Because of the protein-like nature of the molecular antagonists disclosed herein, it is believed that the antagonists will have a long half-life in the body, so that the composition will only need to be administered once or twice a month, or possibly once a week. The circulating concentration of the molecular antagonist should be sufficient to neutralize GIP that is generated during and after eating.

The pharmaceutical compositions containing the GIP molecular antagonists of the present disclosure can be used to treat fatty liver disease or other diseases that involve the accumulation of fat in tissue. The pharmaceutical compositions containing the GIP molecular antagonists of the present disclosure can also be used to treat hyperphagia and disorders and conditions characterized by hyperphagia.

The term "treat" is used to refer to a reduction in progression of the disease, a regression in the disease, and/or a prophylactic usage to reduce the probability of presentation of the disease. This can be measured in several different ways, such as via the liver fat fraction, the omental fat fraction, or the subcutaneous fat fraction; or via weight, or degree of weight gain/loss. In particular, obesity can be reversed by the administration of these compositions.

For obese individuals, it is believed that the GIP molecular antagonists will inhibit binding of GIP to its receptor in enterocytes, diminishing postprandial glucose absorption by inhibiting GIP-induced translocation of sodium/glucose transports (SGLT1) from the cytoplasm to the luminal membrane. GIP-induced insulin secretion from pancreatic beta cells will also be attenuated, decreasing the nutrient storage associated with an elevated insulin response. Inhibiting binding of GIP to its receptor in adipocytes should also decreased GIP-induced glucose uptake into fat cells and prevent GIP from inhibiting lipolysis. Overall, this results in less efficient nutrient uptake and storage, promoting weight loss or at least a reduced degree of weight gain. These effects also benefit patients with metabolic syndrome or hyperlipidemia.

For patients with type II diabetes, inhibiting GIP binding to its receptor in enterocytes will lower postprandial glucose absorption and blood sugar. Patients who overeat will also benefit from the weight-lowering effects of neutralizing GIP.

For patients susceptible to or suffering from fatty liver disease, inhibiting GIP binding to its receptor in beta cells will lower postprandial insulin secretion, thus reducing insulin-induced fat accumulation in the liver.

For patients suffering from food-induced Cushing's syndrome, inhibiting GIP binding to its receptor in adrenal cells will reduce or prevent the increase in GIP-induced cortisol secretion after food intake.

The present disclosure will further be illustrated in the following non-limiting three sets of working examples, it being understood that these examples are intended to be illustrative only and that the disclosure is not intended to be limited to the materials, conditions, process parameters and the like recited herein. All proportions are by weight unless otherwise indicated.

EXAMPLES

Example 1

Monoclonal antibodies were generated and screened as described above using hybridomas to identify a monoclonal antibody having high binding affinity for gastric inhibitory peptide (GIP) in suspension. The 10g10 monoclonal antibody was thus identified.

The 10g10 light chain variable domain has the amino acid sequence of SEQ ID NO: 16. The first CDR of the light chain variable domain has the amino acid sequence of SEQ ID NO: 25. The second CDR of the light chain variable domain has the amino acid sequence of SEQ ID NO: 26. The third CDR of the light chain variable domain has the amino acid sequence of SEQ ID NO: 22. cDNA encoding for the 10g10 light chain variable domain has the nucleotide sequence of SEQ ID NO: 35.

The 10g10 heavy chain variable domain has the amino acid sequence of SEQ ID NO: 27. The first CDR of the heavy chain variable domain has the amino acid sequence of SEQ ID NO: 31. The second CDR of the heavy chain variable domain has the amino acid sequence of SEQ ID NO: 34. The third CDR of the heavy chain variable domain has the amino acid sequence of SEQ ID NO: 33. cDNA encoding for the 10g10 heavy chain variable domain has the nucleotide sequence of SEQ ID NO: 39.

For comparison, the 14B9 antibody was identified as not having binding affinity for GIP. The 14B9 light chain variable domain has the amino acid sequence of SEQ ID NO: 7. The first CDR of the light chain variable domain has the amino acid sequence of SEQ ID NO: 9. The second CDR of the light chain variable domain has the amino acid sequence of SEQ ID NO: 26. The third CDR of the light chain variable domain has the amino acid sequence of SEQ ID NO: 10. cDNA encoding for the 14B9 light chain variable domain has the nucleotide sequence of SEQ ID NO: 8.

The 14B9 heavy chain variable domain has the amino acid sequence of SEQ ID NO: 11. The first CDR of the heavy chain variable domain has the amino acid sequence of SEQ ID NO: 13. The second CDR of the heavy chain variable domain has the amino acid sequence of SEQ ID NO: 14. The third CDR of the heavy chain variable domain has the amino acid sequence of SEQ ID NO: 15. cDNA encoding for the 14B9 heavy chain variable domain has the nucleotide sequence of SEQ ID NO: 12.

Example 2

Materials and Methods 30 nine-week old male C57BL/6 mice were purchased from Jackson Laboratories (Bar Harbor, Me.). On the first day of the study, each mouse weighed between 19 and 25 grams. The mice were then subsequently divided at random into three groups of 10 mice each.

All mice had free access to food and water throughout the study. The mice were all housed in an animal facility kept at 22±2° Celsius with a 12-hour light/12-hour dark cycle. Mice were housed in groups of five per cage until they each reached a weight of 25 grams. Mice were then subsequently housed two to three animals per cage.

A high-fat diet (HFD) (catalog no. TD.06414) and a low-fat isocaloric diet (catalog no. TD.08806) were purchased from Harlan-Teklad (Indianapolis, Ind.). The HFD consisted, by weight, of approximately 23.5% protein, 27.3% carbohydrates and 34.3% fat. The HFD provided 18.4% of total calories from protein, 21.3% from carbohydrates, and 60.3% from fat, and 5.1 kcal/gram. The isocaloric diet consisted, by weight, of approximately 18.6% protein, 62.6% carbohydrates and 4.2% fat. The isocaloric diet provided 20.5% of total calories from protein, 69.1% from carbohydrates, and 10.4% from fat, and 3.6 kcal/gram.

One group of 10 mice (HFD-control group) was fed the HFD for 17 weeks and administered 0.1 mL phosphate buffered saline (PBS) by intraperitoneal (i.p.) injection five times per week.

The second group of 10 mice (HFD-mAb group) was fed the HFD for 17 weeks and administered the 10g10 GIP mAb in PBS five times per week. On Monday through Thursday, a 0.1 mL solution consisting of 0.2 mg/mL mAb in PBS was administered by i.p. injection. On each Friday, a 0.1 mL solution consisting of 0.4 mg/mL mAb in PBS was administered by i.p. injection. This resulted in administration of 10 mg/kg BW of the GIP mAb on four days of the week and 20 mg/kg BW of the GIP mAb on one day of the week, for each week of the study. This dosing regimen was continued over the course of the study.

The third group of 10 mice (iso-diet group) was fed the isocaloric diet for 17 weeks. No injections were administered to this group.

The weight of each mouse was measured and recorded each Monday evening for the duration of the study. Additionally, the amount of food consumed for each group was also measured and recorded throughout the course of the study.

Results

The HFD-Control Group Gained Weight at Nearly Twice the Rate of the HFD-mAb Group or the Iso-Diet Group.

Figure 1B:
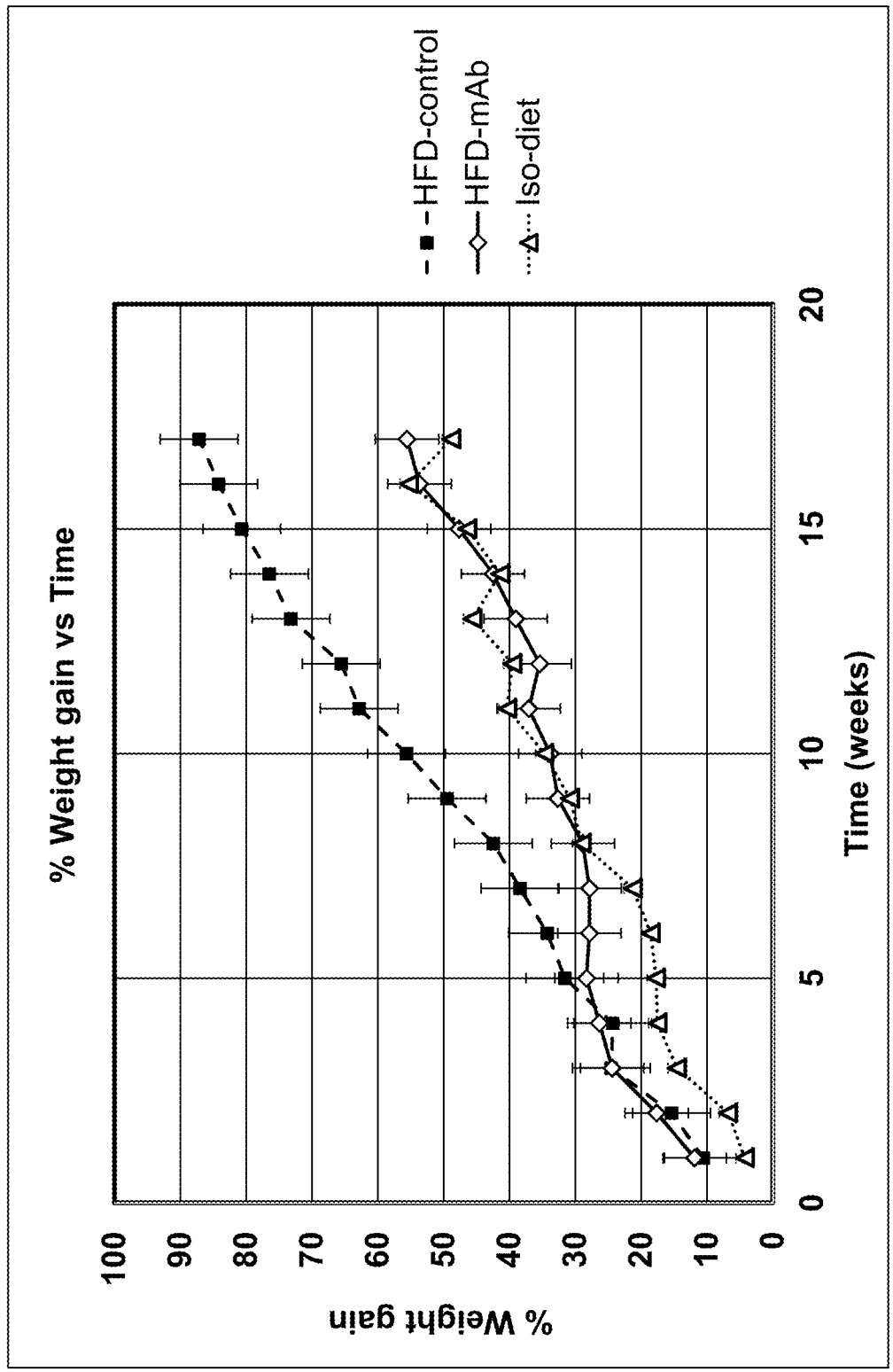
FIG. 1B is a graph showing the percent weight gain versus time for the three different sets of mice. Mice administered the GIP mAb gained weight much less quickly. The HFD-control mice gained weight at almost twice the rate of the HFD-mAb mice.

The total body weight versus time is illustrated in FIG. 1A. The percentage weight gain for each week is illustrated in FIG. 1B. After one week on the special diets, both high fat diet (HFD) groups (with and without GIP mAb) gained approximately 10% of their body weight. The weight gains of both HFD groups remained about equal until week 4, when the HFD-mAb group began to slow down in weight gain, while the weights of the HFD-control group steadily increased. The difference in weight gain became very significant (p<0.001) by week 7. The iso-diet group gained weight at a slower rate through the duration of the study. The HFD-mAb group and the iso-diet group had about the same amount of weight gain after 17 weeks. The administration of the GIP mAb antagonist had a clear effect on the weight gain of the mice.

Based on FIG. 1B, it seems that the effects of GIP mAb were not immediate, but rather required consistent dosing over time. In weeks 1-4 of the experiment, both groups of mice fed the HFD experienced nearly identical weight gain. Only starting in week 5 did the weight gain of the HFD-mAb group begin increasing at a slower rate compared to the HFD-control group.

MRI

Materials and Methods

After 17 weeks on the special diets, six mice were randomly selected from the HFD-control group and six mice from the HFD-mAb group for magnetic resonance imaging (MRI). All mice were anesthetized prior to imaging at the Imaging Research Core Facility at Case Western Reserve University.

A 2D T1-weighted asymmetric echo, Rapid Acquisition with Relaxation Enhancement (aRARE) sequence was performed on a Bruker Biospec 7T small animal MRI scanner (Bruker Biospin, Billerica, Mass.) (TR=1087 ms, TE=9.1 ms, FOV=100×50 mm, 512×256 matrix, 4 averages, echo train length=4, slice thickness=1 mm). The aRARE sequence provides a user-selectable echo delay to achieve $\pi/6$, $5\pi/6$, and $3\pi/2$ radian shifts between fat and water (echo shifts of 79, 396, and 714 µs at 7T).

The MR images obtained from the aRARE acquisition were used to generate separate fat and water images by a modified IDEAL image reconstruction technique for 7T and allowed for determination of lipid biodistribution in the mice. In this regard, obesity, metabolic syndrome and NAFLD are not just a consequence of total body weight, but are dependent on where the excess fat is stored.

Results

Figure 3:
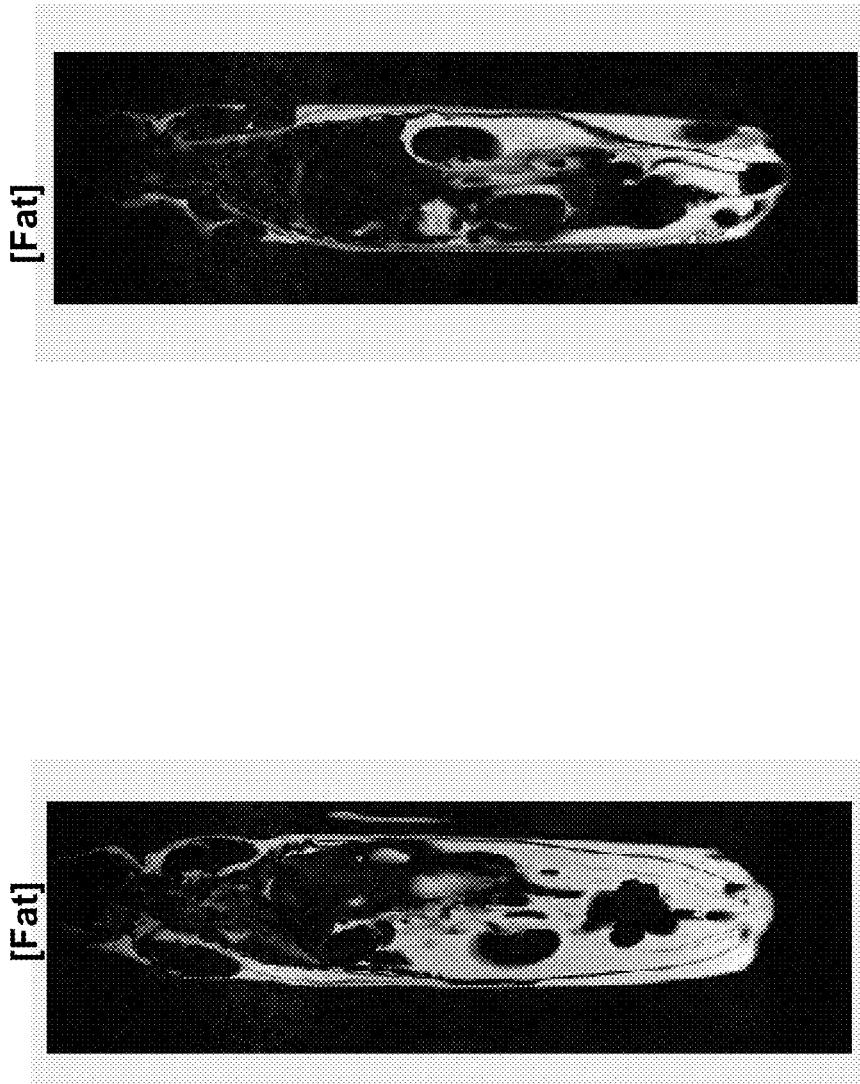
FIG. 3 shows representative magnetic resonance images of mice. Shown are representative images from the HFD-control mice (left) and the HFD-mAb mice (right). The images depict a lateral view of the mouse with the anterior of the mice being at the top and the posterior at the bottom of the image. White or bright areas represent areas of high fat content.

FIG. 3 shows representative magnetic resonance images from the HFD-control mice (left) and the HFD-mAb mice (right). The images depict a lateral view of the mouse with the anterior of the mice being at the top and the posterior at the bottom of the image. White or bright areas represent areas of high fat content. The HFD-control mice had much more fat compared to the HFD-mAb.

Figure 4:
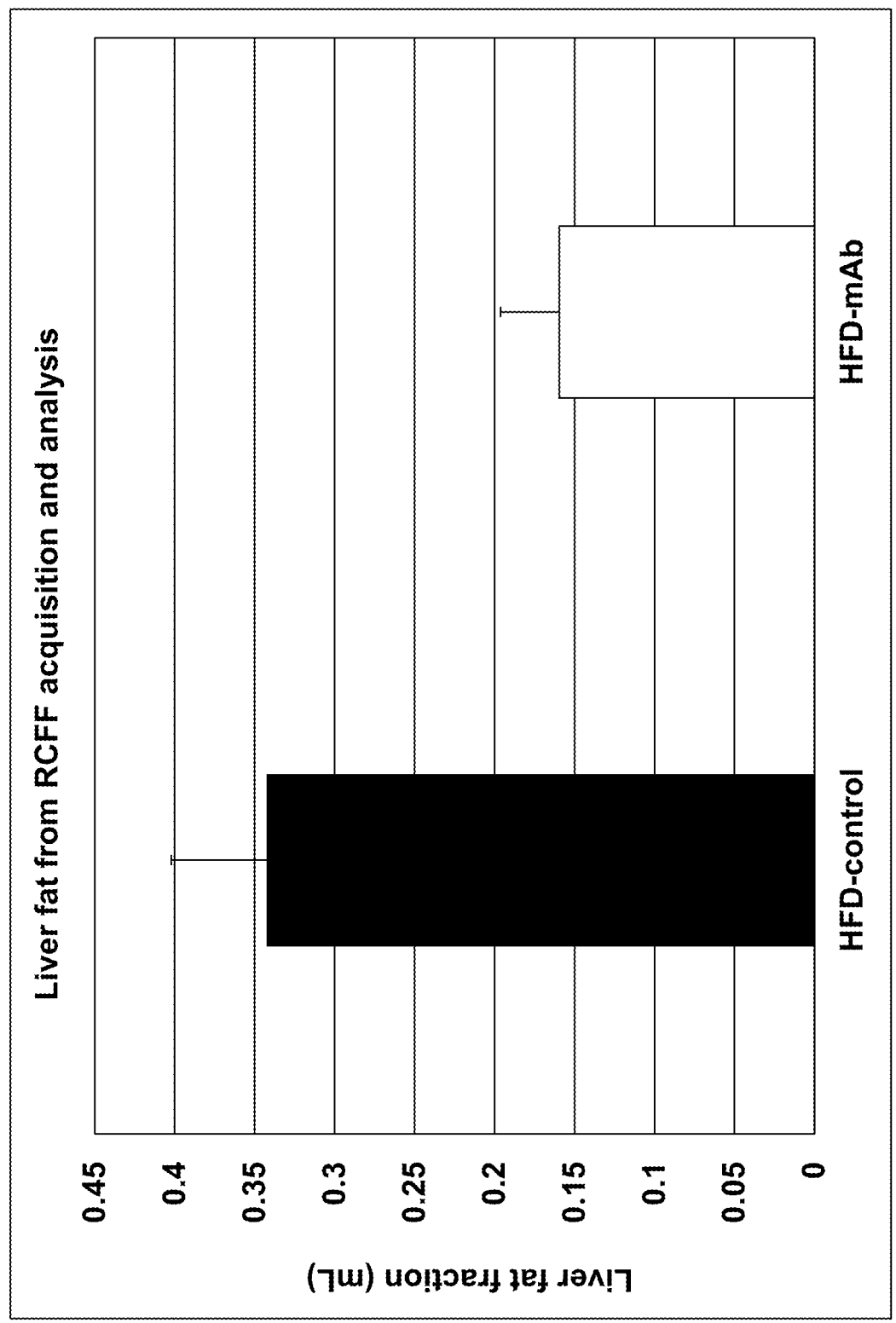
FIG. 4 shows the liver fat fraction derived from Relaxation Compensated Fat Fraction (RCFF) MRI. At the end of the 17-week diet period, 6 mice from each group were anesthetized and subjected to MRI. The RCFF technique was used to quantitatively assess the liver fat fraction in each mouse. The average liver fraction for each treatment group is plotted. The control animals accumulated twice as much fat volume in their livers compared to mice treated with the GIP-specific mAb (p=0.03).

FIG. 4 shows the liver fat fraction derived from Relaxation Compensated Fat Fraction (RCFF) MRI. The HFD-control group accumulated twice as much fat volume in their livers compared to mice in the HFD-mAb group.

Figure 5:
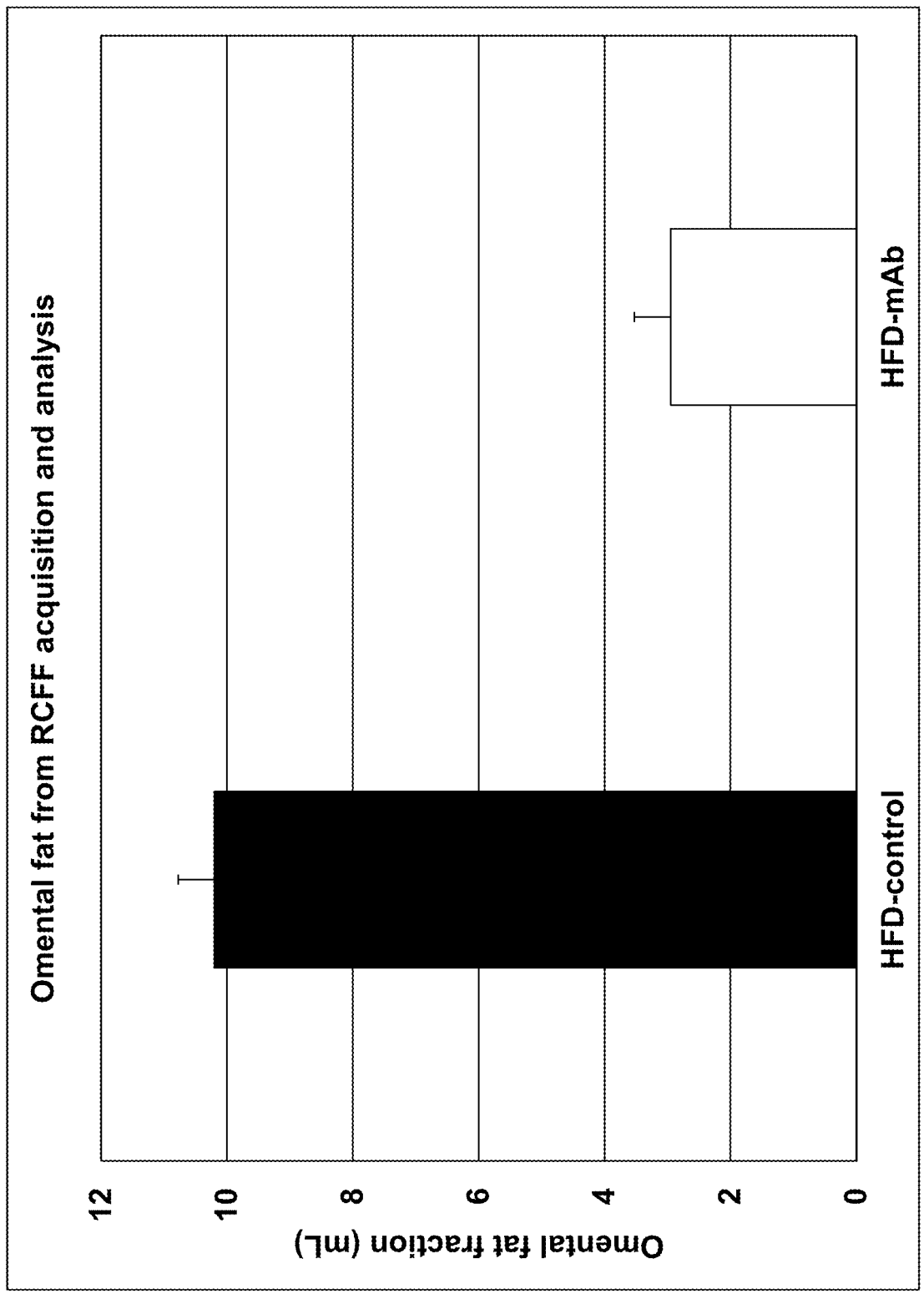
FIG. 5 shows the omental fat fraction derived from Relaxation Compensated Fat Fraction (RCFF) MRI after the 17-week diet period. The average omental fat fraction for each treatment group is plotted. The control animals accumulated almost 3.5 times more omental fat volume than the mice treated with the GIP-specific mAb (p=0.0005).

FIG. 5 shows the omental fat fraction derived from Relaxation Compensated Fat Fraction (RCFF) MRI. The HFD-control group accumulated almost 3.5 times more omental fat volume than the mice in the HFD-mAb group.

Figure 6:
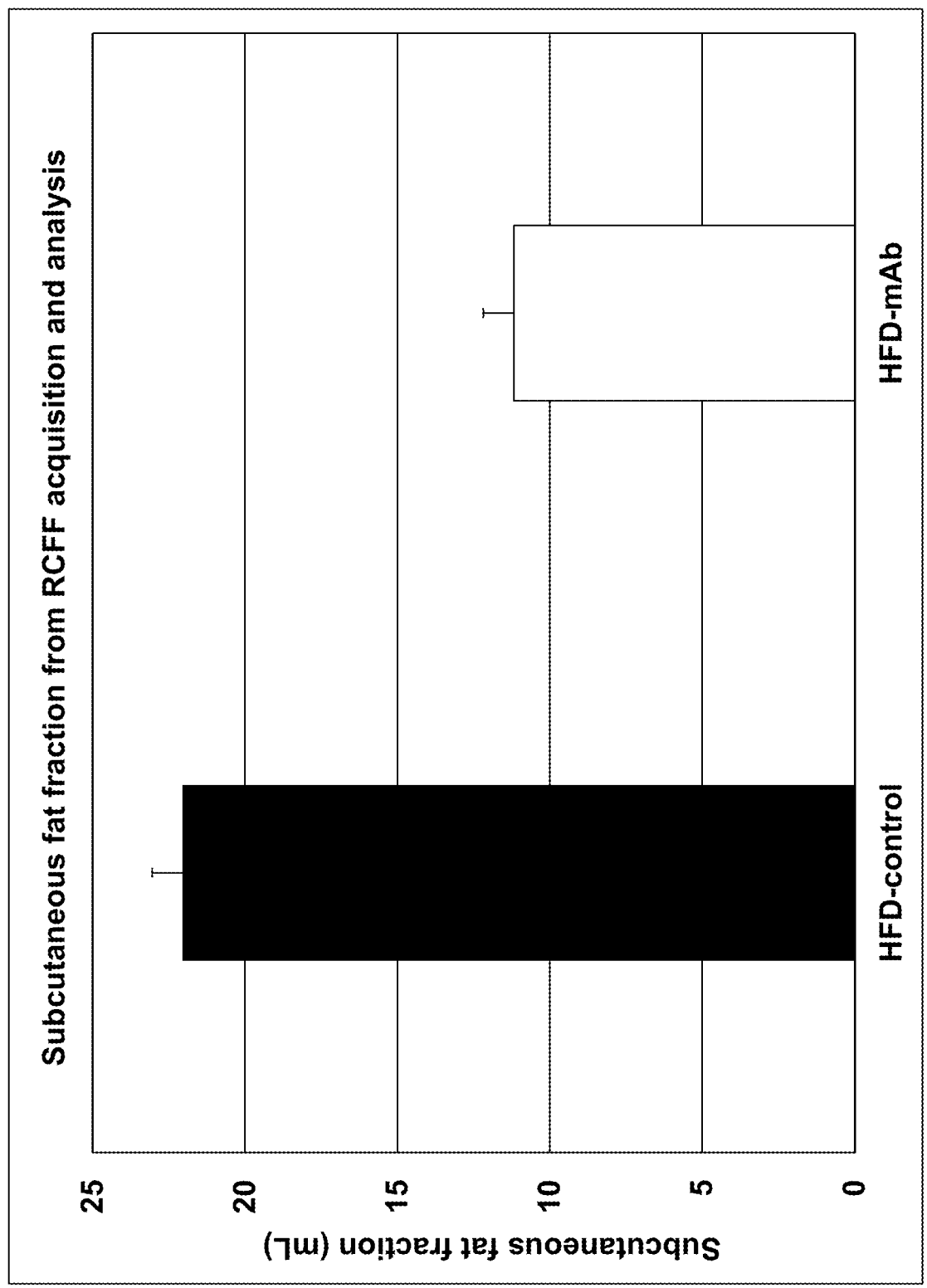
FIG. 6 shows the subcutaneous fat fraction derived from Relaxation Compensated Fat Fraction (RCFF) MRI. The average subcutaneous fat fraction for each treatment group is plotted. The control animals accumulated approximately 2 times more subcutaneous fat volume than the mice treated with the GIP-specific mAb (p=0.0002).

FIG. 6 shows the subcutaneous fat fraction derived from Relaxation Compensated Fat Fraction (RCFF) MRI. The HFD-control animals accumulated approximately 2 times more subcutaneous fat volume than the mice in the HFD-mAb group.

Figure 7:
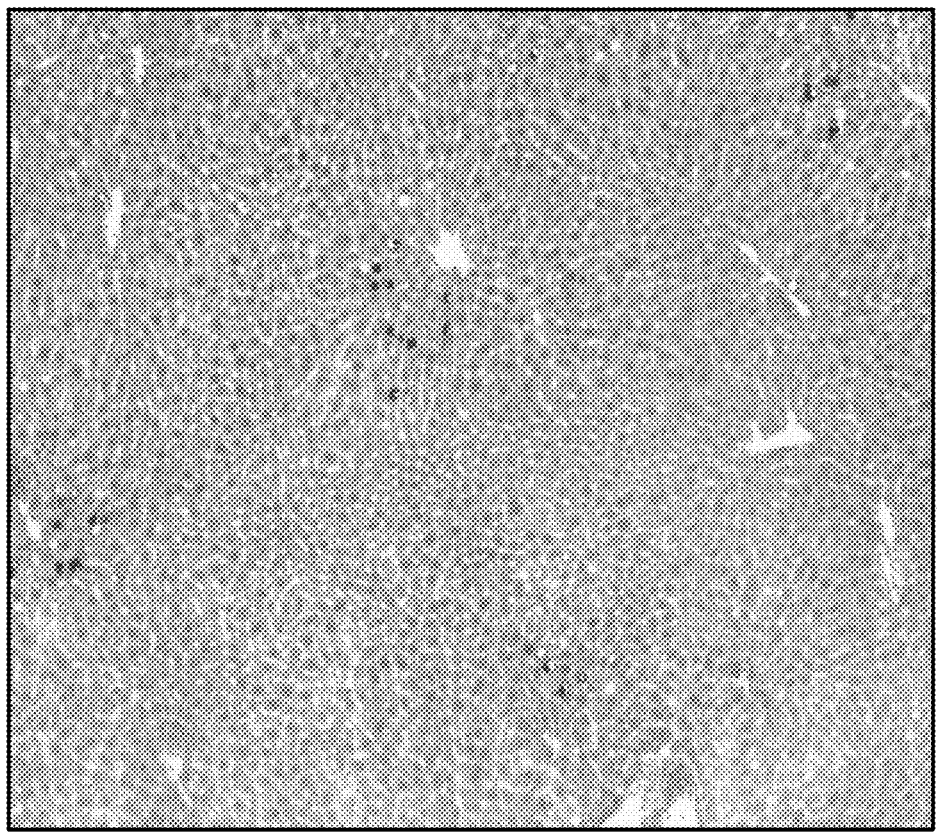
FIG. 7 shows representative photographs of stained tissue cross-sections of liver taken from sacrificed mice after the 17-week study period. The livers were removed and fixed in formalin. The fixed tissue was sectioned and stained with Oil Red O, a lysochrome diazo dye used for staining neutral triglycerides and lipids. The panels depict representative samples, showing a marked reduction in dark red fat droplets in the liver of the HFD-mAb mice (right) compared to the HFD-control mice (left).
Figure 7:
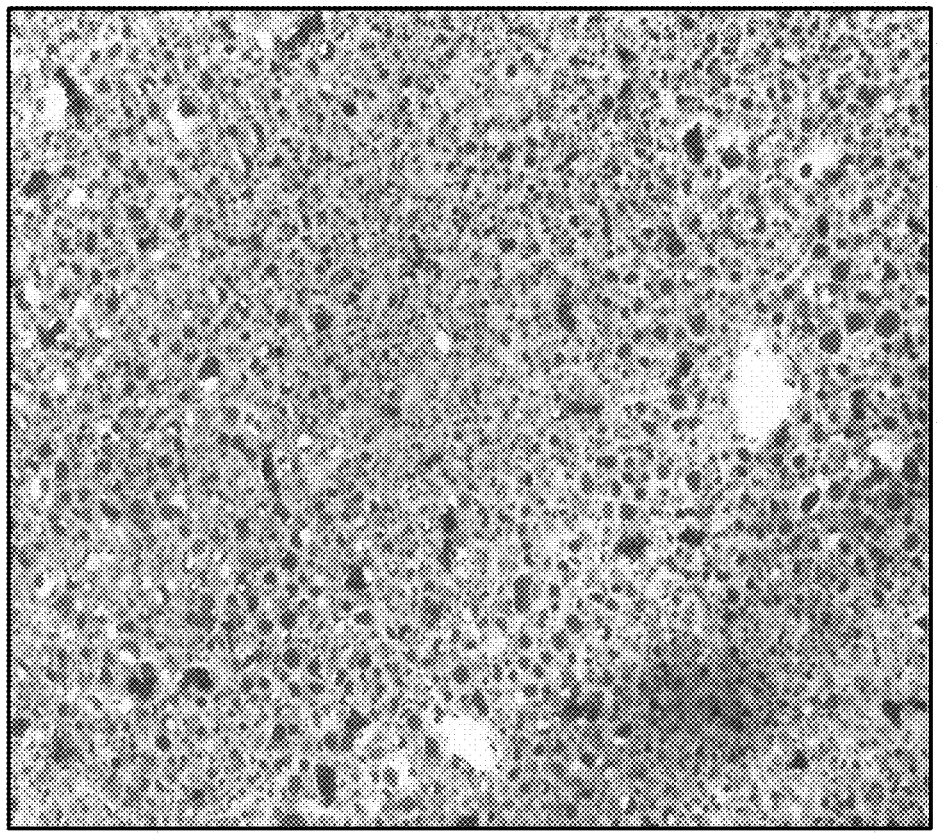

FIG. 7 shows representative photographs of stained tissue cross-sections of liver taken from sacrificed mice. The livers were removed and fixed in formalin. The fixed tissue was then sectioned and stained with Oil Red O, a lysochrome diazo dye used for staining neutral triglycerides and lipids. The HFD-control liver is on the left, and the HFD-mAb liver is on the right. There are many more red-stained (dark) fat droplets in livers in the HFD-control liver than the HFD-mAb liver. Also, the size of the fat droplets are larger in the HFD-control liver than the HFD-mAb liver. This illustrates the reduction in fat that accumulates in the liver when the GIP mAb is administered. These results agree with the liver fat fraction volume of FIG. 4.

Figure 8:
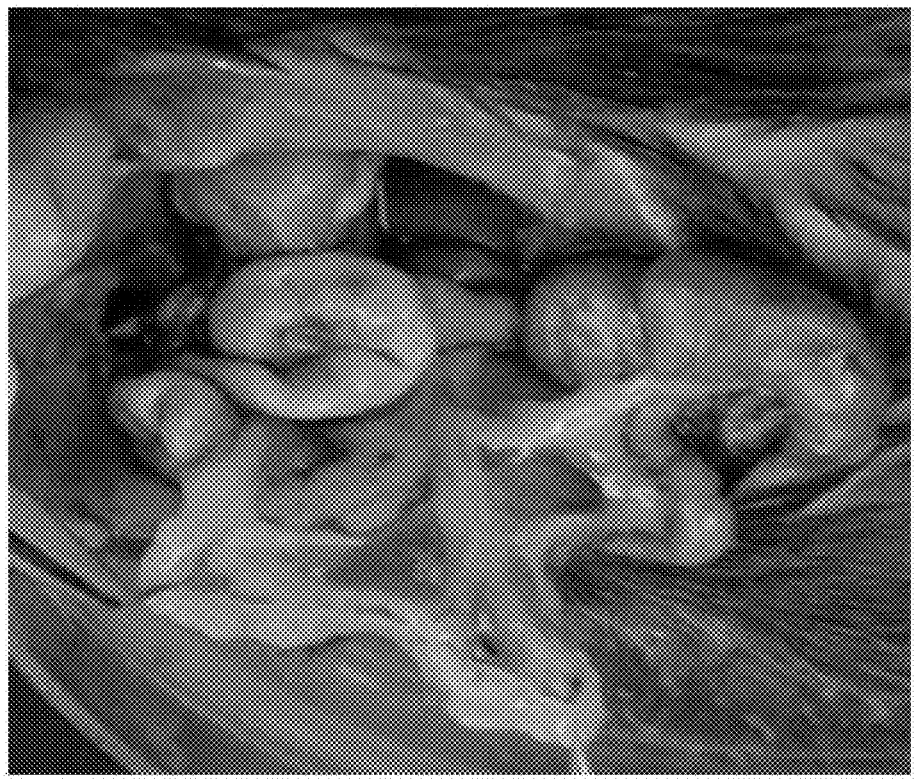
FIG. 8 is a set of two photographs comparing the omental fat found in a HFD-control mouse (left) with that of a HFD-mAb mouse (right) after the 17-week study period. The fat is white, and much more fat is visible in the HFD-control mouse.
Figure 8:
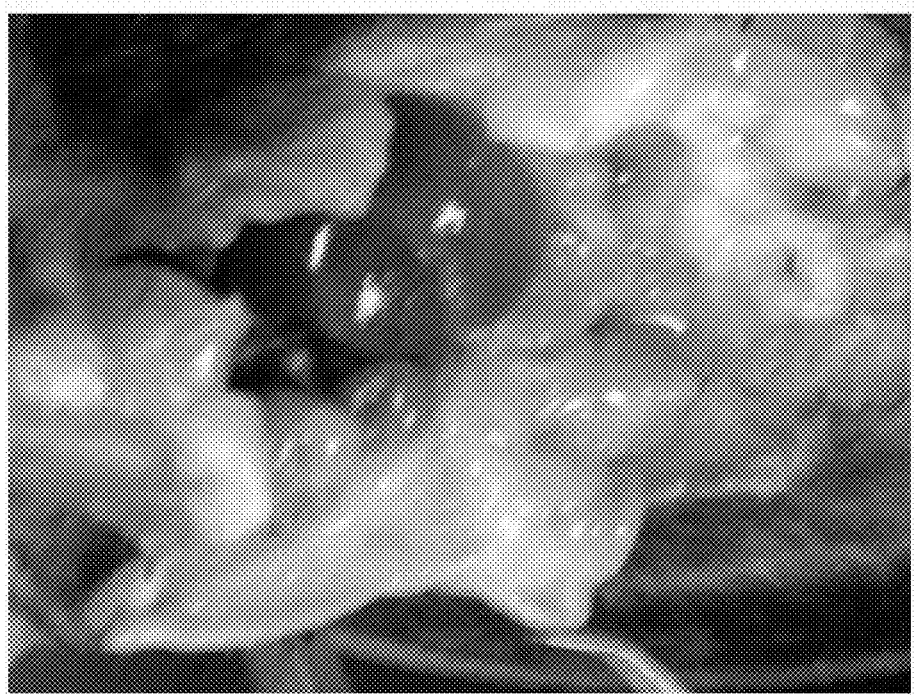

FIG. 8 is a set of two photographs comparing the omental fat found in a HFD-control mouse (left) with that of a HFD-mAb mouse (right). The fat is white, and much more fat is visible in the HFD-control mouse.

Taken together, the data showed that the administration of the monoclonal antibody antagonist that binds to GIP significantly reduced the amount of fat stored by the mice fed a high-fat diet. This included fat stored in the liver, the omentum, and under the skin.

Glucose Tolerance Tests

Materials and Methods

After 17 weeks on the special diets, six mice from each diet group were randomly selected for intraperitoneal glucose tolerance tests (IPGTTs). All animals were initially fasted for six hours before approximately 2 μL blood was collected from each animal's tail vein. These first samples represented baseline blood glucose levels or time zero on the IPGTT curve. Blood glucose was measured using a Truetest™ glucometer (NIPRO Diagnostics, Fort Lauderdale, Fla.).

Each mouse was then administered approximately 2 milligrams glucose per kg body weight by intraperitoneal injection. Glucose was delivered as a 20% solution in water. After administration, approximately 2 μL blood was collected from the tail vein of each mouse at times 10, 30, 60, and 120 minutes. Blood glucose concentration levels were measured and recorded.

Results

Figure 2:
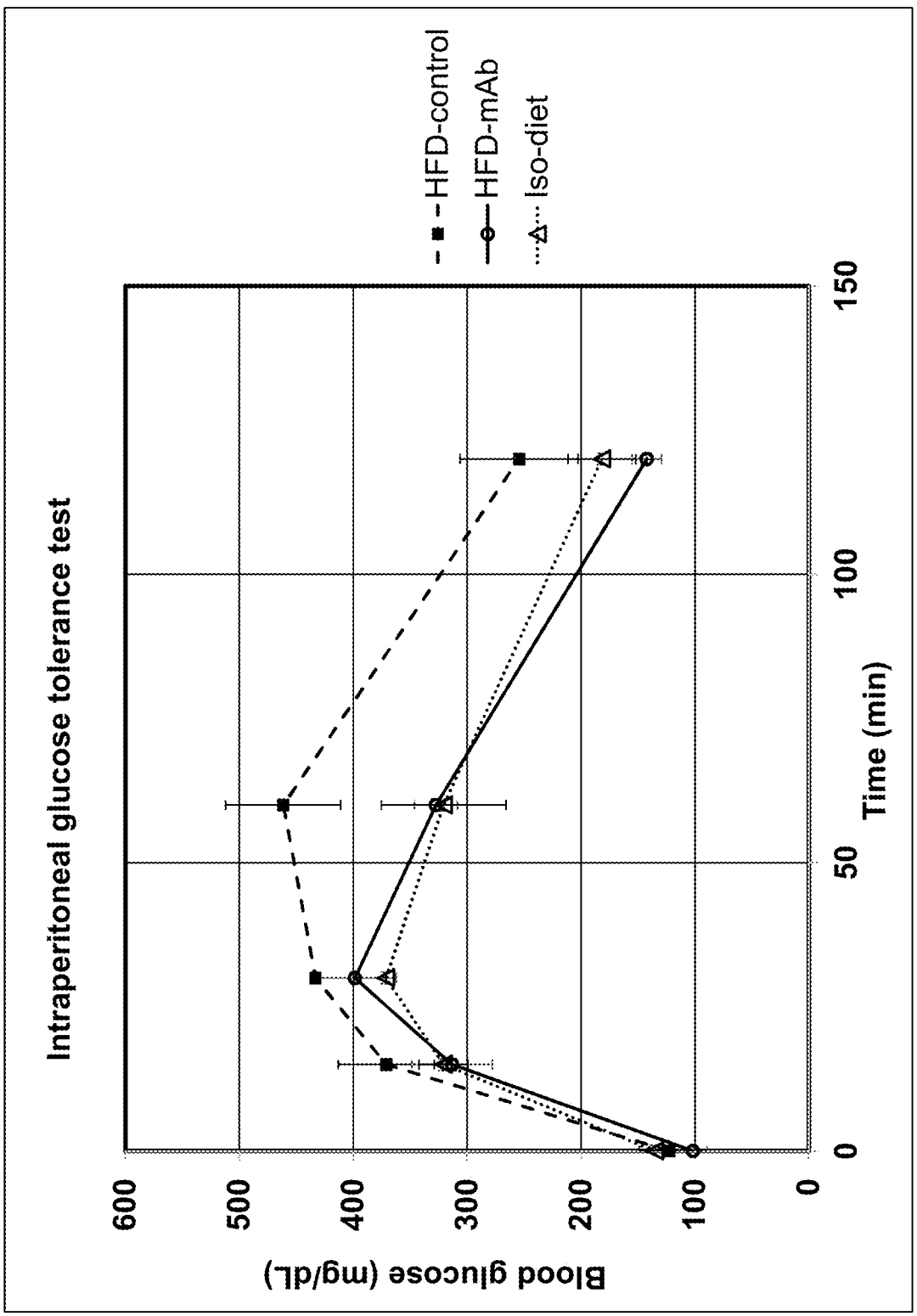
FIG. 2 is a graph showing the results of an intraperitoneal (i.p.) glucose tolerance test (IPGTT). After the 17-week study period, 6 mice from each group were subjected to IPGTT. After i.p. administration of a glucose solution (2 mg glucose/kg mouse weight), blood was collected at times 0, 10, 30, 60 and 120 minutes and glucose content was measured. Blood glucose concentration is plotted against time in the graph. HFD-control mice were less efficient than either HFD-mAB mice or Iso-diet mice in their ability to handle an i.p. glucose load. This is consistent with the development of glucose intolerance in the HFD-control mice, but not the HFD-mAb mice or Iso-diet mice.

The results are shown in FIG. 2. The serum glucose level in the HFD-control mice rose to a much higher concentration compared to the HFD-mAb mice and the Iso-diet mice. In addition, the serum glucose level in the HFD-mAb mice and the Iso-diet mice began decreasing much earlier. This is consistent with the development of glucose intolerance in the HFD-control mice, but not the HFD-mAb mice or the Iso-diet mice.

Blood Serum Measurements

Materials and Methods

After 17 weeks on the special diets, mice in the three groups were sacrificed. Whole blood was collected, serum was prepared, and the levels of many different components were measured.

Results

Figure 9:
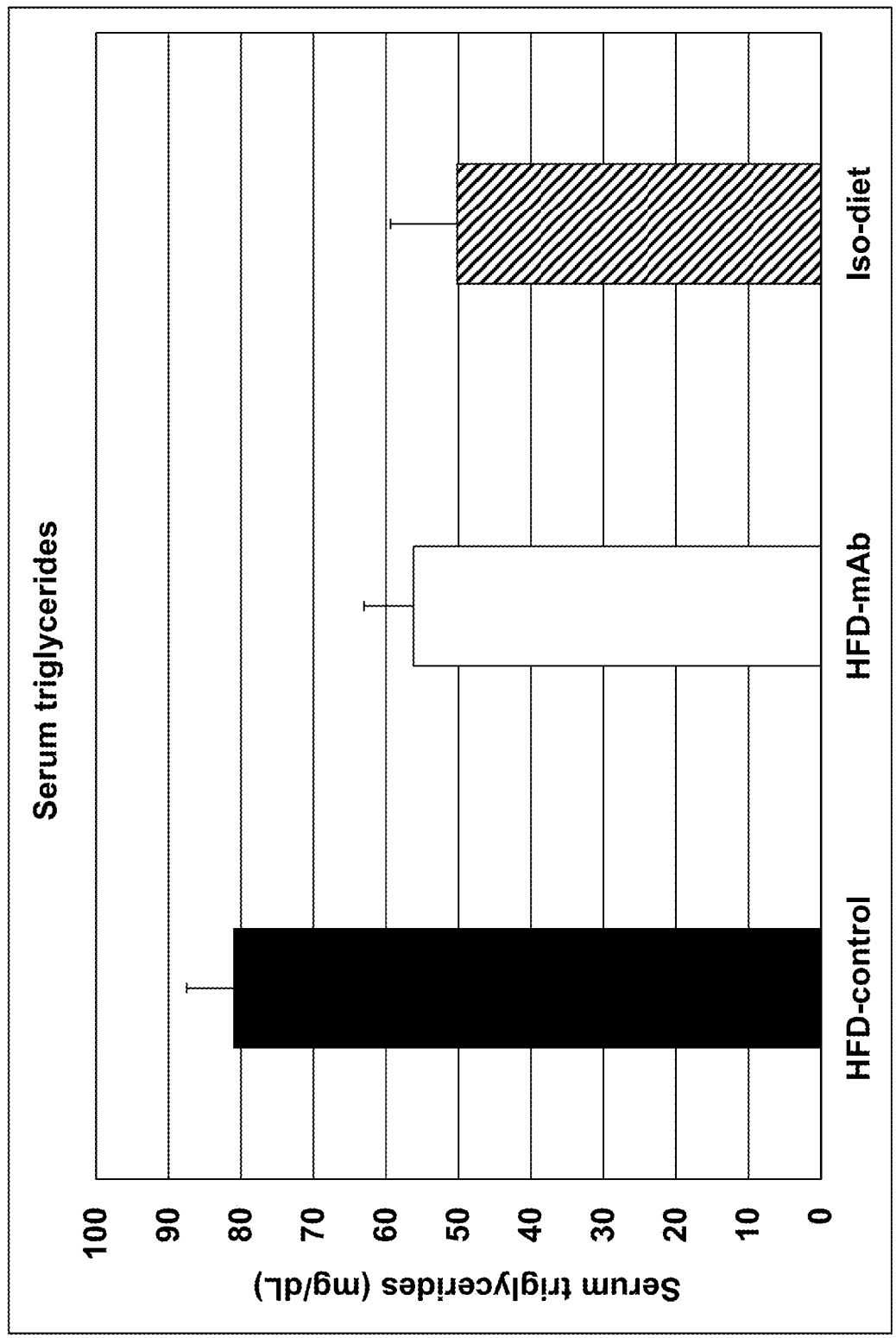
FIG. 9 shows triglyceride (TG) levels measured in the sera of mice. At the end of the 17-week diet period, mice were sacrificed, whole blood was collected, serum was prepared and serum triglycerides measured. The average serum TG levels for the mice in each group are plotted. TG levels in HFD-control mice were 1.44 times greater than TG levels in HFD-mAb mice (p=0.02). Higher TG levels are associated with obesity and metabolic syndrome.

FIG. 9 shows triglyceride (TG) levels measured in the sera of each group of mice. TG levels in HFD-control mice were 1.44 times greater than TG levels in HFD-mAb mice. Higher TG levels are associated with obesity and metabolic syndrome.

Figure 10:
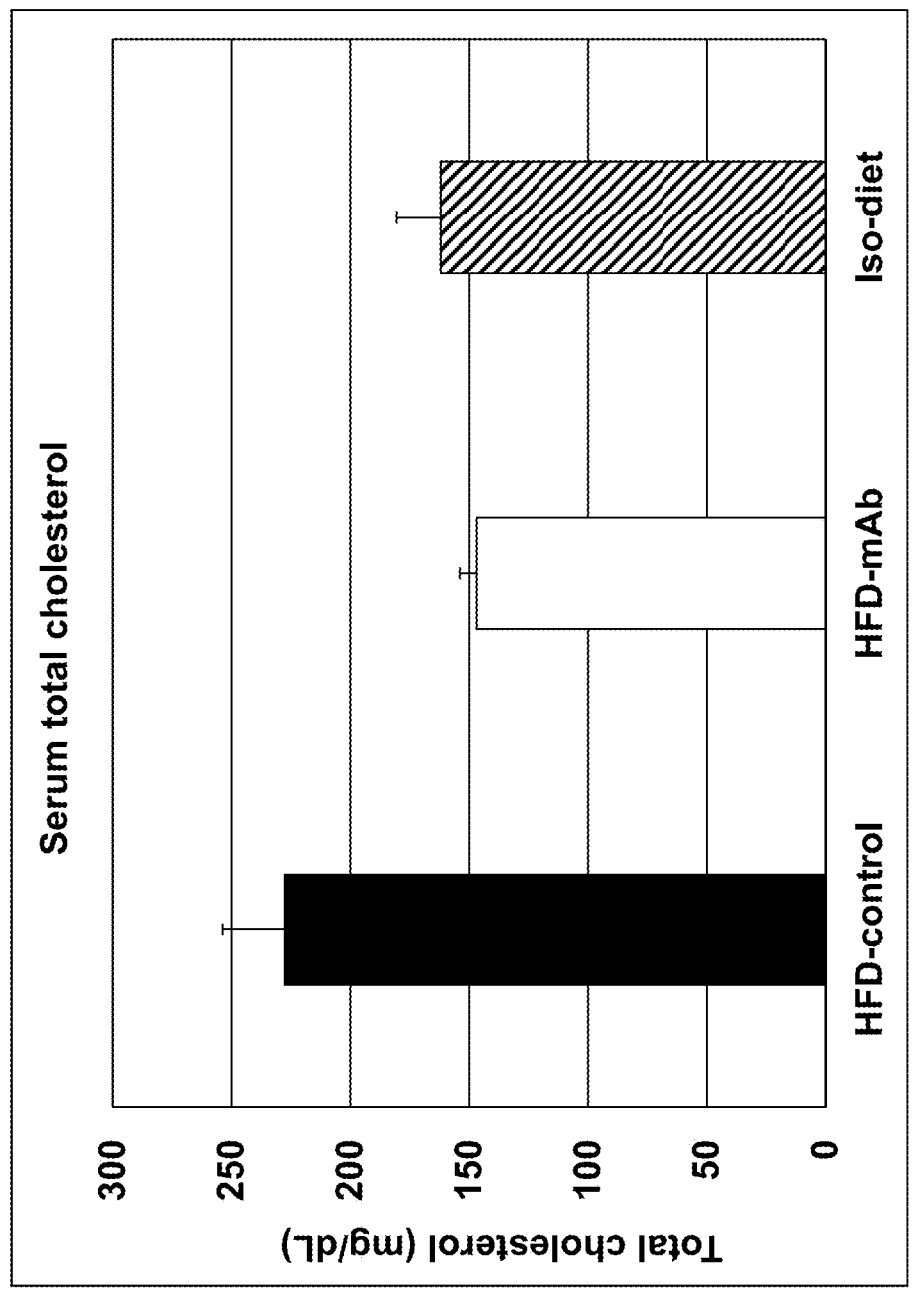
FIG. 10 shows total cholesterol (TC) levels measured in the sera of mice after the 17-week diet period. TC levels in HFD-control mice were 1.55 times greater than TC levels in HFD-mAb mice (p=0.006). Higher TC levels are associated with obesity and metabolic syndrome.

FIG. 10 shows average total cholesterol (TC) levels measured in the sera of each group of mice. TC levels in HFD-control mice were 1.55 times greater than TC levels in HFD-mAb mice. Higher TC levels are associated with obesity and metabolic syndrome.

Figure 11:
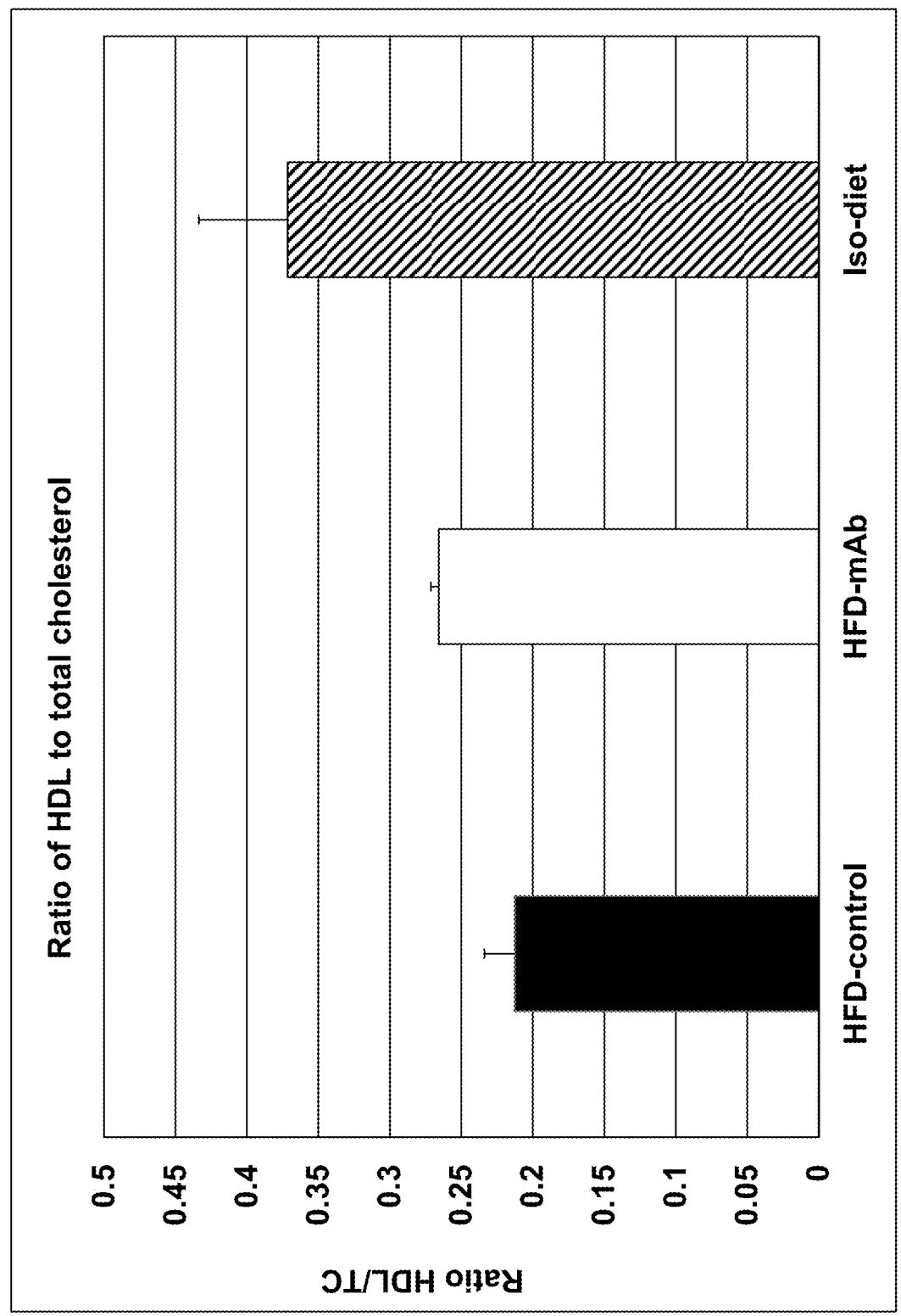
FIG. 11 shows the ratio of high-density lipoprotein (HDL) to total cholesterol (TC) measured in the sera of mice after the 17-week diet period. The average value for each group is plotted. The ratio of HDL to total cholesterol in HFD-mAb mice was 25% higher than the ratio of HDL to total cholesterol levels in HFD-control mice (p value=0.03). Higher ratios of HDL to total cholesterol levels are desirable as lower ratios are associated with obesity and metabolic syndrome.

FIG. 11 shows the average ratio of high-density lipoprotein (HDL) to total cholesterol (TC) measured in the sera of each group of mice. The ratio of HDL to total cholesterol in HFD-control mice was 20% lower than the ratio of HDL to total cholesterol levels in HFD-mAb mice. Lower ratios of HDL to total cholesterol levels are associated with obesity and metabolic syndrome.

Figure 12:
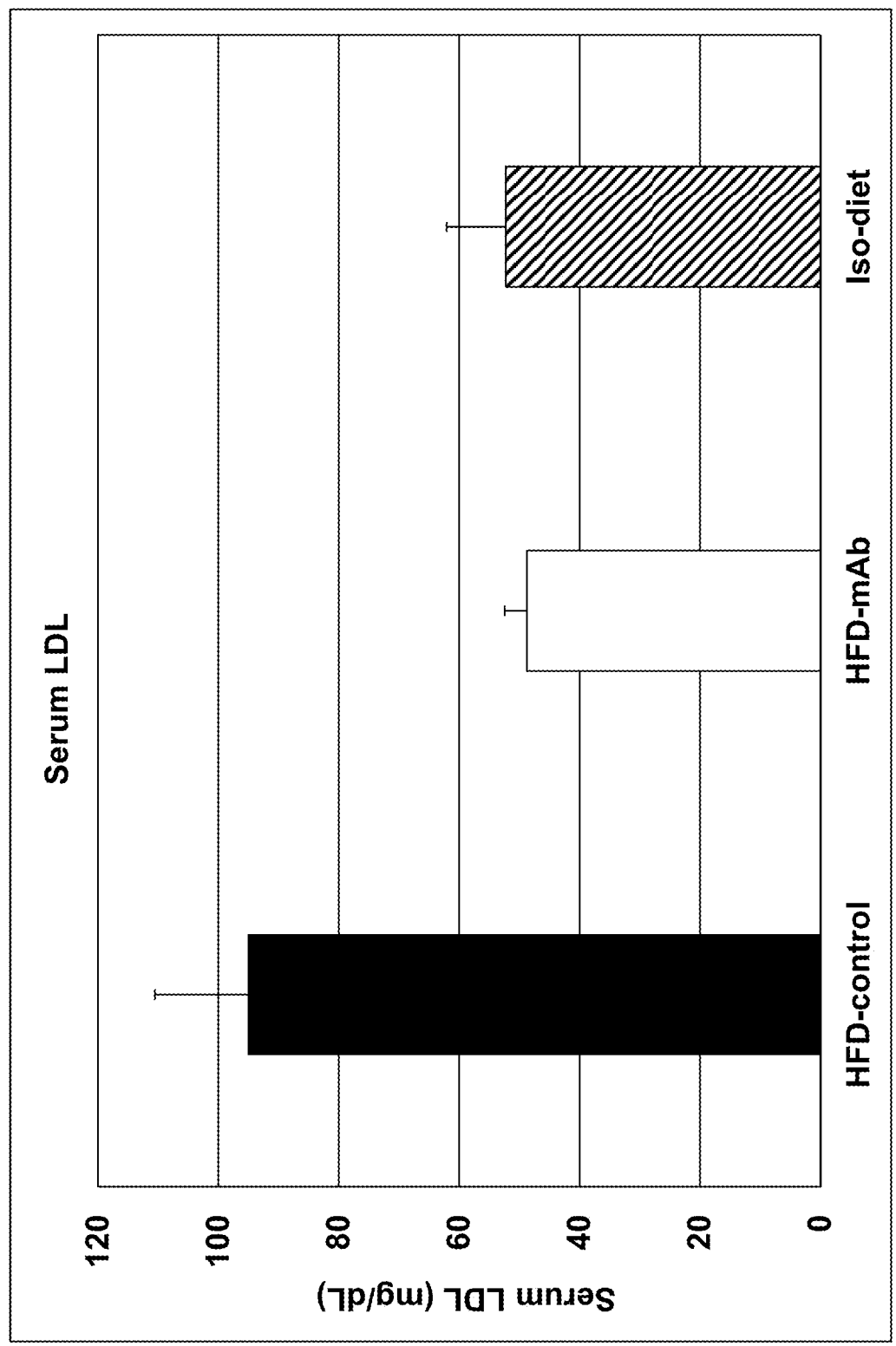
FIG. 12 shows low-density lipoprotein (LDL) levels measured in the sera of mice after the 17-week diet period. The average serum LDL levels for the mice in each group are plotted. LDL levels in HFD-control mice were 1.95 times greater than LDL levels in HFD-mAb mice (p=0.007). Higher LDL (the "bad" cholesterol) levels are associated with obesity and metabolic syndrome.

FIG. 12 shows average low-density lipoprotein (LDL) levels measured in the sera of each group of mice. LDL levels in HFD-control mice were 1.95 times greater than LDL levels in HFD-mAb mice. Higher LDL (the "bad" cholesterol) levels are associated with obesity and metabolic syndrome.

Figure 13:
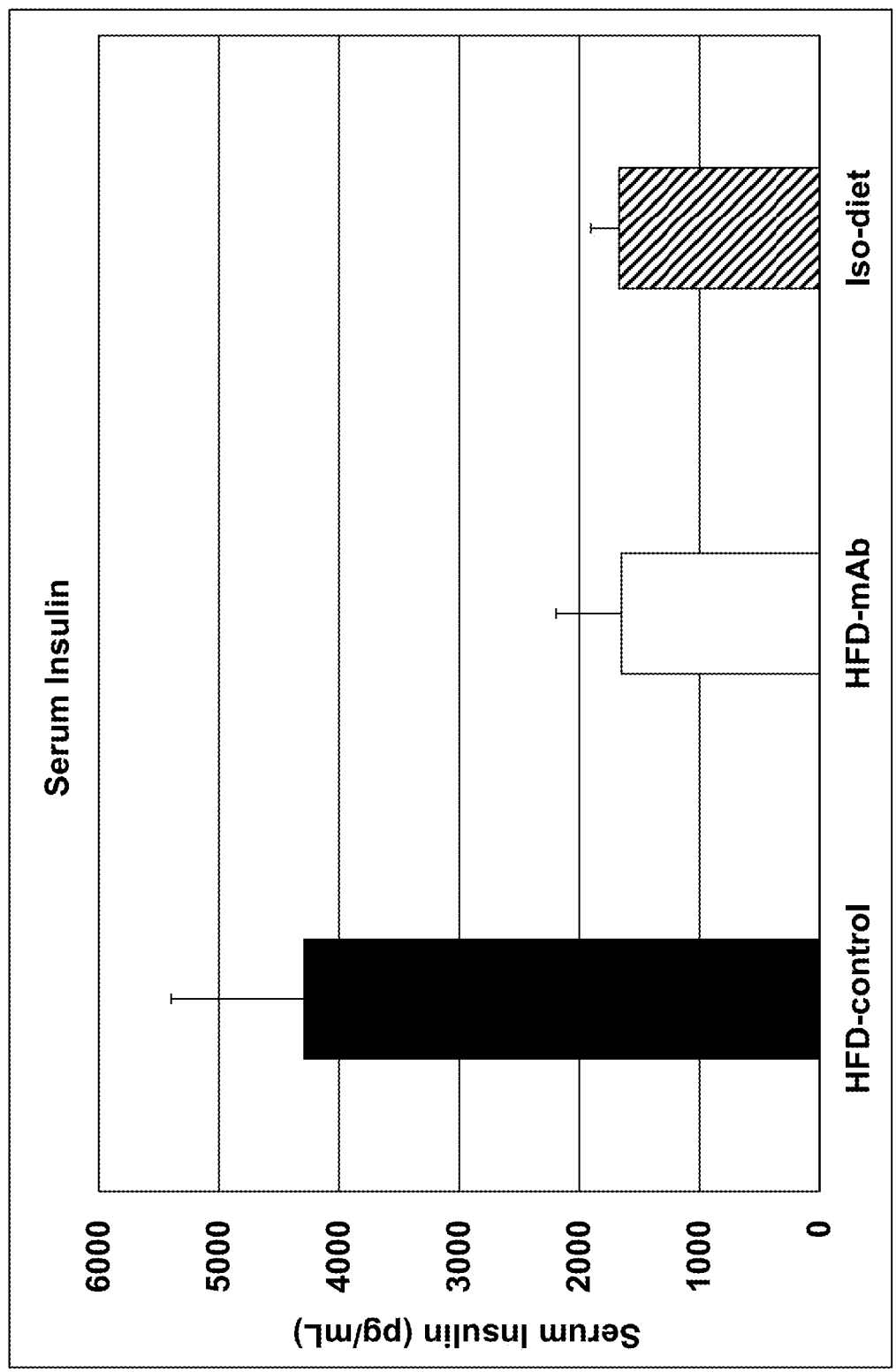
FIG. 13 shows insulin levels measured in the sera of mice after the 17-week diet period. The average serum insulin levels for 5 mice from each group are plotted. Insulin levels in HFD-control mice were 2.6 times greater than insulin levels in HFD-mAb mice (p=0.03). Higher insulin levels are associated with obesity, insulin resistance, and metabolic syndrome. Note the y-axis is in units of picograms/milliliter.

FIG. 13 shows average insulin levels measured in the sera of each group of mice. Insulin levels in HFD-control mice were 2.6 times greater than insulin levels in HFD-mAb mice. Higher insulin levels are associated with obesity, insulin resistance, and metabolic syndrome.

Figure 14:
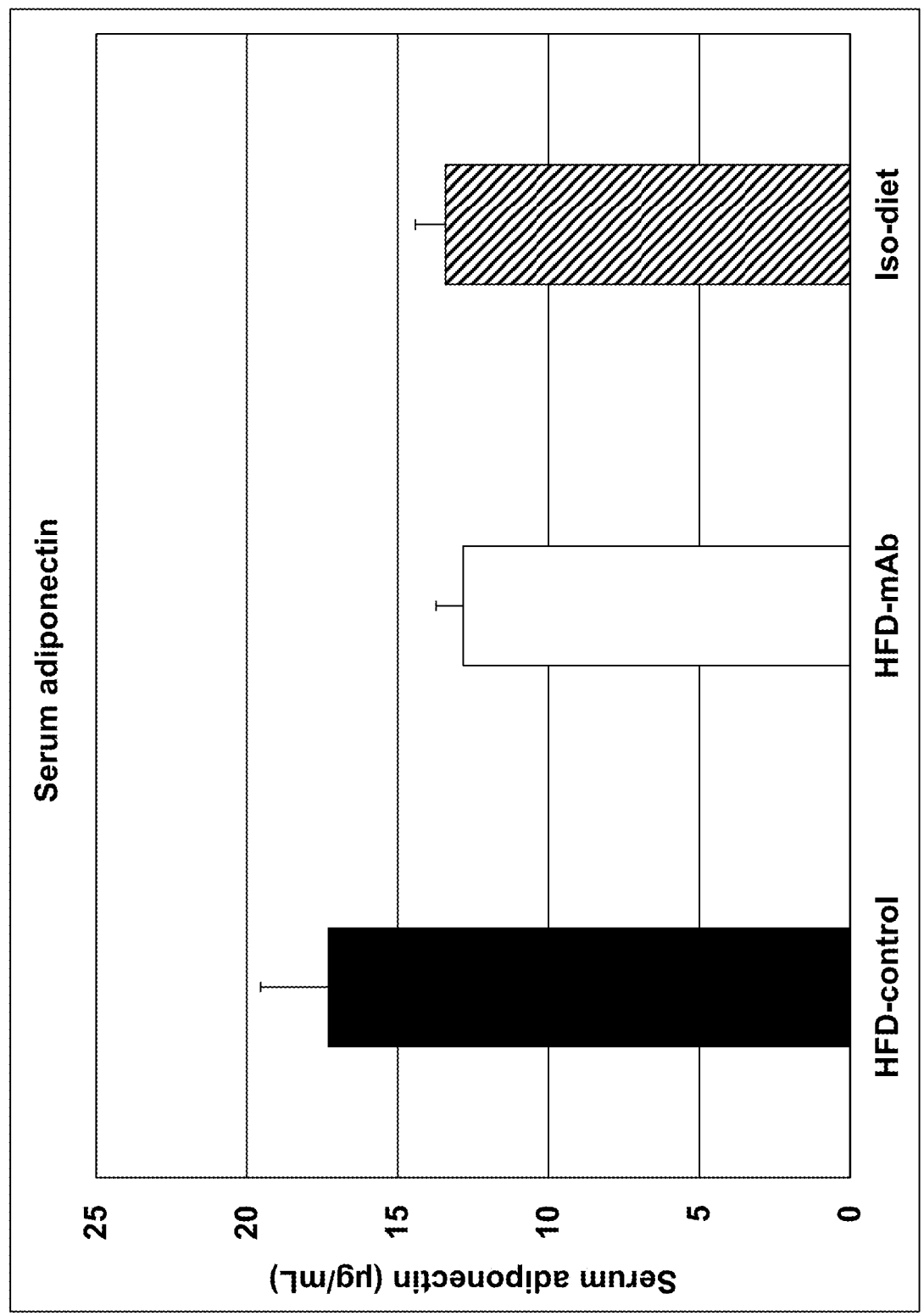
FIG. 14 shows adiponectin levels measured in the sera of mice after the 17-week diet period. The average serum adiponectin levels for the mice in each group are plotted. Adiponectin levels in HFD-control mice were 1.35 times greater than adiponectin levels in HFD-mAb mice. Higher adiponectin levels are associated with increased total body fat. Note the y-axis is in units of micrograms/milliliter.

FIG. 14 shows average adiponectin levels measured in the sera of each group of mice. Adiponectin levels in HFD-control mice were 1.35 times greater than adiponectin levels in HFD-mAb mice. Higher adiponectin levels are associated with increased total body fat.

Figure 15:
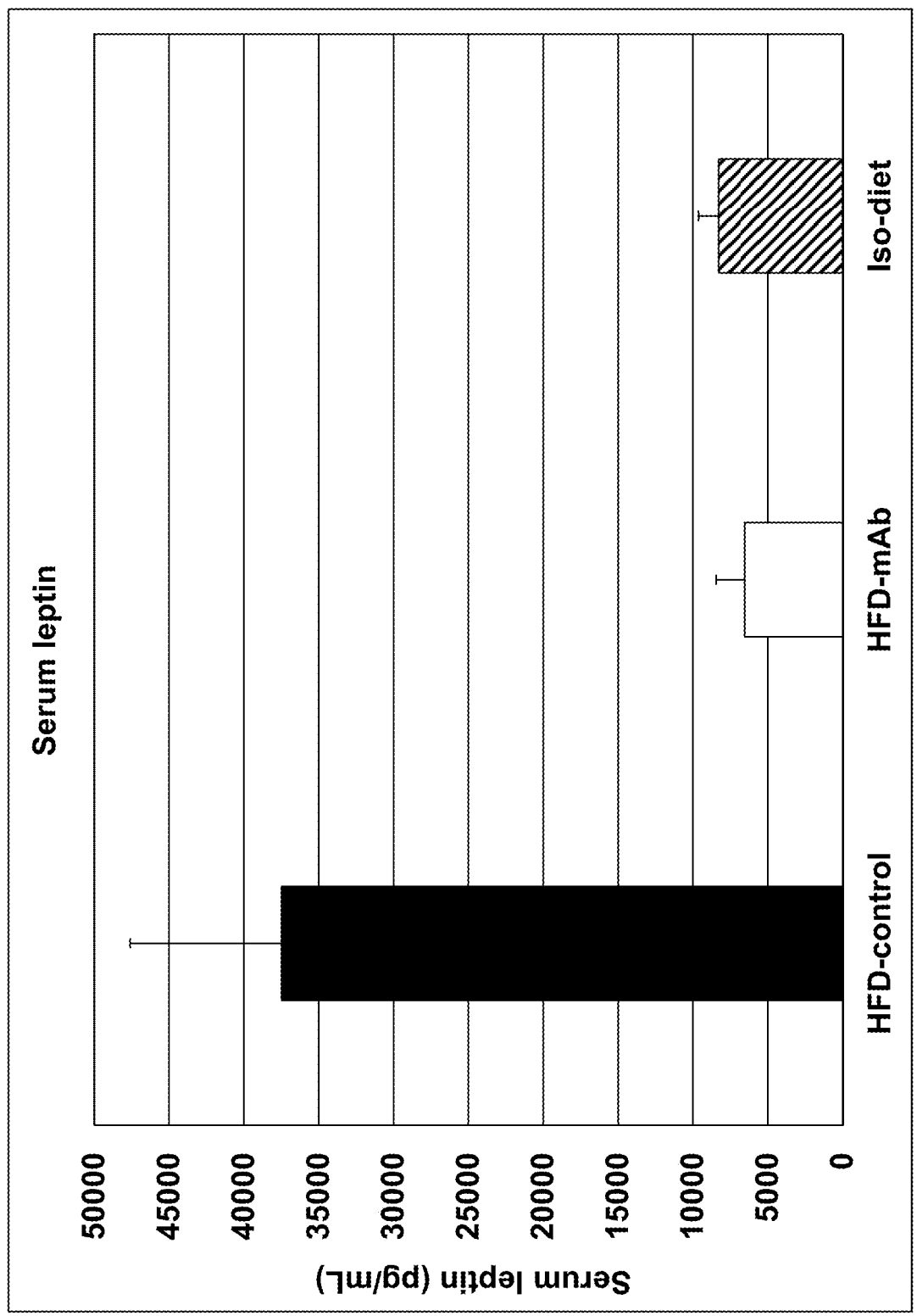
FIG. 15 shows leptin levels measured in the sera of mice after the 17-week diet period. The average serum leptin levels for the mice in each group are plotted. Leptin levels in HFD-control mice were 5.73 times greater than leptin levels in HFD-mAb mice (p=0.006). Higher leptin levels are associated with increased total body fat. Note the y-axis is in units of picograms/milliliter.

FIG. 15 shows average leptin levels measured in the sera of each group of mice. Leptin levels in HFD-control mice were 5.73 times greater than leptin levels in HFD-mAb mice. Higher leptin levels are associated with increased total body fat.

Figure 16:
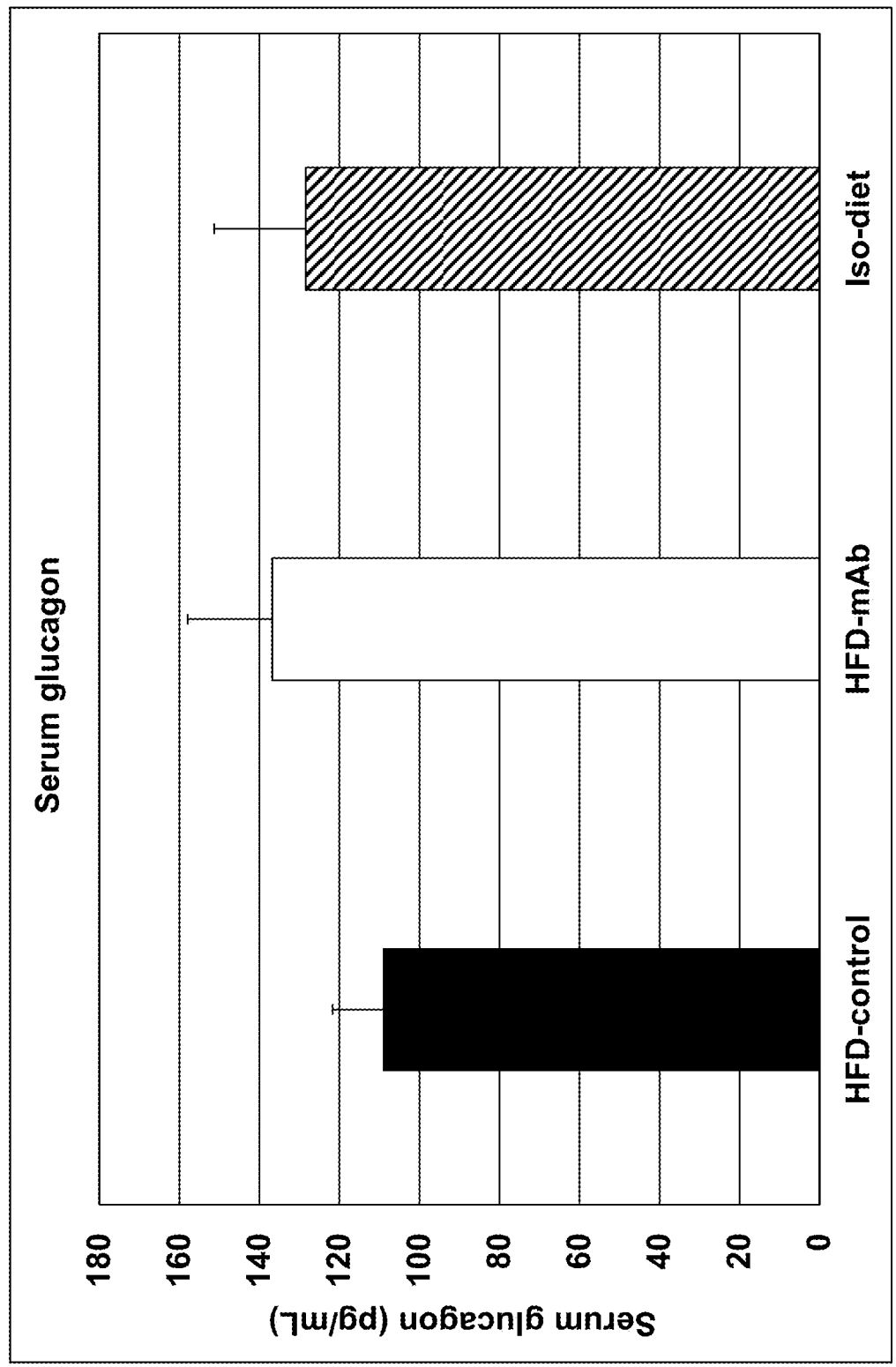
FIG. 16 shows glucagon levels measured in the sera of mice after the 17-week diet period. The average serum glucagon levels for the mice in each group are plotted above. There was no significant difference in the levels of serum glucagon between the groups. Note the y-axis is in units of picograms/milliliter.

FIG. 16 shows average glucagon levels measured in the sera of each group of mice. There was no significant difference in the levels of serum glucagon between the groups.

Figure 17:
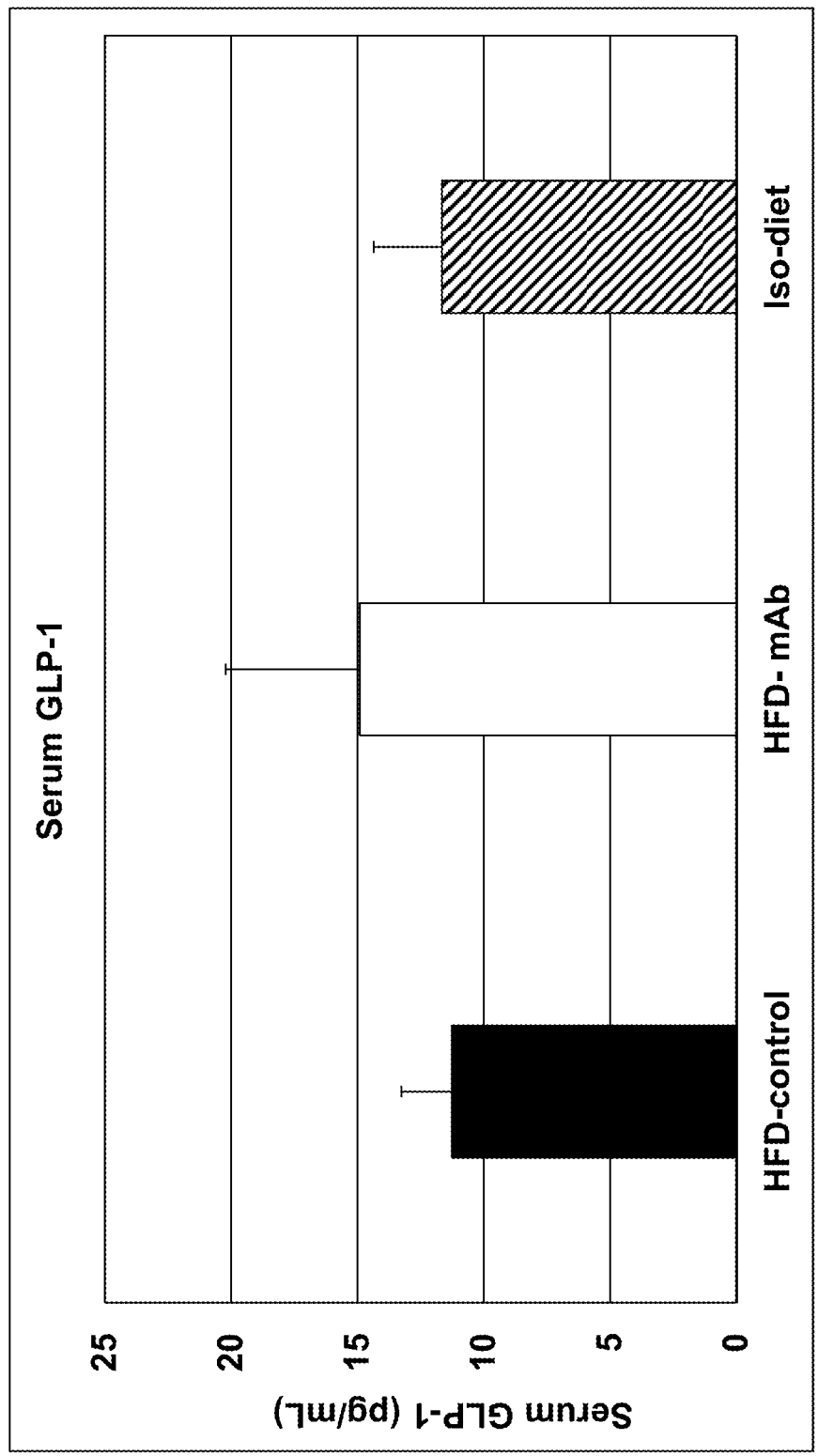
FIG. 17 shows glucagon-like peptide 1 (GLP-1) levels measured in the sera of mice after the 17-week diet period. The average serum GLP-1 levels for the mice in each group are plotted. There was no significant difference in the levels of serum GLP-1 between the groups. Note the y-axis is in units of picograms/milliliter.

FIG. 17 shows average glucagon-like peptide 1 (GLP-1) levels measured in the sera of each group of mice. There was no significant difference in the levels of serum GLP-1 between the groups.

Taken together, this data showed that the administration of the monoclonal antibody antagonist that binds to GIP significantly improved all of the markers associated with obesity and metabolic syndrome. This data suggests that administration of the mAb can reduce the complications associated with obesity and metabolic syndrome. The fact that there was no change in the levels of serum glucagon or GLP-1 indicated that the mAb was specific to GIP, and suggests that there should be few (if any) side effects from the inhibition of glucagon or GLP-1, which share some common biological pathways with GIP but which also have other biological effects not shared in common with GIP.

Discussion

The results of these experiments showed that intraperitoneally delivered monoclonal antibodies that bind to GIP can significantly reduce adipose tissue accumulation and fat accumulation in liver. The mice fed a high-fat diet (HFD) while receiving the GIP mAb showed markedly less fat content than the HFD-control mice. A reduction in fat content was seen in the liver, the omentum, and in the subcutaneous fat fraction. This indicates that moderate amounts of the GIP mAb antagonist can reduce or prevent the accumulation of fat in tissue by inhibiting GIP. Inhibition of GIP reduces intestinal glucose uptake, reduces intestinal peptide uptake, reduces postprandial insulin secretion, reduces glucose uptake in adipocytes, increases lipolysis, and inhibits nutrient uptake. The change in serum levels of the markers associated with obesity and metabolic syndrome also indicates that the GIP mAb antagonist can be useful against the health consequences of those conditions.

Example 3: Modification of Antibodies

The light chain variable region of the 10g10 mAb was further modified by substituting specific amino acids conserved in mouse antibodies with specific amino acids conserved in human antibodies. This was done to "humanize" the light chain variable region to make it more similar to a human variable region, and increase the chance that the human immune system would not recognize the "humanized" mAb as a foreign substance. To humanize the light chain variable region, oligonucleotides were chemically synthesized. The sequences of the oliogonucleotides were similar to the sequence of the 10g10 mAb light chain variable region, except specific bases were changed. The base pairs changed were predicted to change specific amino acids of the light chain variable region when the sequence was translated into protein. A DNA synthesis reaction was used to produce double-stranded (ds) DNA. Three different ds-oligonucleotides were synthesized and then digested with the restriction endonucleases HindIII and NotI, before being ligated into a mammalian expression vector. The mammalian expression vector contained a signal sequence and the constant region of a human light chain. The ds-oligonucleotides were ligated to the vector in such a way that the variable region and the constant region, when expressed as mRNA and then translated into protein, would generate an antibody light chain.

The three resulting humanized light chains are referred to as LC1, LC2, and LC3 herein. The amino acid sequence of LC1 is SEQ ID NO: 17, and the cDNA sequence for LC1 is SEQ ID NO: 36. The amino acid sequence of LC2 is SEQ ID NO: 18, and the cDNA sequence for LC1 is SEQ ID NO: 37. The amino acid sequence of LC3 is SEQ ID NO: 19, and the cDNA sequence for LC1 is SEQ ID NO: 38.

The heavy chain variable region of the 10g10 mAb was also further modified in the same manner. Again, the base pairs changed were predicted to change specific amino acids of the heavy chain variable region when the sequence was translated into protein. Three different ds-oligonucleotides for the chain were synthesized and then ligated into a mammalian expression vector. The mammalian expression vector contained a signal sequence and the constant region of a human heavy chain. The ds-oligonucleotides were ligated to the vector in such a way that the variable region and the constant region, when expressed as mRNA and then translated into protein, would generate an antibody heavy chain.

The three resulting humanized heavy chains are referred to as HC1, HC2, and HC3 herein. The amino acid sequence of HC1 is SEQ ID NO: 28, and the cDNA sequence for HC1 is SEQ ID NO: 40. The amino acid sequence of HC2 is SEQ ID NO: 29, and the cDNA sequence for HC1 is SEQ ID NO: 41. The amino acid sequence of HC3 is SEQ ID NO: 30, and the cDNA sequence for HC1 is SEQ ID NO: 42.

Monoclonal antibodies (mAbs) containing the humanized light chain variable regions and heavy chain variable regions were produced in CHO cells. A mammalian vector possessing the coding sequence for an antibody light chain was co-transfected with a mammalian vector possessing the coding sequence for an antibody heavy chain. A total of 9 unique combinations were transfected into CHO cells: LC1/HC1, LC1/HC2, LC1/HC3, LC2/HC1, LC2/HC2, LC2/HC3, LC3/HC1, LC3/HC2, and LC3/HC3. Monoclonal antibodies derived from these combinations were compared to the 10g10 mAb.

CHO cells co-transfected with the mammalian expression vectors were grown in culture and the supernate collected. The supernate was evaluated for the presence of GIP-binding mAbs by direct binding ELISA. Human GIP was fixed to the bottom of the wells on 96-well plates. Serial dilutions of the supernate were added to different wells of the 96-well plate. After a one hour incubation, the wells were washed twice with PBS before a secondary antibody that specifically binds to human IgG was added to each well. The antibody that specifically binds to human IgG was conjugated with the enzyme horse radish peroxidase (HRP). After incubation for one hour, the wells were washed with PBS before the HRP substrate was added. If HRP was present in a well, the substrate was converted to a colored compound. The amount of color intensity was read using a spectrophotometer. The amount of color produced was proportional to the amount of HRP-antibody conjugate remaining in each well. The amount of color produced was also proportional to the amount of mAb bound to hGIP in each well.

The results of this evaluation indicated that the various combinations of the light chain/heavy chain vectors bound human GIP in the following order (highest binding affinity to lowest binding affinity): LC2/HC1, LC2/HC2, LC3/HC2, LC1/HC2, LC2/HC3, LC3/HC1, LC1/HC1, 10g10, LC1/HC3, and LC3/HC3.

Antibodies produced in 100 ml suspension cultures of CHO cells co-transfected with the combination of expression vectors of LC2/HC1, LC2/HC2, and LC2/HC3 were purified using Protein A agarose. Each light chain (LC1, LC2, LC3) and each heavy chain (HC1, HC2, HC3) also individually displayed the ability to specifically bind to GIP.

Next, the ability of these three purified mAbs to neutralize hGIP and prevent ligand-receptor interaction, receptor activation and receptor-dependent signaling was tested using a cell culture system. This system used reporter cells (LGIPR3a cells), which possess the lacZ gene under the control of a cyclic adenosine monophosphate (cAMP)-responsive promoter and expresses the rat GIPR on the cell surface. The addition of GIP to these cells leads to activation of the GIPR, induction of a signaling cascade that leads to accumulation of cAMP, induction of the lacZ gene and synthesis of β-galactosidase. After the addition of a test sample and incubation for 4 hours, a colorimetric assay was used to measure β-galactosidase content in cell lysates. The degree of color change was proportional to the level of 3-galactosidase activity. The level of 3-galactosidase activity was dependent on the amount of free biologically active GIP in the test sample.

Figure 18:
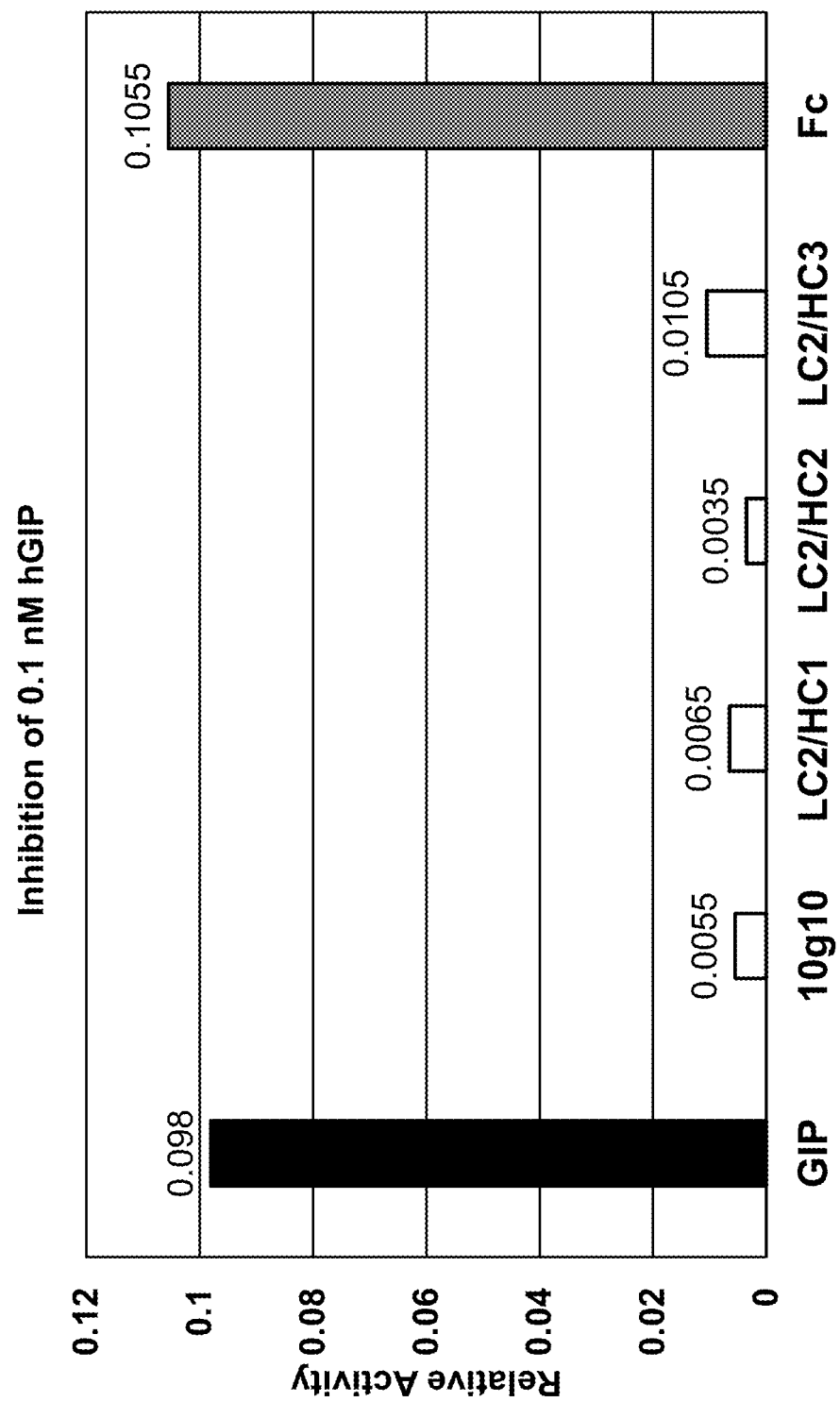
FIG. 18 is a graph showing the relative activity of three humanized antibodies for GIP, along with the original antibody, a positive control, and a negative control, in an in vitro neutralization assay. The y-axis is the relative activity, and is unitless.

The mAbs were mixed with a solution of human GIP (hGIP) in DMEM media at final concentrations of 25 g/ml for the mAb and 0.1 nM for hGIP. The mixtures were then added to LGIPR3a cells and incubated before washing and assaying for β-galactosidase. The results are shown in FIG. 18. 10g10 represents the original mouse mAb. The GIP acted as a positive control. Fc represents purified human Fc fragment, which acted as a negative control.

The results showed that the humanized antibodies neutralized hGIP in vitro similar to the 10g10 mouse mAb. The LC2/HC2 humanized antibody was the most effective of the three humanized mAbs. It was also more effective than the original mouse mAb. A lower relative activity is desired here, and the LC2/HC2 had a relative activity of 0.0035, versus 0.0055 for the 10g10 mouse mAb.

The complementarity determining regions (CDRs) of the variable regions of the six humanized light chains (LC1, LC2, LC3) and heavy chains (HC1, HC2, HC3) was also determined. LC1 had the CDRs of SEQ ID NO: 20, SEQ ID NO: 23, and SEQ ID NO: 22. LC2 had the CDRs of SEQ ID NO: 20, SEQ ID NO: 21, and SEQ ID NO: 22. LC3 had the CDRs of SEQ ID NO: 20, SEQ ID NO: 24, and SEQ ID NO: 22. HC1, HC2, and HC3 all had the same CDRs, which were SEQ ID NO: 31, SEQ ID NO: 32, and SEQ ID NO: 33.

Example 4: Inducement of Weight Loss

A weight-loss experiment was performed to determine whether the 10g10 antibody could reverse obesity in mice fed a high-fat diet (HFD). The 10g10 antibody is also referred to as the $mAb_m$ in this example.

C57BL/6 mice that were fed a HFD (60% calories from fat) from weaning to 18 wks to induce obesity were purchased from Jackson Laboratories. The mice were then changed to a HFD with 45% calories from fat and were administered either the GIP-binding $mAb_m$ (45 mg/kg body weight [BW]) (n=8) or an equivalent volume of PBS as control vehicle (n=9) by intraperitoneal (ip) injection weekly. The mice were continued on the HFD with 45% calories from fat for the duration of the experiment. BW and food consumption were recorded once per week.

At the onset of treatment, mouse weight ranged from 40.0 grams to 58.2 grams. The average weight for the control mice was 47.8±1.5 grams. The average weight for the mAb-treated mice was 47.9±2.2 grams.

Administration of the GIP-binding monoclonal antibody $mAb_m$ after five weeks resulted in a 4.2%±1.5% weight loss, while control mice showed a 2.0%±1.3% weight gain (P<0.007). When corrected for BW, the difference in food consumption between the mAb treated mice and the control mice was not significant.

Figure 19:
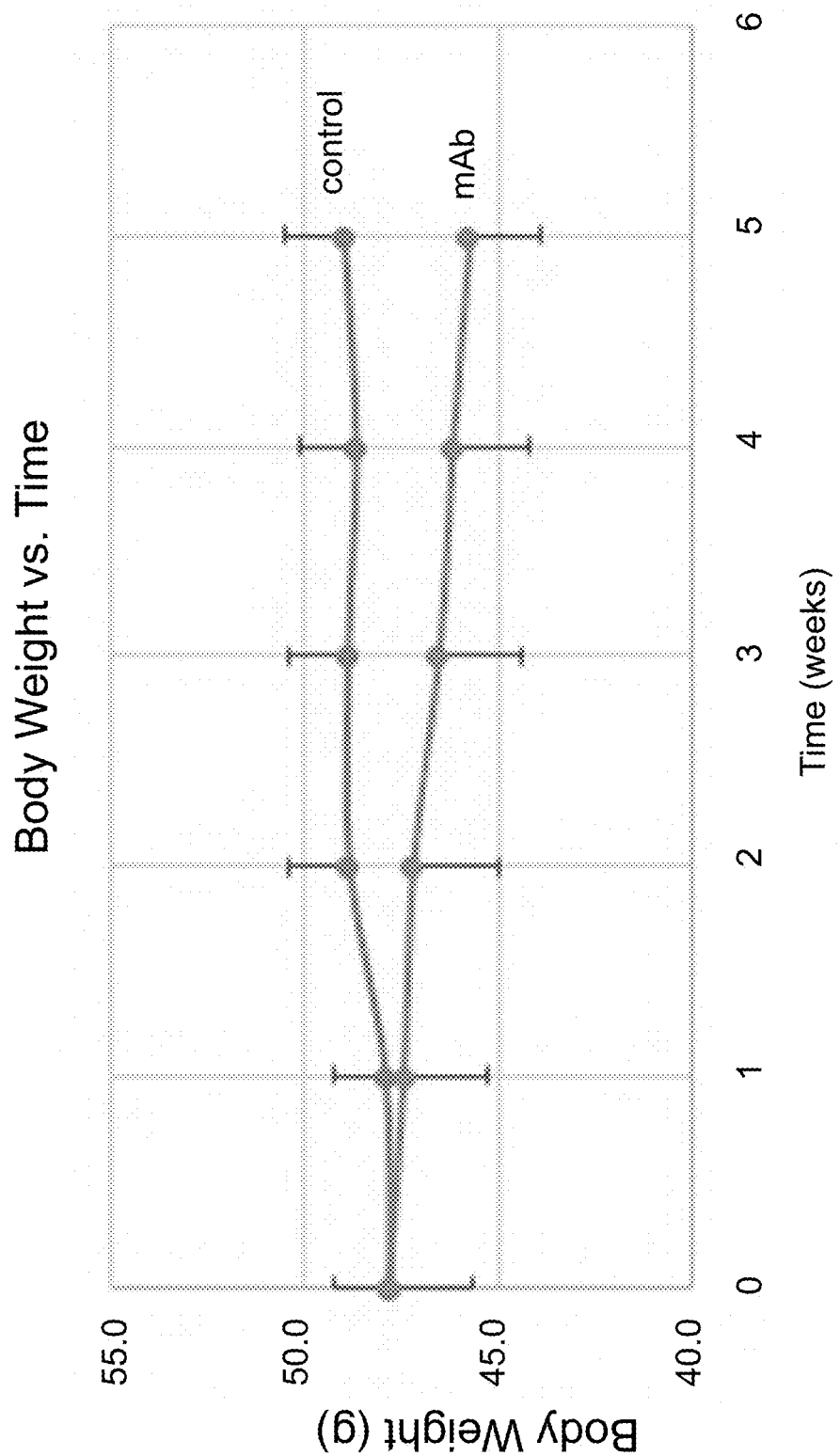
FIG. 19 is a graph showing body weight (grams) versus time for a weight loss experiment in mice after five weeks. The y-axis runs from 40.0 to 55.0 in increments of 5. The top line (with higher weights) is for control mice, while the bottom line (with lower weights) is for the "mAb" mice that were administered, by intraperitoneal injection, the monoclonal antibody antagonist of gastric inhibitory polypeptide (GIP mAb) in PBS at 45 mg/kg body weight (BW) per week.

FIG. 19 is a graph showing the average body weight over a five-week period.

Figure 20:
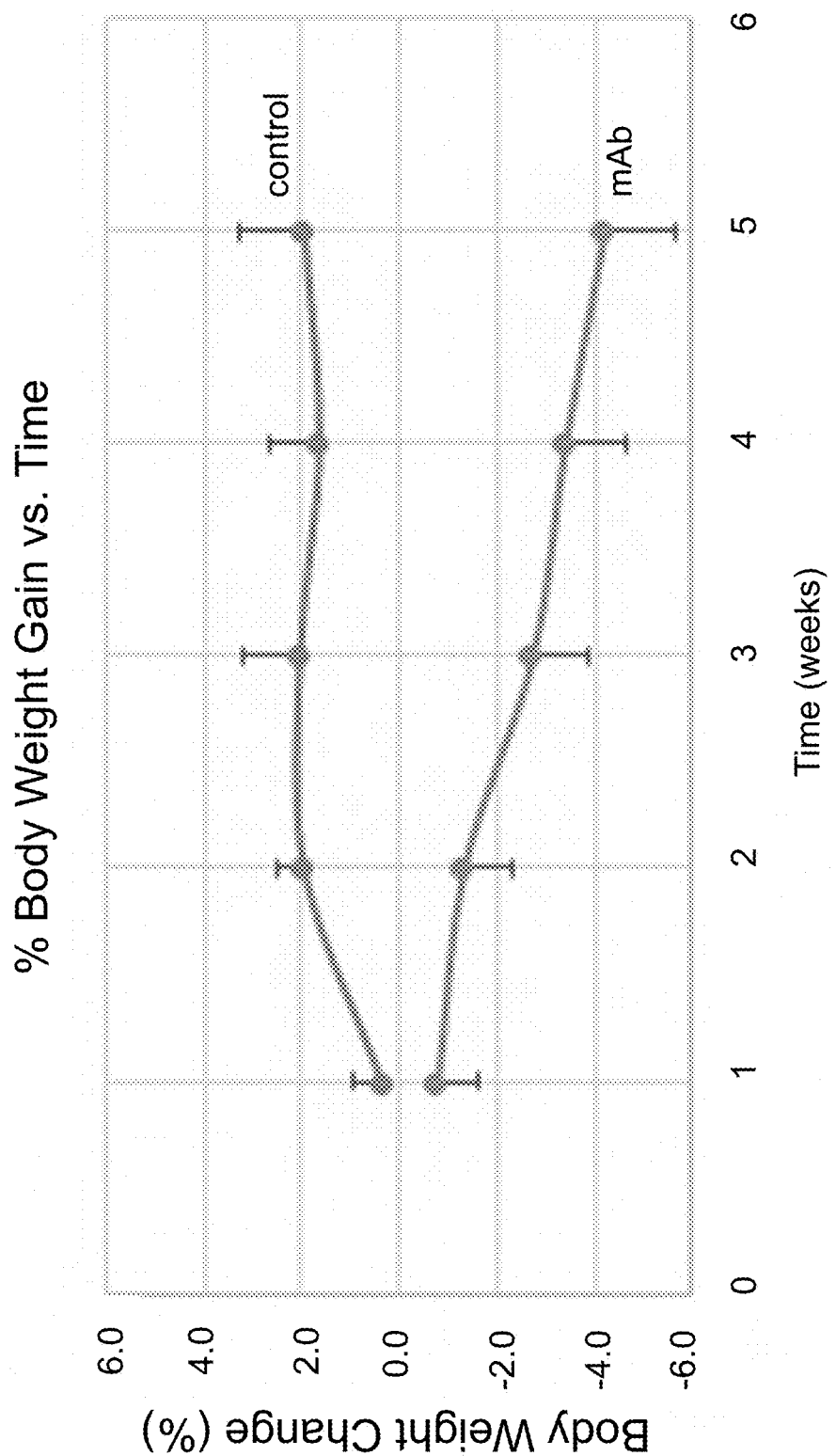
FIG. 20 is a graph showing % body weight change, compared to original body weight, (grams) versus time for the weight loss experiment in mice after five weeks. The y-axis runs from −6.0% to +6.0% in increments of 2. The top line (with higher weights) is for control mice, while the bottom line (with lower weights) is for the "mAb" mice.
Figure 21:
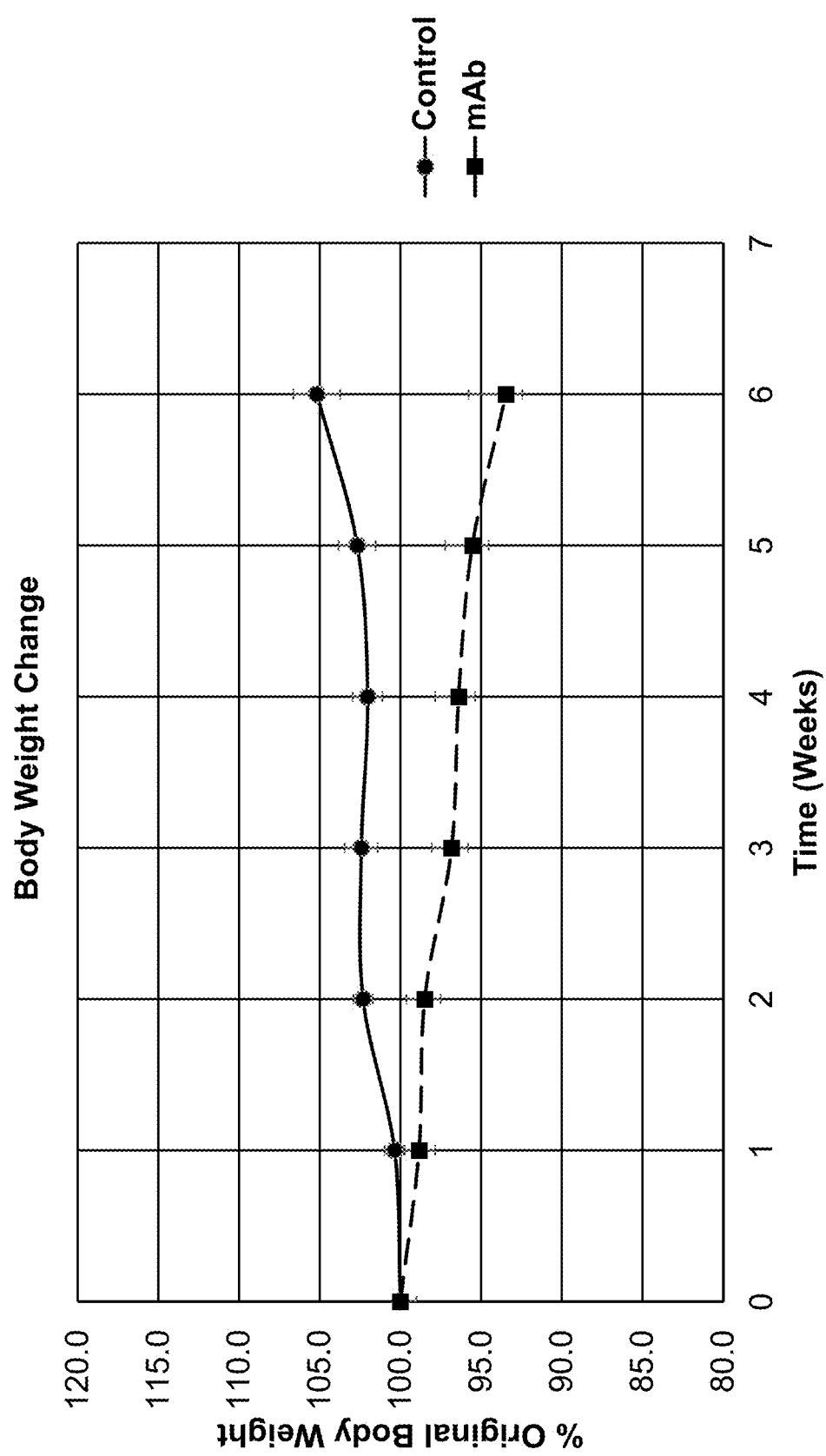
FIG. 21 is a graph showing the weight change in % of original body weight versus time for the weight loss experiment in mice after six weeks. The y-axis runs from 80% to 120% in increments of 5. The top line (with higher weights) is for control mice, while the bottom line (with lower weights) is for the "mAb" mice.

FIG. 20 is a graph showing the % body weight gain over a five-week period.

FIG. 20 is a graph showing the % weight change relative to original body weight after six weeks.

Student's 2-tailed t-tests were performed on the weights measured between the groups and within each group after five weeks. Three tests were performed. First, the average weight of the control mice was compared to the average weight of the mAb-treated mice for the given week. Second, the average weight for the control mice at week 0 was compared to the average weight at the given week. Second, the average weight for the mAb-treated mice at week 0 was compared to the average weight at the given week. The p-values for these comparisons are provided in the following table,

| Week | Control v. mAb (p) | Control mice, Week 0 vs. subsequent week (p) | mAb-treated mice, Week 0 vs. subsequent week (p) |
|---|---|---|---|
| 1 | 0.27487 | 0.55127 | 0.03269 |
| 2 | 0.00628 | 0.00136 | 0.18564 |
| 3 | 0.00425 | 0.02998 | 0.02349 |
| 4 | 0.00336 | 0.04410 | 0.01296 |
| 5 | 0.00219 | 0.03269 | 0.00938 |

The first column of p-values shows that the change in body weight between the control mice and the mAb-treated mice are very significant. The third column of p-values shows that the change in body weight of the mAb-treated mice over time is significant as well.

Example 5

Figure 22:
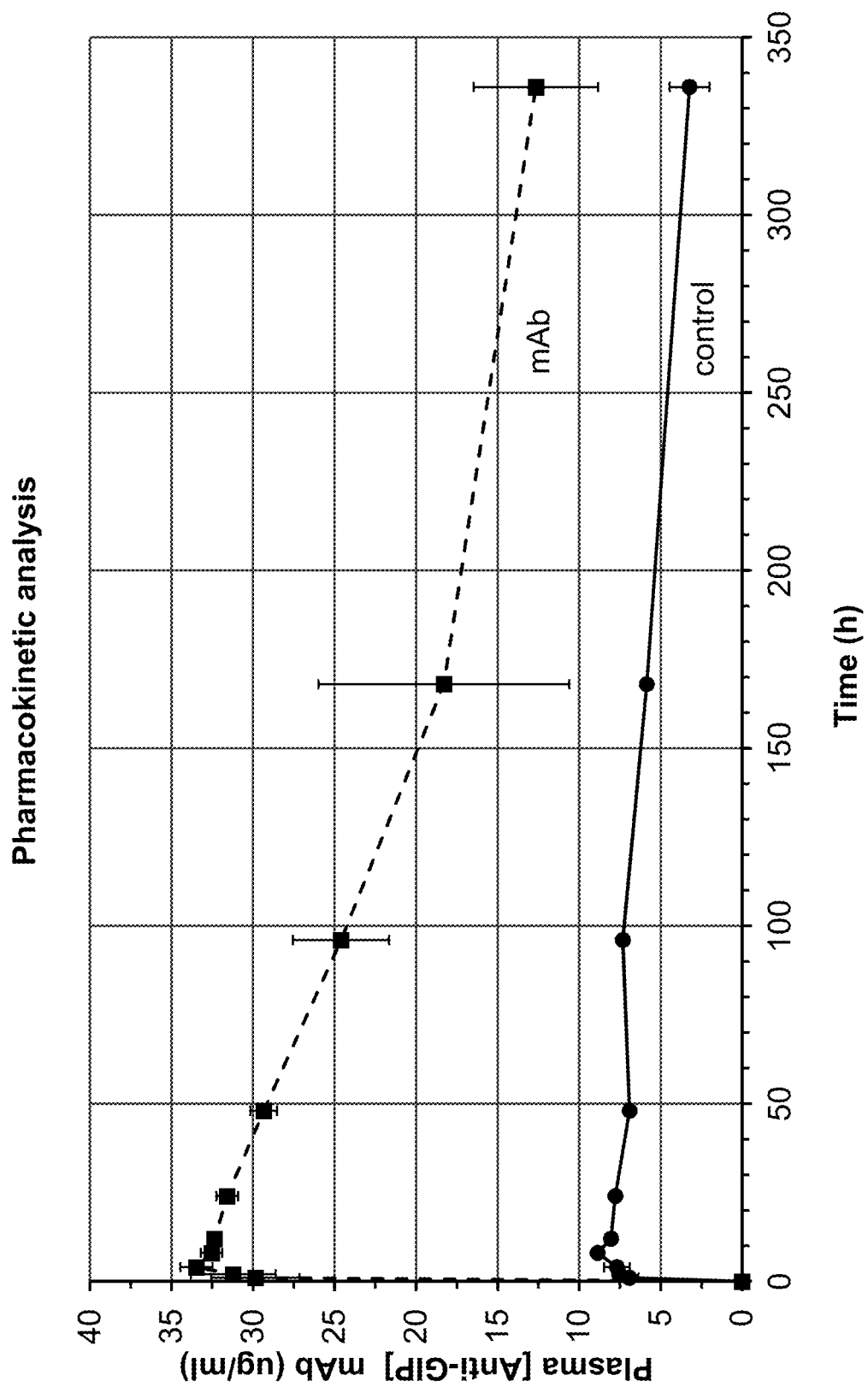
FIG. 22 is a graph showing the amount of anti-GIP antibody in plasma over time for control mice and "mAb" mice. The y-axis is in units of micrograms per milliliter (µg/mL), and runs from 0 to 40 in increments of 5. The x-axis is time in hours, and runs from 0 to 350 hours in increments of 50. The top line is for the "mAb" mice, and the bottom line is for the control mice.

In separate studies, the LC2/HC2 humanized antibody ($mAb_H$) was compared to the 10g10 antibody ($mAb_m$). Binding affinity was determined by surface plasmon resonance, and a reporter cell line expressing GIP receptors was used in a modified Schild's assay to demonstrate mAb-dependent GIP neutralization in vitro. Finally, the GIP $mAb_H$ (10 or 30 mg/kg BW) was administered to C57BL/6 mice intraperitoneally. Blood samples were collected immediately before injection (time 0) and at times 1, 2 4, 8 and 12 hours after injection and also 1, 2, 4, 7 and 14 days after injection. Blood was diluted in 1 mM EDTA and centrifuged for 1 minute at 20,000 gravities to remove cells and the diluted plasma samples were assayed for bioavailable humanized anti-GIP mAb using a specific ELISA. The $C_{max}$ and $T_{½}$ were determined, and the results are shown in FIG. 22. For each time point, the average of 4 mice±SE is presented. $T_{½}$ is about nine days.

In separate studies, mice fasted for 1 hour were administered either 30 mg/kg BW $mAb_H$ or control vehicle (PBS) intraperitoneally. The mice were then fasted for an additional 5 hours before glucose (1.5 g/kg BW) was given by oral gavage, and blood was collected at 0 and 15 minutes; the protocol was repeated on the mice 1 week and 2 weeks later. Plasma insulin was measured by ELISA.

Similar to the $mAb_m$, the $mAb_H$ neutralized GIP signaling in vitro in a concentration-dependent manner, and the Schild's assay plot showed $mAb_H$ and $mAb_m$ equilibrium dissociation constants of 2.2 μM and 3.2 μM, respectively, indicating similarly that the $mAb_H$ binds more strongly to GIP than does the $mAb_m$. The measured plasma $C_{max}$ values for the 10 and 30 mg/kg BW doses of GIP $mAb_H$ were 10.1±0.7 μg/ml and 32.6±1.0 μg/ml, respectively. The GIP $mAb_H$ inhibited the 15-minute insulin responses to oral glucose at 5 hours, 1 week, and 2 weeks after treatment by 47±21% (P=0.01), 45±21% (P=0.01), and 13.8±31%. The GIP $mAb_H$ was shown to bind GIP with a higher affinity than the $mAb_m$, and similarly it inhibits GIP signaling in vitro more potently than the 10g10 $mAb_m$. Furthermore, the calculated $T_{½}$ for the GIP $mAb_H$ in vivo is comparable to other biological agents currently in use. Combined with the results shown in Example 4, this indicates that weekly, bimonthly, or monthly administration of the GIP mAb$_H$ should prove useful for treating obesity and related disorders in humans.

Example 6

In separate studies, the LC2/HC2 humanized antibody was administered to ob/ob mice. These mice are hyperphagic due to mutations in the gene responsible for the production of leptin. Leptin is a hormone that is important in controlling appetite, by signaling to the brain that the animal is satiated, and thus inhibiting hunger. As a result of the gene mutations for leptin, the ob/ob mouse continues to eat and becomes profoundly obese. This mouse is thus useful as a model for disorders characterized by hyperphagia (abnormally excessive eating). The GIP-binding monoclonal antibody of the present disclosure exerts its effects downstream of the excessive eating, and so is expected to be an effective treatment for hyperphagia.

Ob/ob mice were obtained from Jackson Labs (strain B6.Cg-Lep$^{ob}$/j, Stock No. 000632). The mice were then divided into two groups, a control group and a "GIP-mAb" group which received treatments of the GIP-binding mAb. The mice were fed regular chow (Prolab Isopro RMH 3000). The regular chow provided 26.03% of total calories from protein, 59.66% from carbohydrates, and 14.32% from fat, and 4.18 kcal/gram gross energy. The GIP-mAb mice were injected with the antibody subcutaneously twice per week (30 mg/kg dosage), then weighed once a week.

Figure 23:
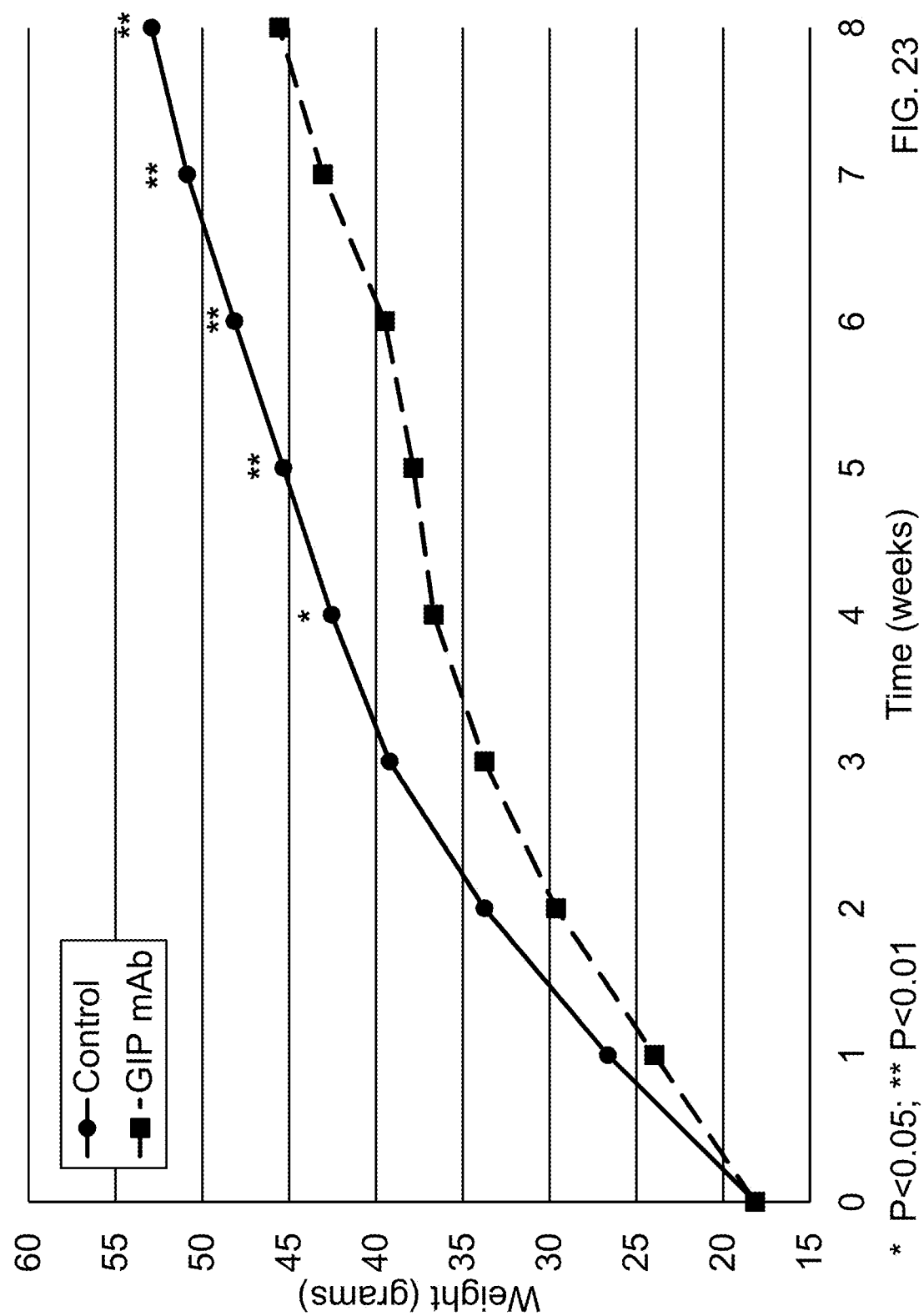
FIG. 23 is a graph showing the weight gain (grams) over time in ob/ob mice which have mutations in the gene responsible for producing leptin, a vital satiety hormone, and thus become markedly hyperphagic and subsequently profoundly obese. The y-axis shows mouse weight in grams, and the range is 15 to 60 in increments of 5. The x-axis depicts time in weeks, and runs from 0 to 8 weeks in increments of 1. The top line (closed circles) represents the weight of control mice, and the bottom line (closed squares) represents the weight of mice treated with the "GIP mAb". This graph indicates that the mice to which the anti-GIP antibody was administered gained significantly (~28%) less weight over time.

FIG. 23 shows the results after 8 weeks. After 8 weeks, the control mice weighed 52.9 grams±1.32 grams. The GIP-mAb control mice weighed 45.6 grams±1.65 grams (P=0.0040). The percent gain from baseline was 192.4%±7.30% for the control, versus 150.4%±9.06% for the GIP-mAb mice (P=0.0031). This difference represents a 27.8% decrease in weight gained. The mean data +/−standard error are also provided in the following table:

|  |  | Base line | Week 1 | Week 2 | Week 3 | Week 4 | Week 5 | Week 6 | Week 7 | Week 8 |
|---|---|---|---|---|---|---|---|---|---|---|
| control | Avg Wt (g) | 18.1 | 26.6 | 33.7 | 39.2 | 42.5 | 45.3 | 48.1 | 50.9 | 52.9 |
|  | Std Error (g) | 0.88 | 0.80 | 0.79 | 0.92 | 0.89 | 1.24 | 1.32 | 1.30 | 1.32 |
| GIP mAb | Avg Wt (g) | 18.2 | 24.0 | 29.6 | 33.7 | 36.7 | 37.8 | 39.5 | 43.1 | 45.6 |
|  | Std Error (g) | 0.60 | 0.58 | 1.02 | 1.44 | 1.63 | 1.41 | 1.53 | 1.67 | 1.65 |

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications, variations, improvements, and substantial equivalents.

The invention claimed is:

1. A monoclonal antibody binding gastric inhibitory polypeptide (GIP), comprising:
   (i) a light chain variable domain comprising a first CDR having the amino acid sequence of SEQ ID NO: 20, a second CDR having the amino acid sequence of SEQ ID NO: 21, and a third CDR having the amino acid sequence of SEQ ID NO: 22, and
   (ii) a heavy chain variable domain comprising a first CDR having the amino acid sequence of SEQ ID NO: 31, a second CDR having the amino acid sequence of SEQ ID NO: 32, and a third CDR having the amino acid sequence of SEQ ID NO: 33.

2. The monoclonal antibody of claim 1, wherein the light chain variable domain comprises the amino acid sequence of SEQ ID NO: 18.

3. The monoclonal antibody of claim 1, wherein the heavy chain variable domain comprises the amino acid sequence of SEQ ID NO: 29.

4. The monoclonal antibody of claim 1, wherein the light chain variable domain comprises the amino acid sequence of SEQ ID NO: 18 and the heavy chain variable domain comprises the amino acid sequence of SEQ ID NO: 29.

5. The monoclonal antibody of claim 1, wherein monoclonal antibody comprises a human constant region.

6. The monoclonal antibody of claim 5, wherein the human constant region is an IgG1 isotype.

7. The monoclonal antibody of claim 5, wherein the human constant region is an IgG2 isotype.

8. The monoclonal antibody of claim 5, wherein the human constant region is an IgG4 isotype.

9. A method of inducing weight loss or of treating hyperphagia, or of treating obesity, type II diabetes, food-induced Cushing's syndrome, or metabolic syndrome, or for reducing fatty tissue buildup in the liver or omentum, or for reducing subcutaneous fatty tissue buildup, comprising:
   administering to a person in need thereof a composition comprising a pharmaceutically effective amount of the monoclonal antibody of claim 1.

10. The method of claim 9, wherein the composition is administered intravenously, intraperitoneally, or subcutaneously.

11. The method of claim 9, resulting in a weight change of at least 5% after five weeks, compared to original body weight before administration of the composition.

* * * * *